(12) United States Patent
Stark

(10) Patent No.: US 6,957,215 B2
(45) Date of Patent: Oct. 18, 2005

(54) MULTI-DIMENSIONAL ASSOCIATIVE SEARCH ENGINE

(75) Inventor: Moshe Stark, Even Yehuda (IL)

(73) Assignee: Hywire Ltd., Netanya (IL)

(*) Notice: Subject to any disclaimer, the term of this patent is extended or adjusted under 35 U.S.C. 154(b) by 481 days.

(21) Appl. No.: 10/315,006

(22) Filed: Dec. 10, 2002

(65) Prior Publication Data

US 2003/0191740 A1 Oct. 9, 2003

Related U.S. Application Data

(60) Provisional application No. 60/337,143, filed on Dec. 10, 2001.

(51) Int. Cl.$^7$ .............................................. G06F 17/30
(52) U.S. Cl. ........................................ 707/6; 711/108
(58) Field of Search .............................. 707/6; 711/108

(56) References Cited

U.S. PATENT DOCUMENTS

| | | | | |
|---|---|---|---|---|
| 5,920,886 A | * | 7/1999 | Feldmeier | 711/108 |
| 6,237,061 B1 | * | 5/2001 | Srinivasan et al. | 711/108 |
| 6,374,326 B1 | * | 4/2002 | Kansal et al. | 711/108 |
| 6,606,681 B1 | * | 8/2003 | Uzun | 711/108 |
| 6,633,953 B2 | * | 10/2003 | Stark | 711/108 |
| 6,711,661 B1 | * | 3/2004 | Zabarski et al. | 711/202 |
| 6,732,228 B1 | * | 5/2004 | Willardson | 711/108 |
| 6,757,780 B2 | * | 6/2004 | Stark | 711/108 |
| 6,789,116 B1 | * | 9/2004 | Sarkissian et al. | 709/224 |
| 6,839,800 B2 | * | 1/2005 | Stark | 711/108 |
| 2002/0049922 A1 | * | 4/2002 | Direen | 714/1 |
| 2004/0128434 A1 | * | 7/2004 | Khanna et al. | 711/108 |

OTHER PUBLICATIONS

Bruza et al, Interactive Internet search: Keyword, directory and query reformulation mechanisms compared, PROC 23$^{rd}$ ACM SIGIR conference on Research and development in information retrieval, Jul. 2000.*

U.S. Appl. No. 09/779,941, filed Feb. 2001, Stark.
U.S. Appl. No. 10/040,389, filed Jan. 2002, Stark.
U.S. Appl. No. 10/206,189, filed Jul. 2002, Kastoriano et al.
U.S. Appl. No. 10/229,065, filed Aug. 2002, Stark.

Goodman et al: "Discrete and Computational Geometry" CRC Press 1997.
De Berg: "Computational Geometry, Algorithms and Applications" Springer–Verlag 2000.
Gupta et al; "Algorithms for Packet Classification": IEEE Network Mar./Apr. 2001 pp. 24–32.
Lakshman et al; "High–Speed Policy–based Packet Forwarding Using Efficient Multidimensional Range Matching" ACO Comp Communication Review 28(4) pp. 203–214 ACM SIGCOMM'98 (Sep. 1998).
Decasper et al; "Router plugins: a software architecture for next–generation routers" IEEE/ACM trans, Networking 8(1):2–15, Feb. 2000.
Semeria; "Implementing a Flexible Hardware–based Router for the New IP Infrastructure".
Peng et al; "Content–Addressable Memory (CAM) and its network applications" International IC–Korea Conference proceedings, Altera International Ltd.

* cited by examiner

Primary Examiner—Wayne Amsbury
(74) Attorney, Agent, or Firm—Mark M. Friedman

(57) ABSTRACT

A device for, and method of, storing data in a memory, and for extracting the data therefrom based on a multi-dimensional input (MDI) key, the device including a first and at least a second associative search engine (ASE), each including: (i) a memory having: (A) a first array of cells containing a field of entries, each of the cells being accessible via an input key including a string corresponding to at least a portion of the MDI key, and (B) a second array of cells having a plurality of associated data entries, each of the associated data entries being associated with a particular one of the entries in the first array, and (ii) control logic for operatively connecting the first and the second ASE, the control logic for processing at least a portion of the entries in the first array from each ASE, in response to the input key, so as to determine a match between the input key and an entry of said entries in said field; the control logic for producing a result pertaining to an associated data entry based on the determination, and wherein the control logic utilizes the result from the first ASE in the processing of the second ASE, so as to narrow searching within the second ASE.

57 Claims, 33 Drawing Sheets

"a<b" means that a has a higher priority than b $$[x_L, x_H) X\{[y_{L1}, y_{H1}) + [y_{L2}, y_{H2})\} \equiv [x_L, x_H) X[y_{L1}, y_{H1}) + [x_L, x_H) X[y_{L2}, y_{H2})$$

$\{[x_{L1}, x_{H1}) + [x_{L2}, x_{H2})\} X [y_L, y_H) \cong [x_{L1}, x_{H1}) X [y_L, y_H) + [x_{L2}, x_{H2}) X [y_L, y_H)$ $$\{[x_{L1}, x_{H1})/A_1/p_1 + [x_{L2}, x_{H2})/A_2/p_2\} X[y_L, y_H) \equiv$$
$$[x_{L1}, x_{H1}) X[y_L, y_H)/A_1/p_1 + [x_{L2}, x_{H2}) X[y_L, y_H)/A_2/p_2$$

$$\text{Field}_i = \text{Field}^0_i \mid \text{Field}^1_i \mid \ldots \mid \text{Field}^{m-2}_i \mid \text{Field}^{m-1}_i$$

$$[x_0,x_1)/T_0 \longrightarrow [y_0,y_2)/A_0/p_0$$

$$[x_2,x_3)/T_1 \longrightarrow [y_1,y_3)/A_1/p_1$$

$$[x_0, x_1)/T_0 \longrightarrow [y_0, y_1)/A_0/p_0$$

$$[x_1, x_2)/T_1 \longrightarrow \begin{cases} [y_0, y_1)/A_0/p_0 \\ [y_2, y_3)/A_1/p_1 \end{cases}$$

$$[x_2, x_3)/T_2 \longrightarrow [y_2, y_3)/A_1/p_1$$

$$[x_0, x_1)/T_0 \longrightarrow [y_0, y_2)/A_0/p_0$$

$$[x_1, x_2)/T_1 \longrightarrow \begin{cases} [y_0, y_2)/A_0/p_0 \\ [y_2, y_3)/A_1/p_1 \end{cases}$$

$$[x_2, x_3)/T_2 \longrightarrow [y_1, y_3)/A_1/p_1$$

MULTI-DIMENSIONAL ASSOCIATIVE SEARCH ENGINE

This application draws priority from U.S. Provisional Patent Application Ser. No. 60/337,143, filed Dec. 10, 2001.

FIELD AND BACKGROUND OF THE INVENTION

The present invention relates to associative search engines (ASEs) and, in particular, to associative search engines for performing operations on multi-dimensional entries having associated data or actions, in response to a multi-dimensional input key.

Packet classification, a well-known problem in computer science, can be defined as follows: given a data packet with certain predefined multiple components, also called packet fields, and an action taken on field-specific packet, this packet can be sorted on the basis of a different action to be taken. Classification is the action of sorting, among all the data packets, the packets that result in the same action.

The set of rules that determines the class to which the packet belongs, is stored in an information base called Classification Information Base (CIB) or a Classifier. The relevant components or fields of a specific data packet classification are assembled into a construct called a Classification Key. The Classification Key forms a CIB query, which results in a specific action to be taken on the packet. Since the Classification Key incorporates multiple fields, and since the CIB results are multiple-field dependent, the result is defined as a Multi-Field Classification.

The CIB structuring, classification methods and CIB maintenance are considered to be a very important problem, but a difficult one to resolve, and has been subject to extensive research for the last 30 years. Computational Geometry, a relatively new branch of mathematics, emerged in the late 1970s and has been extensively used to explore various alternatives (J. Goodman et al., "Discrete and Computational Geometry", CRC Press 1997; de Berg et al., "Computational Geometry, Algorithms and Applications", Springer-Verlag 2000).

These topics began to receive special attention once it became clear that classification is of strategic importance in data communications. The recognition of classification as a performance and intelligence bottleneck arose with the Internet's performance and functionality. This bottleneck was noticed in the early 1990s, and began to receive significant academic attention in the second half of the decade. A flood of research work has been published on the topic (P. Gupta, et al., "Algorithms for Packet Classification", IEEE Network, March/April 2001 pp. 24–32).

A very interesting approach is taken by T. Lakshman, et al., in "High-Speed Policy-based Packet Forwarding Using Efficient Multidimensional Range Matching", ACO Computing Communication Review 28(4) pp. 203–214, ACM SIGCOMM'98 (September 1998). This approach is different from a Trie-based approach, and utilizes the so called "bit parallelism". The use of multi-dimensional range matches is innovative, however, the design practically limits the implementation hardware to several thousand rules and to a classification rate not higher than several million classifications per second.

Today, there are two main-stream approaches to Classifier design (see Lakshman, et al.) in a router or a switch: algorithmic and TCAM.

The Algorithmic Approach

In the algorithmic approach, the CIB consists of either:

a general-purpose microprocessor, a micro-controller, or a network processor, which executes the algorithm embedded in a low-performance/low-cost memory.

The microprocessor fetches data from the memory and makes a decision from where to fetch memory data in the next step. This continues for many steps until the classification is completed. Since the performance requirements are not very high, a cheap but reasonable solution can be worked out (see Decasper, et al., "Router plugins: a software architecture for next-generation routers", IEEE/ACM Trans. Networking, 8(1):2–15, February 2000), or a dedicated ASIC or Search Engine: This type of solution is based upon a specially built processor optimized for fast and efficient execution of the classification task.

To this end, the search engine incorporates specialized hardware, which executes an algorithmic step in a single clock cycle. Also, the engine interfaces with the memory via a very wide data bus, in order to reduce the number of steps. This facilitates bringing in sufficient amount of data to make a more intelligent step towards a solution (see C. Semeria, "Implementing a Flexible Hardware-based Router for the New IP Infrastructure", Juniper Networks, September 2001).

The algorithms typically used in both cases are Trie data structures (see Gupta, et al.). All these algorithms are multiple step algorithms, some of which execute a search in fewer steps than others. Typically, those algorithms that are extremely fast, executing a classification in a very few clocks, cause an exponential explosion in the requisite amount of storage space. This results in a very bulky, power-consuming solution. Those algorithms that are optimized for low storage requirements are very slow, and do not meet the performance criteria of high-performance routers.

In most cases, there is an additional problem due to backtracking, which results when an algorithm reaches a dead-end and the search must either start over in a completely different direction, or backtrack one or more steps and restart from there.

Due to the restricted memory bus bandwidth, these methods also end up taking a long time for CIB maintenance.

The Ternary CAM (TCAM) Approach

The TCAM approach is quite popular, currently, especially for high-performance classification duties (see M. Peng et al., "Content-Addressable memory (CAM) and its network applications", International IC—Korea Conference proceedings, Altera International Ltd.). The TCAM advantage lies in the capability of performing one classification in every clock cycle. Consequently, TCAMs are considered to be the fastest classification solution available today. In addition, TCAMs have a deterministic classification time, as they classify always in a single clock cycle. TCAMs, however, are not problem-free:

Since TCAMs compare all entries at-once with the classification Key, they consume excessive amounts of power and tend to overheat.

Despite the ability to perform one classification per clock cycle, TCAMs are relatively slow in comparison to SRAMs (or DRAMs) developed using the same process technology and the same circuit design style. A TCAM can run classifications at about one fifth the rate of a similar SRAM. This is due to the TCAM cell complexity and density.

TCAMs are not scalable in their widths. The widest classification word that a modern TCAM supports today has a width of 576 bits. Hence, there is a limit to the number of fields and field-width that TCAM-based Classifiers can handle. The scalability limitations of TCAM-based CIBs often constrain router intelligence and performance.

TCAMs are architecturally limited in the number of classification rules they handle, because a limited number of TCAM components can be used in a single CIB. Today, this is not an issue, due to a limited size of classification rules in a Classifier. However, it may become an issue in a year or two.

TCAMs are storage inefficient. A TCAM word can be programmed to several fixed widths. For instance, if a TCAM supports 36, 72, 144, 288 and 576 key widths, then if the CIB requires 128-bit keys, 16 bits are unutilized in every key entry. This waste is typically worse for longer classification keys. Also, TCAM are inherently limited in the way that they can handle fields. Fields can use ranges, which are power-of-2 integers rather than ANY integer. This does not eliminate the possibility to express any rule, but it may become highly-storage-inefficient and therefore impractical.

In certain cases, a precisely expressed classification rule requires a flag-based logical expression. It is not viable to economically support such expressions inside the TCAM. Therefore, designers must resort to external hardware to construct such an expression and then use the output signal as a bit to drive the TCAM. This is not only expensive, but is hardwired, and therefore puts a limit on the flexibility of the solution. Ideally, one would be able to create any flag-based logical expression through reprogramming, since this would enable a great flexibility and incremental improvement by resorting to new software versions rather than to changes in hardware.

Thus, an 18M ternary-bit TCAM, which theoretically stores over 147,000 classification rules, 128 bits per rule, statistically fits in only about 80,000 classification rules. Nonetheless, this is considered quite reasonable, when compared to the limitations of the fast algorithmic trie-based methods.

It is important to remember that the wider the classification key, the slower the TCAM. For instance, a state-of-the-art TCAM, configured for a word-width of 144 bits, runs on a 66 MHz clock; the same TCAM, when configured for a word-width of 576 bits, operates on a 25 MHz clock.

TCAM maintenance is not autonomous. An external processor manages the TCAM address space. This occupies a great deal of the processor bandwidth as well as the write-up and the verification of the maintenance software drivers.

There is therefore a recognized need for, and it would be highly advantageous to have, a device for, and a method of performing operations on multi-dimensional entries having associated data or actions characterized by high storage efficiency and reduced power consumption, with respect to prior art devices and methods. It would be of further advantage if the inventive device and method would provide unlimited scalability, both horizontally (in terms of the number of fields and field width) and vertically (in terms of the number of classification rules), and in addition, would have a classification clock that is independent of the classification key width.

SUMMARY OF THE INVENTION

The present invention is a method of, and device performing operations on multi-dimensional entries having associated data or actions, in response to a multi-dimensional input key, using associative search engines. The utility of Multi-Dimensional Ranges (MDRs) in compactly representing multi-field information bases is shown. The present invention is particularly suitable for packet classification in the communications field.

According to the teachings of the present invention there is provided a device for storing data in a memory, and for extracting the data therefrom based on a multi-dimensional input (MDI) key, the device including a first and at least a second associative search engine (ASE), each including: (i) a memory having: (A) a first array of cells containing a field of entries, each of the cells being accessible via an input key including a string corresponding to at least a portion of the MDI key, and (B) a second array of cells having a plurality of associated data entries, each of the associated data entries being associated with a particular one of the entries in the first array, and (ii) control logic for operatively connecting the first and the second ASE, the control logic for processing at least a portion of the entries in the first array from each ASE, in response to the input key, so as to determine a match between the input key and an entry of the entries in the field; the control logic for producing a result pertaining to an associated data entry based on the determination, and wherein the control logic utilizes the result from the first ASE in the processing of the second ASE, so as to narrow searching within the second ASE.

According to another aspect of the present invention there is provided a method of storing data in a memory, and for extracting the data therefrom based on a multi-dimensional input (MDI) key, the method including the steps of: (a) providing a device including: (i) a first and at least a second associative search engine (ASE), each ASE including: (A) a memory including: (I) a first array of cells containing a field having a plurality of entries, and (II) a second array of cells having a plurality of associated data entries, wherein each of the associated data entries is associated with a particular one of the entries in the first array, and (B) control logic for the memory; (b) inputting an input key to each ASE, the input key including a string corresponding to at least a portion of the MDI key; (c) processing at least a portion of the entries in the first array from each ASE, in response to the input key, so as to make a determination if there exists a match between the input key and an entry of the entries in the field; (d) producing a result based on this determination, the result pertaining to at least one of the associated data entries, and (e) utilizing the result from the first ASE in the processing of step (c) of the second ASE.

According to yet another aspect of the present invention there is provided a method of storing data in a memory, and for extracting the data therefrom based on a multi-dimensional input (MDI) key, the method including the steps of: (a) providing a device including: (i) a plurality of associative search engines (ASEs) including a first ASE and at least a second ASE, each ASE including: (A) a memory including: (I) a field containing a first array of cells, and (II) a second array of cells, and (B) control logic for the memory; (b) storing a plurality of entries within the first array of cells, such that the field is accessible via an input key including a string, the string corresponding to at least a portion of the MDI key, wherein the entries in the first array of at least one of the first ASE and the second ASE include range boundary information; (c) storing a plurality of associated data entries within the second array of cells, such that each of the associated data entries is associated with a particular one of the entries in the first array, and (d) processing the plurality of associated data entries so as to convert overlapping ranges within the range boundary information into disjoint ranges.

According to further features in the described preferred embodiments, each field is configured so as to correspond to at least a portion of the MDI key.

According to still further features in the described preferred embodiments, each field is configured so as to correspond to a different portion of the MDI key.

According to still further features in the described preferred embodiments, the result from the first ASE is incorporated within the input key of the second ASE.

According to still further features in the described preferred embodiments, the device further includes: (c) at least one concatenating element for concatenating the result from the first ASE in the input key of the second ASE to form a concatenated input key.

According to still further features in the described preferred embodiments, each concatenating element is operatively paired with each at least second ASE.

According to still further features in the described preferred embodiments, the device further includes: (c) at least one selecting element for selecting, based on the result from the first ASE, a portion of the field within the first array of the second ASE so as to narrow the searching within the second ASE.

According to still further features in the described preferred embodiments, the result includes a match indicator.

According to still further features in the described preferred embodiments, the field of entries in the first array of at least one of the first and second ASE includes range boundary information.

According to still further features in the described preferred embodiments, the first array has at least two dimensions, the first array consisting of rows and columns, the second array has at least two dimensions, the second array consisting of rows and columns, and wherein each of the associated data entries has a unique pair of row and column indices for association with a unique pair of row and column indices of a particular one of the entries within the field of entries.

According to still further features in the described preferred embodiments, the entries in the field of at least one ASE includes single integer data, and wherein the field of entries of an ASE of the at least a second ASE includes range boundary information.

According to still further features in the described preferred embodiments, the concatenating element is designed and configured such that the result forms at least one most significant bit of the concatenated input key.

According to still further features in the described preferred embodiments, the field of entries within the first array is maintained in a monotonic order.

According to still further features in the described preferred embodiments, the field including single integer data is disposed within the first ASE.

According to still further features in the described preferred embodiments, the processing of the entries within the field of the first ASE and the field of the at least second ASE is sequentially ordered such that a single integer data field is processed first.

According to still further features in the described preferred embodiments, the processing of the entries within the field of the first ASE and the field of the at least second ASE is sequentially ordered such that: (i) any single integer data fields are processed prior to range fields, and (ii) among the range fields, more disjoint fields are processed prior to less disjoint fields.

According to still further features in the described preferred embodiments, at least two of the first ASE and the at least second ASE are configured to handle a long string of a single dimension of the MDI key, the device being designed and configured to split the long string into at least two input keys, each of the input keys for inputting into a different one of the first ASE and the second ASE.

According to still further features in the described preferred embodiments, the MDI key is one of a series of MDI keys, the device being designed and configured to process portions of the MDI keys by pipelining, so as to improve a performance of the device.

According to still further features in the described preferred embodiments, the MDI key is one of a series of MDI keys, the series represented by $k_0 \ldots k_m, k_{m+1} \ldots k_n$, wherein:

k is one of the MDI keys,
  $k_0$ is a first of the MDI keys,
  n is a number of a last of the MDI keys, $n \geq 1$, and
  m is a number of one of the MDI keys, $n \geq m+1$, and wherein at least two ASEs of the first ASE and the at least second ASE are designed and configured to process portions of the MDI keys by pipelining, such that the second of the ASEs processes a portion of key $k_m$ while a first of the ASEs processes a different portion of key $k_{m+1}$, so as to improve a performance of the device.

According to still further features in the described preferred embodiments, the range boundary information is a single range-boundary value.

According to still further features in the described preferred embodiments, the memory is designed and configured to include: (C) range validity information for each of the range boundary information.

According to still further features in the described preferred embodiments, each range boundary value is disposed in a separate memory cell of the first array, so as to produce a monotonic order.

According to still further features in the described preferred embodiments, each ASE further includes: (iii) sorting means for arranging the range boundary information in a monotonic order within the first array.

According to still further features in the described preferred embodiments, the associative search engine further includes: (iii) output means for outputting the result.

According to still further features in the described preferred embodiments, the first ASE and the at least second ASE are disposed within a single chip.

According to still further features in the described preferred embodiments, the at least one concatenation element is disposed within the at least second ASE.

According to still further features in the described preferred embodiments, the MDI key includes an IPv4 classification key.

According to still further features in the described preferred embodiments, the MDI key includes an Ipv6 classification key.

According to still further features in the described preferred embodiments, the processing step of the method includes searching, and the utilizing step is performed so as to narrow the searching within the second ASE.

According to still further features in the described preferred embodiments, the utilizing step includes incorporating the result from the first ASE in the input key of the second ASE.

According to still further features in the described preferred embodiments, the utilizing step includes concatenating the result from the first ASE in the input key of the second ASE to form a concatenated input key.

According to still further features in the described preferred embodiments, the utilizing step includes selecting a sub-set of the entries in the first array of the second ASE, based on the result from the first ASE, the sub-set being smaller than the plurality of entries in the first array of the second ASE.

According to still further features in the described preferred embodiments, the result is a singular result obtained by pre-processing over disjoint ranges.

According to still further features in the described preferred embodiments, the result is a singular result selected from at least two results derived from overlapping ranges by post-processing using priority rules.

According to still further features in the described preferred embodiments, the concatenating is performed such that the result forms at least one most significant bit of the concatenated input key.

According to still further features in the described preferred embodiments, the processing to produce the disjoint ranges is based on at least one pre-determined priority rule.

According to still further features in the described preferred embodiments, the processing to produce the disjoint ranges is pre-processing.

According to still further features in the described preferred embodiments, the processing further includes identifying at least one redundant data entry, the redundant data entry being redundant with a particular data entry among the associated data entries.

According to still further features in the described preferred embodiments, the processing further includes eliminating the at least one redundant data entry so as to save space in the memory.

According to still further features in the described preferred embodiments, corresponding to the at least one redundant data entry is at least one entry of the entries in the field, the processing further including re-associating the entry in the field with the particular data entry among the associated data entries.

According to still further features in the described preferred embodiments, corresponding to the at least one redundant data entry and the particular data entry are a particular plurality of entries in the field, the processing further including separating out the particular plurality of data entries in the field as a common factor, so as to save space in the memory.

RSE devices of the present invention, built with simple or compound modules and integrated with Concatenation Logic, provide Multi-Dimensional Range Search Engines having capabilities that are unique to RSE, such as storage of any number of rules, number of fields and field widths, and scalability options to build an information base of any size with little or no glue logic. This yields RSE devices with an unlimited number of classification fields and an unlimited classification field width.

The use of tags in the search procedures in the Multi-Dimensional Ranges, along with the storage efficiency advantages of the inventive range representation over the prefix notation used in conventional CIDR address ranges, and the benefits of RSEs in performance, power consumption, flexibility and scalability, result in significantly higher density, performance and scalability for packet classification as compared with state-of-the-art Ternary CAMs (TCAMs).

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
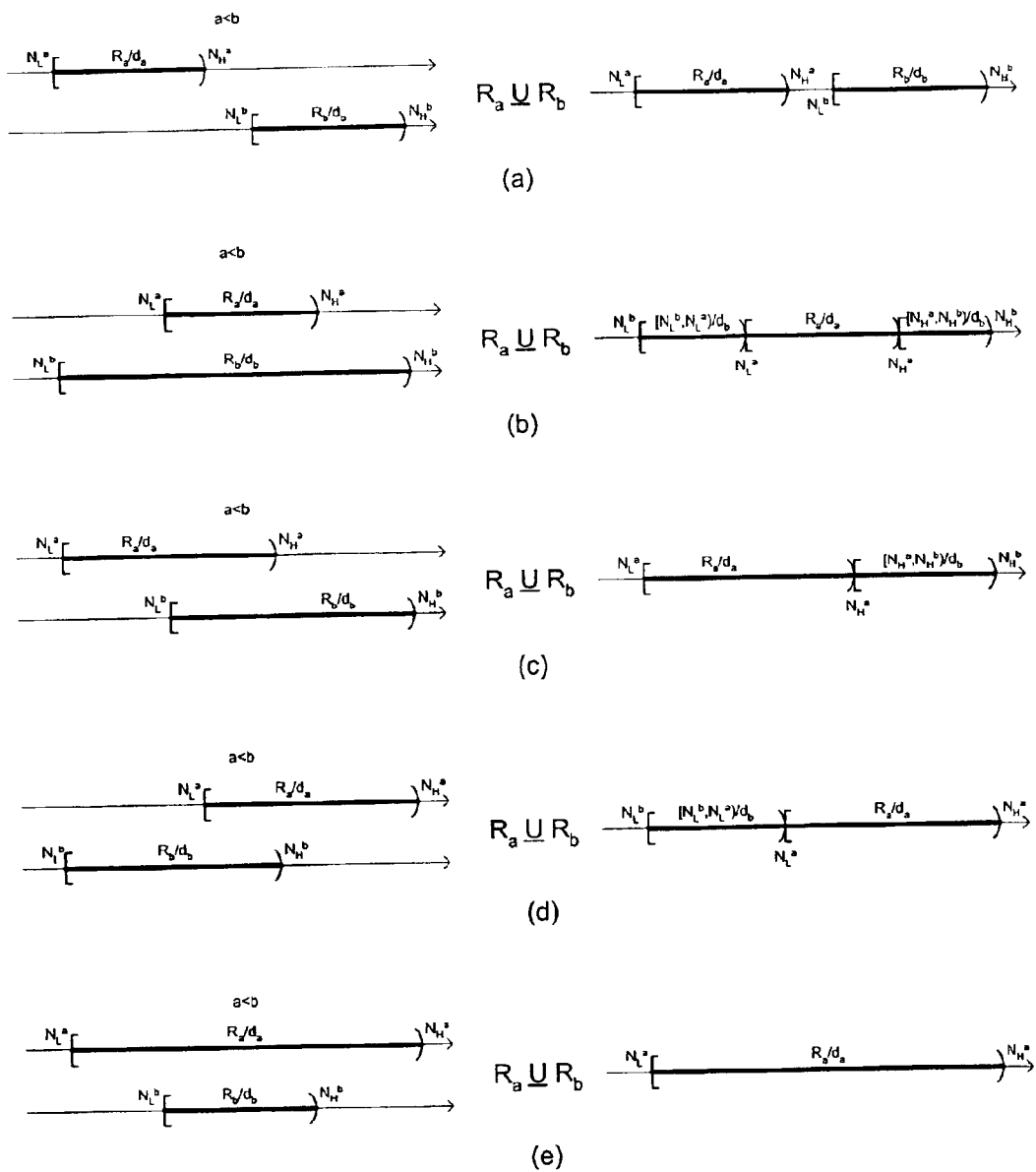
FIG. 1 is a graphical illustration of the combination of two overlapping ranges and the resulting equivalent set of non-overlapping ranges.

The present invention is a method of, and device performing operations on multi-dimensional entries having associated data or actions, in response to a multi-dimensional input key, using associative search engines. A novel concept, Multi-Dimensional Ranges (MDRs), is introduced, and the utility of such MDRs in compactly representing multi-field information bases is shown. The present invention is particularly suitable for packet classification in the communications field.

The concept presented here provides the capability to decompose a d-Dimensional Range Information Base into d one-dimensional ranges, and each d-Dimensional Key into d one-dimensional keys, and thus transform the difficult search procedure in a d-Dimensional Information Base into d one-dimensional range searches, which can be readily performed by d one-dimensional Range Search Engines (RSEs). This concept can be used for a d-Dimensional Information Base with single (or "binary") integers, which can be viewed as a special case of a d-Dimensional Range Information Base.

The search algorithm presented involves the use of a Tag as a result (or associated data) of each one-dimensional range search, and concatenate this Tag with the next one-dimensional key searched in the next dimension of the Range Information Base in the following step. This sequence of d concatenated steps results in an Associated Data A (or Action A), which is associated with the d-dimensional range. The search algorithm steps can be pipelined to maximize the d-dimensional search throughput, regardless of the latency of the search procedure.

In the communications field, the throughput is expressed in terms of the number of packet classifications per second. A link diagram is provided as a technique to map classification rules into the Multi-Dimensional Classification System. The Classification System describes the entries in each dimension as well as their linkage to the following dimension. The last stage specifies the action A to be performed on a Multi-Dimensional Key that matches the rule.

The concept of Multi-Dimensional Ranges is based on the concept of one-dimensional ranges, as disclosed in my co-pending U.S. patent application, Ser. No. 09/779,941, which is incorporated by reference for all purposes as if fully set forth herein.

The multi-dimensional classification system can be implemented, for binary integers, with a RAM-based Binary CAM device, as taught in my co-pending U.S. patent application, Ser. No. 10/229,054, which is incorporated by reference for all purposes as if fully set forth herein. For range entries, the multi-dimensional classification system can be implemented with the RAM-Based RCAM, disclosed in my co-pending U.S. patent application, Ser. No. 10/229, 065, which is incorporated by reference for all purposes as if fully set forth herein.

Other, improved RCAM implementations can be used. The first, a multiple module RCAM, is disclosed in my co-pending U.S. patent application, Ser. No. 10/040,389, and is hereby incorporated by reference for all purposes, as if fully set forth herein. The multiple module RCAM allows interconnection of multiple RAM-based RCAM modules into a single multiple-module device.

Another improved RCAM implementation, called multi-RAM RCAM, includes a group of RAMs in a single device, as taught in my co-pending U.S. patent application, Ser. No. 10/206,189, which is incorporated by reference for all purposes as if fully set forth herein. Several Multi-RAM RCAM devices can be integrated in multiple modules to form multiple-modules of multi-RAMs.

The principles and operation of the multi-dimensional associative search engines of the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawing. The invention is capable of other embodiments or of being practiced or carried out in various ways. Also, it is to be understood that the phraseology and terminology employed herein is for the purpose of description and should not be regarded as limiting.

1. Range Principles

1.1 Range Definition

A Range R is defined as a set of all the integers K that comply with the condition $N_L \leq K < N_H$, where $N_L$ and $N_H$ are two integers such that $0 \leq N_L < N_H$. This condition is denoted by $$R = [N_L, N_H)$$

where $N_L$ and $N_H$ are defined as the Lower and Upper Range Boundaries, respectively.

The Range definition implies that the Range Lower Boundary $N_L$ belongs to the Range, whereas the Range Upper Boundary $N_H$ does not belong to the Range. The Range Lower Boundary is a Closed Boundary in mathematical terms, whereas the Range Upper Boundary is an Open Boundary. Thus, the Range as defined is a Semi-Closed/Semi-Open interval of integers.

The Range as defined above provides a very efficient representation for address ranges in Classless Inter Domain Routing (CIDR) used in Internet Protocol Version 4 (IPv4), the currently used IP version.

Definitions, basic properties and operations of ranges, RCAM implementations, and applications of the RCAM for Classless Inter Domain Routing (CIDR) have been developed in my above-referenced, co-pending U.S. patent applications (Ser. Nos. 09/779,941 and 10/229,065).

1.2 Range-Associated Data and Match Value

The most common operation performed upon ranges is a search and identification of the range that contains a submitted key K (an integer), and, as a result, retrieval of associated data (another integer) that corresponds uniquely to the identified range.

Two ranges are called Overlapping Ranges if there is any integer K that is included in both ranges. In general, a Key Search over a set of overlapping ranges may yield inconsistent results, as the key may be found in several of these ranges, each one having its own unique associated data. To obtain associated data from overlapping ranges, each range is assigned a Priority. Then, if the Key Search results in several matches, the associated data of the highest-priority matching range is selected.

The submitted integer K is searched in the set $\mathfrak{R}$ of overlapping ranges and, if found, a single integer $d \geq 0$ is retrieved from the corresponding set D of Associated Data; this integer is called Associated Data. Besides, a Boolean variable m, called Match value, assumes the value "1", indicating a Match. If i is the highest-priority index (or lowest index value) of all the matching ranges in $\mathfrak{R}$, then $d = d_i$ and $m_i =$"1". If the submitted integer K is not found in $\mathfrak{R}$, the Match value assumes the value "0", indicating that there is No-Match. Then, the value of d has no meaning, indicated by d=x, where x represents a Don't Care.

This process of Associated Data retrieval, in which the submitted Key is first searched in all the ranges, is called Post-Processing. It allows a simple but inefficient implementation in hardware, and results in high power consumption and search performance that varies with the number of priority rules.

1.3 Equivalent Non-Overlapping Range Set and Related Range Operations

An alternative and more efficient method to search for the submitted key K and retrieve the associated data, called Pre-Processing, is based on the combination of the overlapping ranges and their conversion to equivalent non-overlapping ranges prior to the search. In this method, the original overlapping range set $\mathfrak{R}$ is transformed into an Equivalent Non-Overlapping Range Set that yields consistently the same associated data from an Associated Data Set corresponding to the Equivalent Non-Overlapping Range Set.

In a Non-Overlapping Range Set, an integer K cannot belong simultaneously to two different ranges. This makes the notion of range priority indispensable.

A Non-Overlapping Range Set and an Overlapping Range Set are equivalent if and only if for every integer K the two yield the same results, i.e., the same Match values and Associated Data.

The combination of two overlapping ranges is defined in terms of the two overlapping ranges $R_a/d_a$, that represents a range $R_a = [N_L^a, N_H^a)$ with an Associated Data $d_a$, and $R_b/d_b$, that represents a range $R_b = [N_L^b, N_H^b)$ with an Associated Data $d_b$, where a<b; that is, $R_a$ has a higher priority than $R_b$.

The overlapping $R_a$ and $R_b$ lead to several possible combinations. The combination results are illustrated in FIG. 1 and summarized in Table 1. In each of these combinations, $R_a$ has a higher priority than $R_b$ and the result always contains the original $R_a$; however, $R_b$ is always replaced by newly created ranges or is completely eliminated.

The $\underline{U}$ sign designates the operation that combines the two ranges. Range Algebra is distinct in the sense that the $\underline{U}$ operand result depends not only on value of the basic elements but also on their boundary values. The basic principles of the Range $\underline{U}$ operation are covered in my above-referenced co-pending applications.

TABLE 1

Combination of Two Overlapping Ranges and the Resulting Equivalent Non-Overlapping Ranges

| Topological Relation Between $R_a$ and $R_b$ | | Result: | |
| --- | --- | --- | --- |
| $N_L^a$ | $N_H^a$ | $R_a \, U \, R_b$ | Comment |
| $N_L^a \in R_b$ | $N_H^a \in R_b$ | $[N_L^b, N_L^a)/d_b, R_a/d_a, [N_H^a, N_H^b)/d_b$ | $R_a$ is included in $R_b$ |
| $N_L^a \notin R_b$ | $N_H^a \in R_b$ | $R_a/d_a, [N_H^a, N_H^b)/d_b$ | |
| $N_L^a \in R_b$ | $N_H^a \notin R_b$ | $[N_L^b, N_L^a)/d_b, R_a/d_a$ | |
| $N_L^a \notin R_b$ | $N_H^a \notin R_b$ | $R_a/d_a$ | $R_b$ is included in $R_a$ |

In general, there are five possible different results when two ranges are combined using the $\underline{U}$ operator. FIG. 1 illustrates graphically these results in five separate drawings, FIG. 1(a) through FIG. 1(e). The original Ranges $R_a$ and $R_b$ are depicted at the left side of each drawing. The $\underline{U}$ operation result is depicted at the right side of each drawing. In all the cases, $R_a$ assumes a higher priority than $R_b$, that is, a<b.

FIG. 1(a) corresponds to the simple case of non-overlapping ranges, which remain unchanged; this case is not listed in Table 1. FIG. 1(b) through FIG. 1(e) correspond to the four cases presented in the table. In FIG. 1(a), $R_a$ and $R_b$ remain unchanged after the $\underline{U}$ operation. In FIG. 1(e), $R_a$ remains unchanged whereas $R_b$ is eliminated. In FIG. 1(b) through FIG. 1(d), $R_a$ remains unchanged, $R_b$ disappears, and one or two ranges are created.

Two Non-overlapping Ranges $R_i$ and $R_{i+1}$ are called Adjacent Ranges, if they share one boundary, that is $N_H^i = N_L^{i+1}$. According to this definition, $[N_L^b, N_L^a)$ and $R_a$ in FIG. 1(b) are Adjacent Ranges as they share $N_L^a$, which is the open boundary of $[N_L^b, N_L^a)$ and the closed boundary of $R_a$, two non-overlapping ranges. Similarly, $R_a$ and $[N_H^a, N_H^b)$ in the same figure are Adjacent Ranges, sharing $N_H^a$, which is the open boundary of $R_a$ and the closed boundary of $[N_H^a, N_H^b)$.

Adjacent Ranges enable a compact way of representing ranges, which results in a significant saving in storage space. The shared boundaries of the Adjacent Ranges in FIG. 1(b) are marked twice, once as the open boundary of a left-hand range, and once as a closed boundary for the right-hand range.

An Adjacent Range Set, $$\Re^A = \{[N_1,N_2),[N_2,N_3), \ldots ,[N_{i-1},N_i),[N_i,N_{i+1}), \ldots ,[N_{q-1},N_q),[N_q,N_{q+1})\}$$

and its Associated Data Set, $$D^A = \{d_1, d_2, \ldots, d_{i-1}, d_i, \ldots, d_{q-1}, d_q\},$$

can be represented by the boundary integer set $$\Re^A = [N_1, N_2, N_3, \ldots N_{i-1}, N_i, N_{i+1}, \ldots, N_{q-1}, N_q, N_{q+1}),$$

where $N_1$ is the closed boundary of the leftmost Adjacent Range, $N_2, N_3, \ldots, N_{i-1}, N_i, \ldots N_{q-1}, N_q$ are the shared boundaries of the Adjacent Ranges, and $N_{q+1}$ is the open boundary of the rightmost Adjacent Range.

This definition implies that $N_1 < N_2 < N_3 < \ldots < N_{i-1} < N_i < \ldots < N_{q-2} < N_{q-1} < N_q < N_{q+1}$.

Searching in $\Re^A$ for a Range $R_i$ which contains the integer K, and retrieving the Associated Data $d_i$, implies finding i such that $N_i \leq K < N_{i+1}$.

The above definition yields a compact Adjacent Range representation, because each shared boundary is presented only once, instead of twice in the Adjacent Range notation used above. For instance, the following notations are equivalent in the case shown in FIG. 1(b):

$$\{[N_L^b, N_L^a), R_a, [N_H^a, N_H^b)\} = [N_L^b, N_L^a, N_H^a, N_H^b)$$

FIG. 1 and Table 1 show that if $R_a$ and $R_b$ are two Overlapping Ranges, then $\Re^A = R_a \underline{U} R_b$ is an Adjacent Range Set, whose compact representation is $[N_1^A, \ldots, N_n^A)$, where $2 \leq n \leq 4$.

Using the $\underline{U}$ operator repeated times upon an Overlapping Range Set $\Re$ and its Associated Data Set D, and applying the Commutative and Associative Laws for this operator until all the resulting ranges become non-overlapping, yield an Equivalent Non-overlapping Range Set with an Associated Data Set.

In general, the number of boundaries in the Equivalent Non-Overlapping Range is significantly less than the sum of all the boundaries of the overlapping ranges. Some of these boundaries may coincide with one or more of the overlapping range boundaries.

Figure 2:
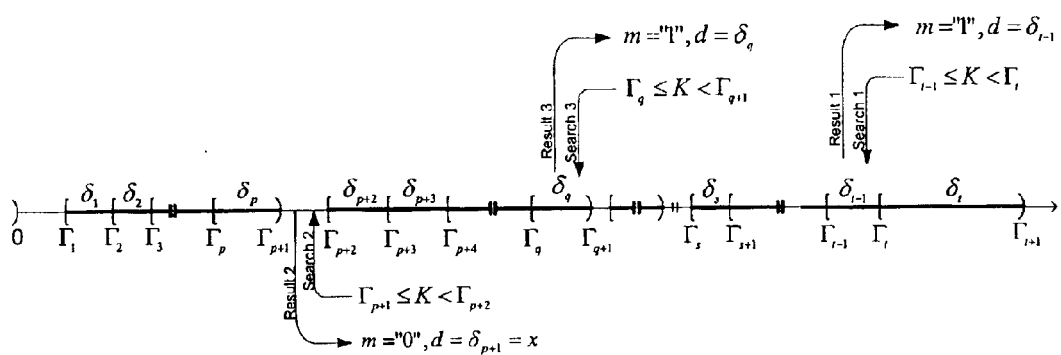
FIG. 2 is a graphical illustration of the key search process within a non-overlapping range, and the corresponding associated data.

FIG. 2 illustrates how a Key Search is performed over an Equivalent Non-overlapping Range Set and the Associated Data thereof.

Three different cases of searches are presented:

Case 1: Search is performed where the key K falls into an interval $\Gamma_{t-1} \leq K < \Gamma_t$. Since $\Gamma_{t-1}$ is a Closed Boundary, then $[\Gamma_{t-1}, \Gamma_t)$ is a Range. The result of this search is m="1" (Match), and $d = \delta_{t-1}$. It should be noted that since $\Gamma_t$ is a Closed Boundary, the interval at the right of $\Gamma_t$ is also a Range.

Case 2: Search is performed where the key K falls into an interval $\Gamma_{p+1} \leq K < \Gamma_{p+2}$. Since $\Gamma_{p+1}$ is an Open Boundary, then the interval)$\Gamma_{p+1}, \Gamma_{p+2}$[is not a Range. The result of this search is m="0" (No-Match) and d=x, where x means Don't Care.

Case 3: Search is performed where the key K falls into an interval $\Gamma_q \leq K < \Gamma_{q+1}$. Since $\Gamma_q$ is a Closed Boundary, then $[\Gamma_q, \Gamma_{q+1})$ is a Range. The result of this search is m="1" (Match), and $d = \delta_q$. Since $\Gamma_{q+1}$ is an Open Boundary, the interval at the right of $\Gamma_{q+1}$ is not a Range.

It may be concluded from the three cases presented above that the type of interval that contains the key K is a Range is solely determined by the interval left boundary. If this is a Closed Boundary, then the interval is a Range, there is a Match ($m_{interval}$="1") and there is a meaningful Associated Data $d_{interval}$ corresponding to this Range. If, however, the interval left boundary is an Open Boundary, then the interval is not a Range, and there is No-Match ($m_{interval}$="0") the Associated Data has no meaning.

Since the notion of the leftmost boundary of an interval that contains the key is used to determine whether the interval is a Range, a special care must be taken of the interval between 0 and $\Gamma_1$ (left boundary of the leftmost Range). If $\Gamma_1 > 0$, then the integer 0 must be denoted as an Open Boundary. This ensures that searching for a key in the interval)0, $\Gamma_1$[will yield No-Match.

1.4 Use of Non-Overlapping Ranges for Storing IPv4 CIDR Addresses

An IPv4 CIDR Address (which actually defines a range of addresses) consists of 32 bits. These 32-bit values are typically represented as four decimal values separated by dots, each representing an 8-bit binary number. The IPv4 CIDR address range is represented as:

A/p where A is the IPv4 address and p is the prefix ($0 \leq p \leq 32$).

The prefix is the number of contiguously compared most significant bits from left to right. The prefix is equivalent to a 32-bit mask consisting of p 1's followed by (32-p) 0's; each bit 0 in the mask of the CIDR address must be ignored when the address value is compared with a submitted address.

The IPv4 CIDR address range can be represented as a range using the following formula:

$$A/p = [A, A + 2^{32-p})$$

Comparing this formula with the range definition given above $R = [N_L, N_H)$, it is clear that the IPv4 CIDR address range parameters A and p are related to the range lower (closed) boundary $N_L$ and upper (open) boundary $N_H$ by simple formulae:

$N_L = A$ $N_H = A + 2^{32-p}$ $p = 32 - \log_2(N_H - N_L)$

EXAMPLE 1

The IPv4 CIDR address range 198.32.0.0/13 (in prefix representation) is alternatively represented by its IP Address and Mask as follows:

IP Address: 11000110 00100000 00000000 00000000
Mask: 11111111 11111000 00000000 00000000

This IP Address Range extends:

From: 11000110 00100000 00000000 00000000=198.32.0.0
To: 11000110 00100111 11111111 11111111= 198.39.255.255

By sharp contrast, the inventive Range Representation, compactly specifies the IP Address Range as follows:

[11000110 00100000 00000000 00000000, 11000110 00101000 00000000 00000000)=[198.32.0.0, 198.40.0.0)

IPv4 CIDR address ranges are characterized in that smaller ranges have higher priority and are thus contained in larger ranges; i.e., if $R_a \equiv A_a/p_a$ and $R_b \equiv A_b/p_b$ are two IPv4 CIDR overlapping address ranges, where $p_a > p_b$ (a<b), then $R_a \equiv A_a/p_a \subset R_b \equiv A_b/p_b$, as shown in FIG. 1(b). IPv4 CIDR address ranges can also be non-overlapping, as in FIG. 1(a), but cannot be partially overlapping as in FIG. 1(c) or FIG. 1(d). The case shown in FIG. 1(e), where the larger range $R_b$ has higher priority than $R_a$, is not possible either.

If $R_a \subseteq R_b$, as shown in FIG. 1(b), then $R_a$ is left unchanged after the $R_{a \cup R_b}$ operation, and the ranges $[N_L{}^a, N_L{}^b)/d_b$ and $[N_H{}^a, N_H{}^b)/d_b$ are created; both ranges have the priority of $R_b$, which is lower than that of $R_a$.

The IPv4 CIDR address ranges are pre-processed using the U operator until yielding equivalent non-overlapping ranges for storage as sequential keys in the Key TDA of a RAM-Based RCAM. When a new IPv4 CIDR address range is inserted, it is processed with the already stored non-overlapping ranges within its boundaries only, because larger ranges outside them have lower priority and are not affected. Similarly, when an enlisted address range is removed, the remaining ranges within its boundaries are processed before their storage.

IPv4 CIDR addresses can always be represented by ranges, but not all the ranges can have equivalent CIDR addresses. However, CIDR addresses can be aggregated to form any range. The inventive Range Representation allows aggregation of contiguous CIDR address ranges into a single range defined by just two numbers, i.e., the lower and upper boundaries of the range.

Figure 3:
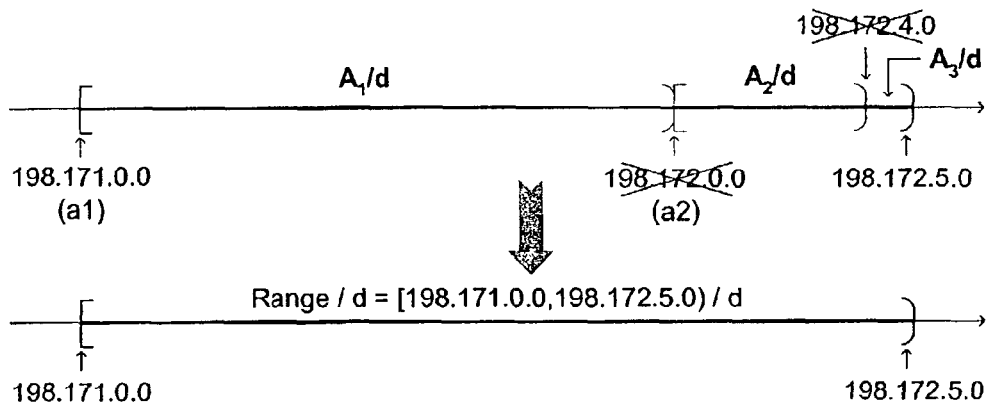
FIG. 3 is an exemplary aggregation of three contiguous CIDR addresses according to a range representation of the present invention.

FIG. 3 shows an example of the aggregation of three contiguous CIDR address ranges leading to a single range defined by these two boundaries, in contrast to the conventional prefix notation requiring three pairs of numbers.

Another simple example of the advantage of the inventive Range Representation over the prefix notation is the specification of the CIDR address ranges containing all the client TCP ports greater than 1023.

The inventive Range Representation requires only one range specified by the lower and upper boundaries thereof, i.e., [00000100 00000000, 00000000 00000000).

The conventional prefix notation, on the other hand, requires six pairs of numbers:

| | | | |
|---|---|---|---|
| SPN$_1$: | 00000100 00000000 | SPN$_4$: | 00100000 00000000 |
| Mask$_1$: | 11111100 00000000 | Mask$_4$: | 11100000 00000000 |
| SPN$_2$: | 00001000 00000000 | SPN$_5$: | 01000000 00000000 |
| Mask$_2$: | 11111000 00000000 | Mask$_5$: | 11000000 00000000 |
| SPN$_3$: | 00010000 00000000 | SPN$_6$: | 10000000 00000000 |
| Mask$_3$: | 11110000 00000000 | Mask$_6$: | 10000000 00000000 | where SPN stands for Source Port Number

2. Multi-Dimensional Ranges—Basic Principles 2.1 Definitions

Definition: $\Omega^d$ is a d-Dimensional Space if it contains all the d-dimensional points $P \equiv (x_0^*, x_1^*, \ldots x_{d-1}^*)$, where $x_i^*$ is an integer coordinate in the $X_i$ dimension, and i is an integer $0 \leq i < d$.

Definition: Let $\Omega^d$ be a d-dimensional space with $X_0, X_1, \ldots, X_{d-1}$ dimension coordinates.

$\Re^d \equiv \Re_0{}^1 X \Re_1{}^1 X \ldots X \Re_{d-1}{}^1$, a d-Dimensional Range in $\Omega^d$, is a set of all d-dimensional integer points $P \equiv (x_0^*, x_1^*, \ldots x_{d-1}^*)$ such that $x_i^* \in \Re_i{}^1$ for $0 \leq i < d$, where $\Re_i{}^1$ is a one-dimensional range in the i-th dimension; $\Re_i{}^1 \equiv [x_L{}^i, x_H{}^i)$, where $x_L{}^i$ is the lower closed boundary and $x_H{}^i$ is the upper open boundary of $\Re_i{}^1$, i.e., $x_L{}^i \leq x_i^* < x_H{}^i$.

Figure 4:
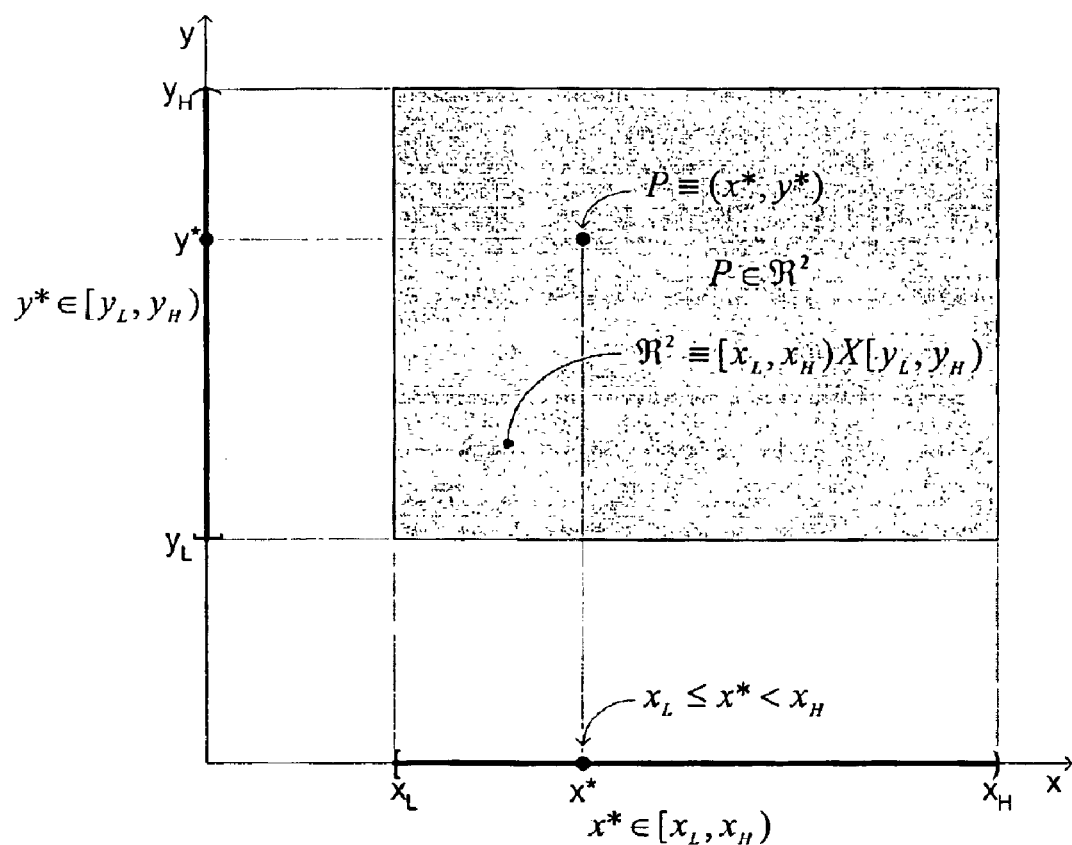
FIG. 4 is a Two-Dimensional Range Representation $\Re^2$.

FIG. 4 depicts a two-dimensional range representation, $\Re^2$, which conforms to this definition. A two-dimensional range $\Re^2$ is represented by a rectangle in a two-dimensional space $\Omega^2$. This rectangle contains all the two-dimensional integer points $P \equiv (x^*, y^*)$ such that $x^* \in [x_L, x_H)$ and $y^* \in [y_L, y_H)$, where $[x_L, x_H)$ and $[y_L, y_H)$ are one-dimensional ranges in the x and y dimensions, respectively.

Figure 5:
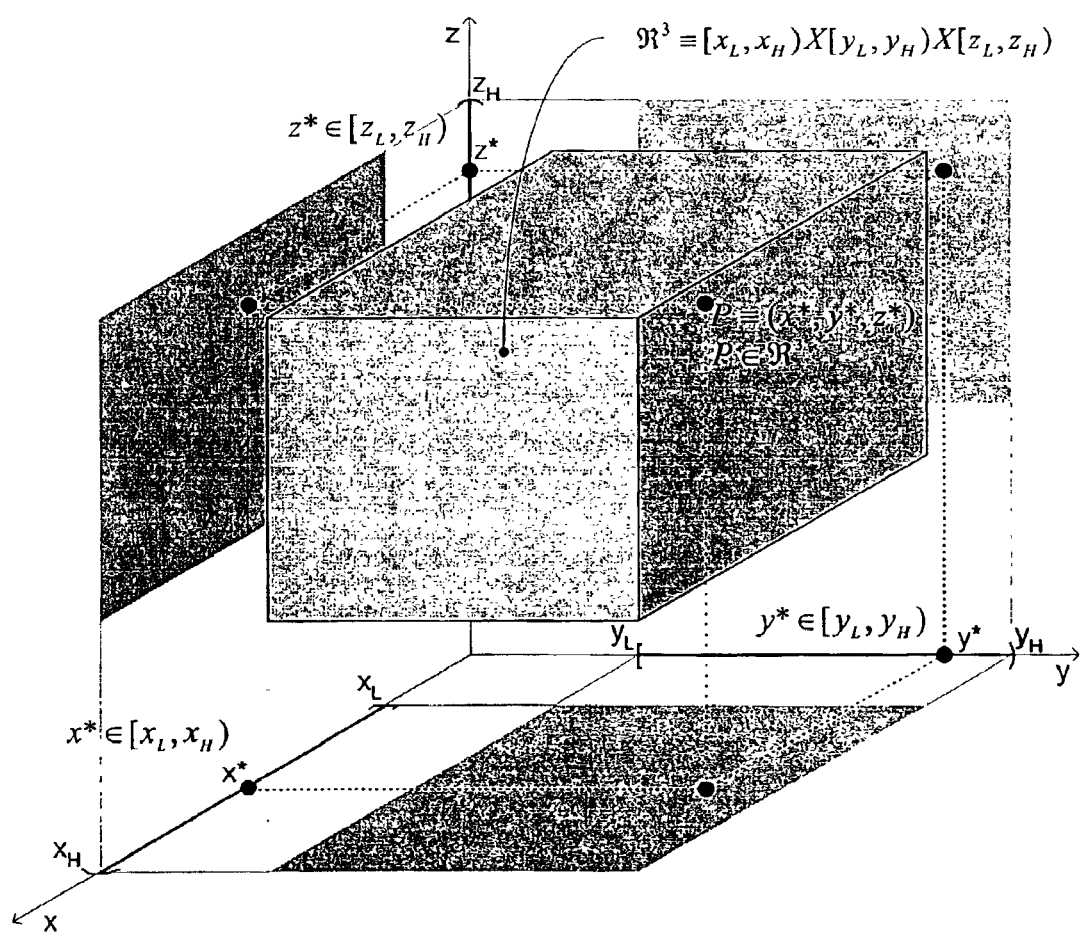
FIG. 5 is a Three-Dimensional Range Representation $\Re^3$.

FIG. 5 shows an example of a three-dimensional range. A three-dimensional range $\Re^3$ can be geometrically represented by a rectangular parallelepiped. Similarly, a d-dimensional range can be considered as a d-dimensional rectangular parallelepiped.

Definition: $\Phi^d$ is an Empty d-Dimensional Range, if a d-dimensional point $P \equiv (x_0^*, x_1^*, \ldots x_{d-1}^*)$, $P \in \Omega^d$, and $P \notin \Phi^d$.

Theorem: The $\Phi^d$ projection in each dimension is a one-dimensional range $\Phi_i{}^1$, $0 \leq i < d$.

Definition: $\Re_1{}^d$ is a Sub-Range of $\Re_2{}^d$ if for every $P \equiv (x_0^*, x_1^*, \ldots x_{d-1}^*)$, such that $P \in \Re_1{}^d \rightarrow P \in \Re_2{}^d$.

Definition: $\Re_1{}^d$ is a Proper Sub-Range of $\Re_2{}^d$ if $\Re_1{}^d$ is a Sub-Range of $\Re_2{}^d$ and there is $P_2 \equiv (x_0^*, x_1^*, \ldots x_{d-1}^*)$, such that $P_2 \in \Re_2{}^d$ and $P_2 \notin \Re_1{}^d$.

Figure 6:
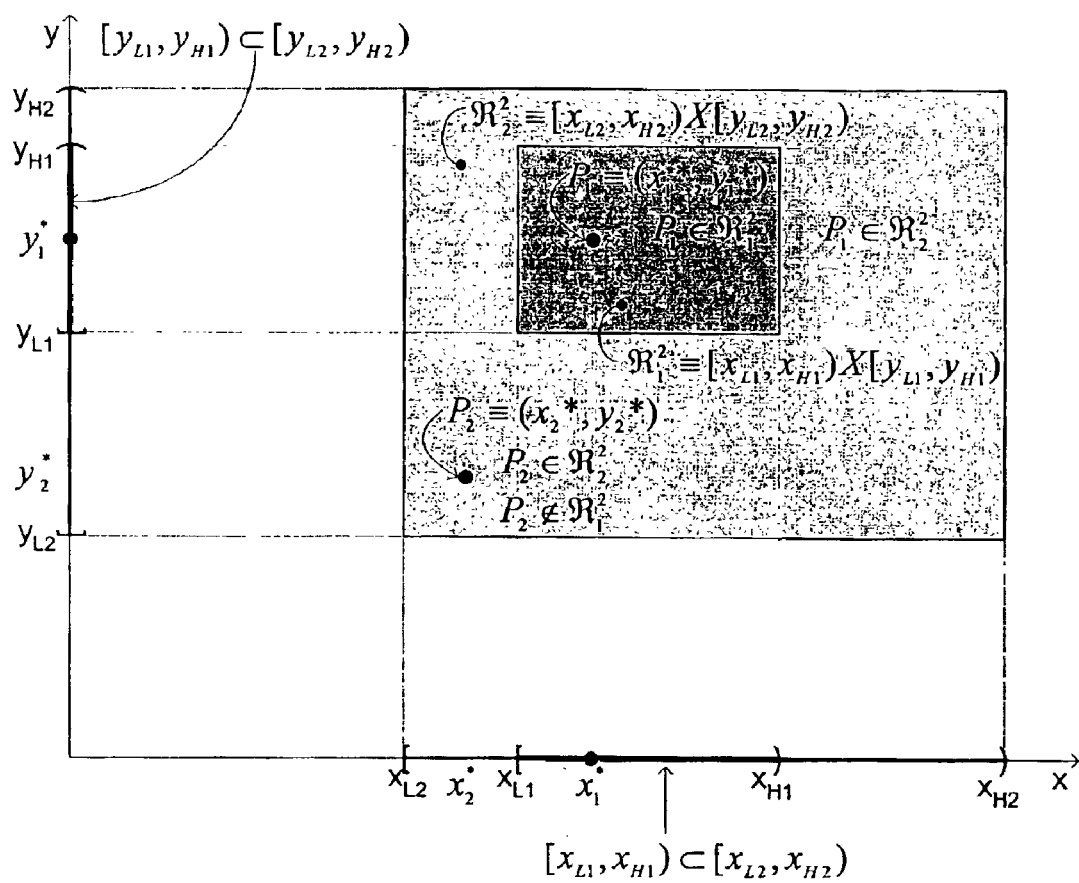
FIG. 6 is a Proper Two-Dimensional Sub-Range of a Two-Dimensional Range.

FIG. 6 depicts a Proper Two-Dimensional Sub-Range of a Two-Dimensional Range.

Definition: Multi-dimensional Ranges $\Re_1{}^d$ $\Re_2{}^d$ are Overlapping if there is a d-dimensional point $P \equiv (x_0^*, x_1^*, \ldots x_{d-1}^*)$ such that $P \in \Re_1{}^d$ and $P \in \Re_2{}^d$.

Theorem: $\Re_1{}^d$ and $\Re_2{}^d$ are Overlapping Multi-Dimensional Ranges, $\Re_{i1}{}^1 \equiv [x_{L1}{}^i, x_{H1}{}^i)$ is the $\Re_1{}^d$ range projection on the i-th dimension axis, and $\Re_{i2}{}^1 \equiv [x_{L2}{}^i, x_{H2}{}^i)$ is the $\Re_2{}^d$ range projection on the i-th dimension axis, for $0 \leq i < d$. Then, $\Re_{i1}{}^1$ and $\Re_{i2}{}^1$ are Overlapping Ranges for $0 \leq i < d$.

Figure 7:
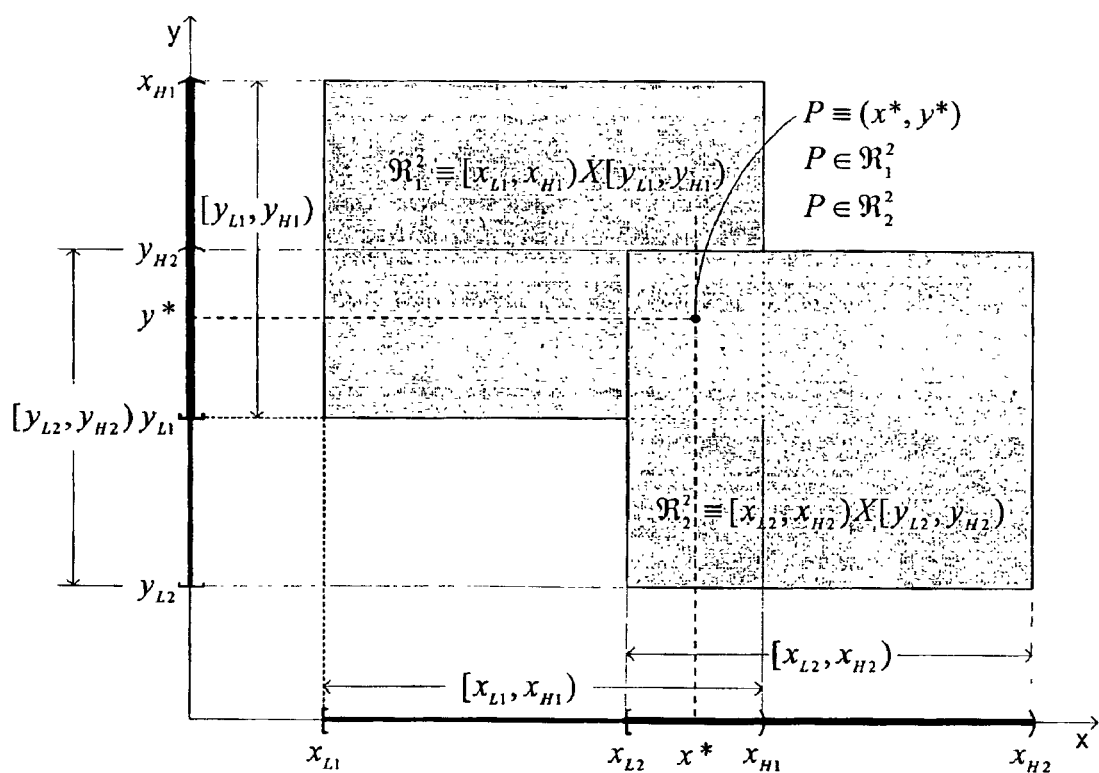
FIG. 7 illustrates Overlapping Two-Dimensional Ranges.

FIG. 7 demonstrates two-dimensional Overlapping Ranges. For the two-dimensional overlapping ranges $\Re_1{}^2$ and $\Re_2{}^2$, $[x_{L1}, x_{H1})$ and $[x_{L2}, x_{H2})$, and also $[y_{L1}, y_{H1})$ and $[y_{L2}, y_{H2})$, are overlapping.

Definition: Multi-dimensional Ranges $\Re_1{}^d$ and $\Re_2{}^d$ are Disjoint (or Non-Overlapping) if for any d-dimensional point $P \equiv (x_0^*, x_1^*, \ldots x_{d-1}^*)$, $P \in \Re_1{}^d \rightarrow P \notin \Re_2{}^d$ and $P \in \Re_2{}^d \rightarrow P \notin \Re_1{}^d$.

Theorem: $\Re_1{}^d$, and $\Re_2{}^d$ are Disjoint Multi-Dimensional Ranges, if there exists an i-th dimension $0 \leq i < d$ for which the one-dimensional range projections $\Re_{i1}{}^1 \equiv [x_{L1}{}^i, x_{H1}{}^i)$ and $\Re_{i2}{}^1 \equiv [x_{L2}{}^i, x_{H2}{}^i)$ are Disjoint.

Figure 8:
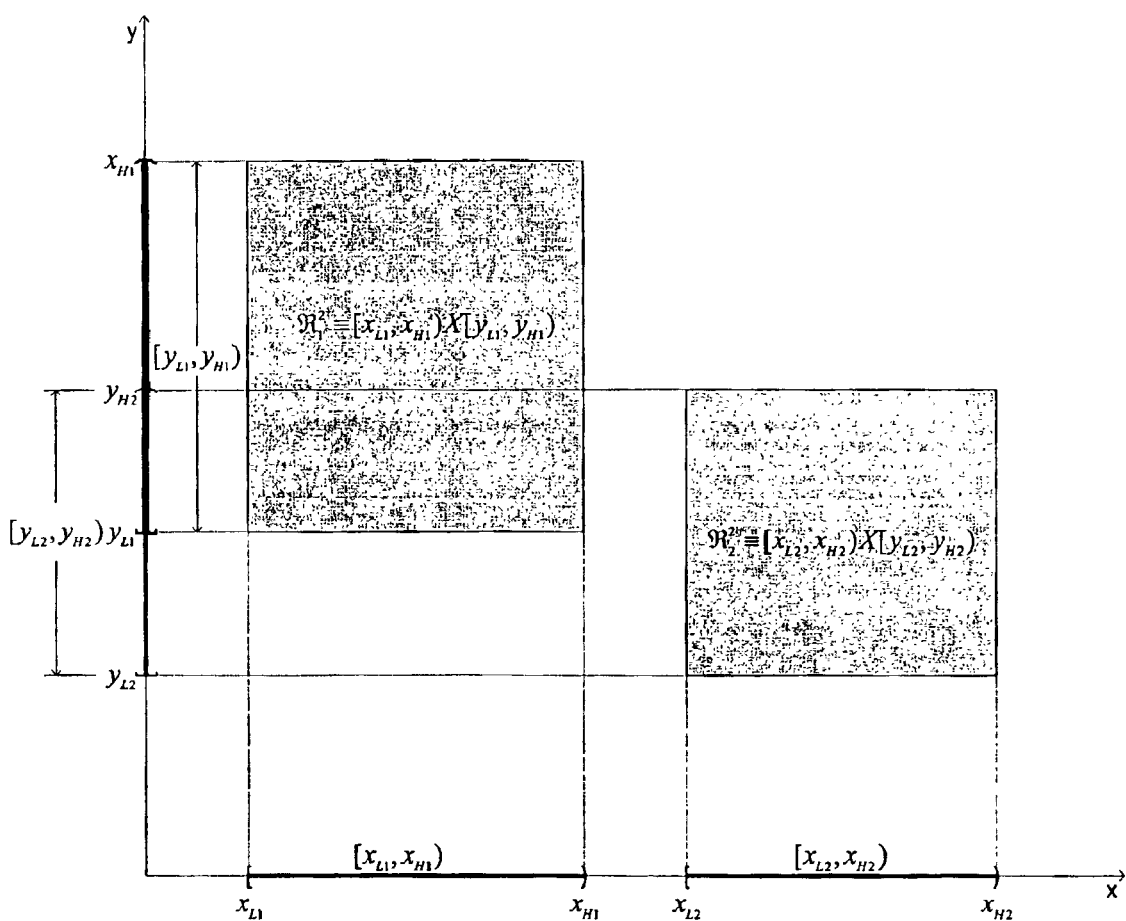
FIG. 8 illustrates Disjoint Two-Dimensional Ranges.

FIG. 8 demonstrates two-dimensional Disjoint Ranges. The ranges are disjoint because their projected ranges on the x-axis, $[x_{L1}, x_{H1})$ and $[x_{L2}, x_{H2})$, are disjoint. Similarly, if the projected one-dimensional ranges on the y-axis are disjoint, then also the two-dimensional ranges are disjoint.

Definition: The Inverse of a Range $\Re^d \equiv [x_L{}^0, x_H{}^0) X [x_L{}^1, x_H{}^1) X \ldots X [x_L{}^{d-1}, x_H{}^{d-1})$ is a range $$\overline{R^d} \equiv \overline{[x_L^0, x_H^0) X [x_L^1, x_H^1) X \ldots X [x_L^{d-1}, x_H^{d-1})}$$

defined as a set of all points $P \equiv (x_0^*, x_1^*, \ldots x_{d-1}^*)$, such that if $P \in \overline{\Re^d} \rightarrow P \notin \Re^d$.

Theorem: Let $\Re^d \equiv [x_L{}^0, x_H{}^0) X [x_L{}^1, x_H{}^1) X \ldots X [x_L{}^{d-1}, x_H{}^{d-1})$ be a d-dimensional range.

Then, $\overline{\Re^d} \equiv \{[0, x_L{}^0) + [x_H{}^0, 0)\} + \{[0, x_L{}^1) + [x_H{}^1, 0)\} + \ldots + \{[0, x_L{}^{d-1}) + [x_H{}^{d-1}, 0)\}$.

Figure 9:
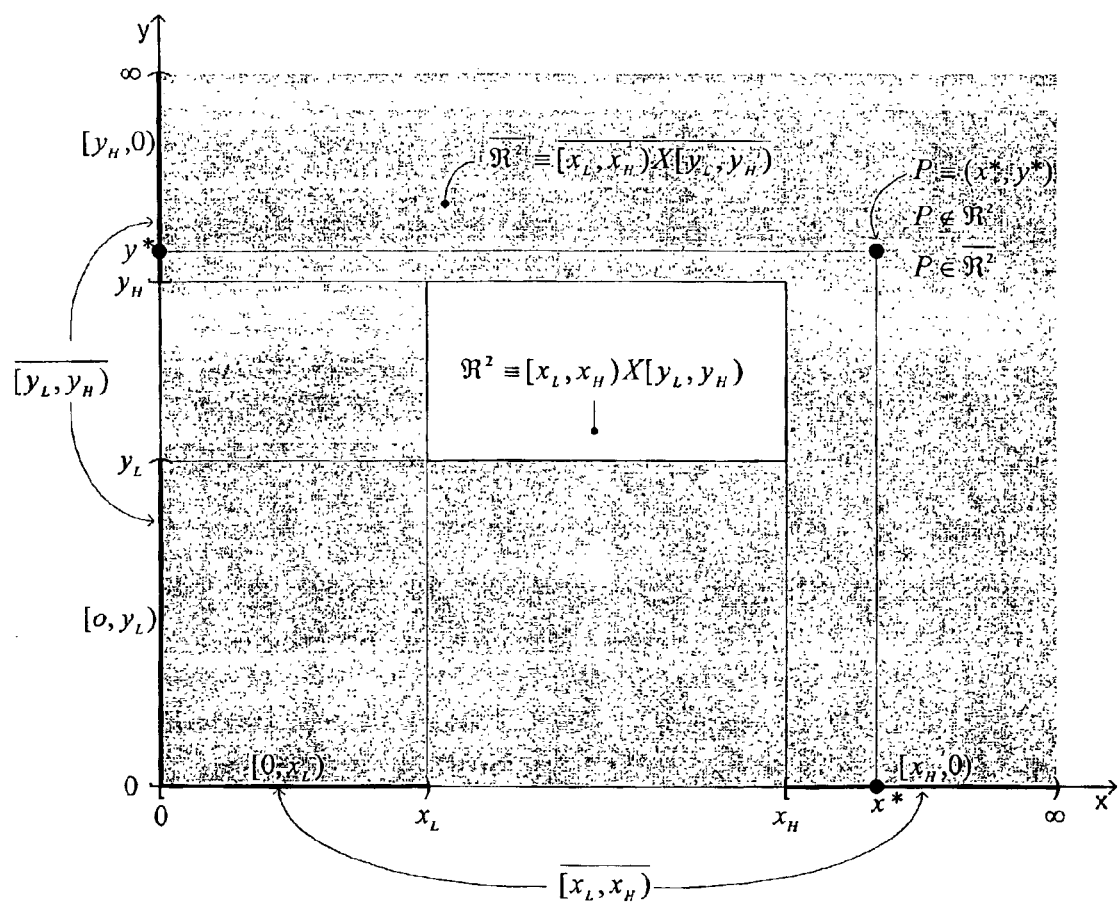
FIG. 9 shows a Two-Dimensional Inverse of a Range.

FIG. 9 depicts a two-dimensional Inverse of the range
$$\overline{\mathfrak{R}^2} = \overline{[x_L, x_H) X [y_L, y_H)}$$

Note: Zero used as the range upper limit implies that this range extends indefinitely. In a set of k-bit numbers, the largest number has k '1's. The next larger number is '1' in the (k+1)th-bit position followed by k '0's. So, if this bit '1' is omitted, then the string of k '0's can be used as a number larger than all k-bit numbers. Since this zero always follows the largest number in the set, it can be clearly distinguished from the string of k '0's (true zero) used as the range lower limit.

2.2 Multi-Dimensional Ranges—Basic Laws

Since Multi-Dimensional Ranges are groups, all the logic relations that apply to groups also apply to ranges.

In the relations brought hereinbelow,
- + is an "OR" operator between two d-dimensional ranges.
- • is an "AND" operator between two d-dimensional ranges.

Definition: If $P \in \mathfrak{R}_1^d + \mathfrak{R}_2^d \rightarrow (P \in \mathfrak{R}_1^d) \text{OR} (P \in \mathfrak{R}_2^d)$
Definition: If $P \in \mathfrak{R}_1^d \bullet \mathfrak{R}_2^d \rightarrow (P \in \mathfrak{R}_1^d) \text{AND} (P \in \mathfrak{R}_2^d)$ Identity Laws:
$\mathfrak{R}^d + \Phi^d = \mathfrak{R}_d$
$\mathfrak{R}^d \bullet \Omega^d = \mathfrak{R}^d$ Commutative Laws:
$\mathfrak{R}_1^d + \mathfrak{R}_2^d = \mathfrak{R}_2^d + \mathfrak{R}_1^d$
$\mathfrak{R}_1^d \bullet \mathfrak{R}_2^d = \mathfrak{R}_2^d \bullet \mathfrak{R}_1^d$ Complementation Law:
$\overline{\overline{\mathfrak{R}^d}} = \mathfrak{R}^d$ Associative Laws:
$\mathfrak{R}_1^d + (\mathfrak{R}_2^d + \mathfrak{R}_3^d) = (\mathfrak{R}_1^d + \mathfrak{R}_2^d) + \mathfrak{R}_3^d$
$\mathfrak{R}_1^d \bullet (\mathfrak{R}_2^d \bullet \mathfrak{R}_3^d) = (\mathfrak{R}_1^d \bullet \mathfrak{R}_2^d) \bullet \mathfrak{R}_3^d$ Distributive Laws:
$\mathfrak{R}_1^d \bullet (\mathfrak{R}_2^d + \mathfrak{R}_3^d) = \mathfrak{R}_1^d \bullet \mathfrak{R}_2^d + \mathfrak{R}_1^d \bullet \mathfrak{R}_3^d$
$\mathfrak{R}_1^d + (\mathfrak{R}_2^d \bullet \mathfrak{R}_3^d) = (\mathfrak{R}_1^d + \mathfrak{R}_2^d) \bullet (\mathfrak{R}_1^d + \mathfrak{R}_3^d)$ De Morgan Laws:
$\overline{\mathfrak{R}_1^d + \mathfrak{R}_2^d} = \overline{\mathfrak{R}_1^d} \bullet \overline{\mathfrak{R}_2^d}$
$\overline{\mathfrak{R}_1^d \bullet \mathfrak{R}_2^d} = \overline{\mathfrak{R}_1^d} + \overline{\mathfrak{R}_2^d}$

2.3 Multi-Dimensional Range-Specific Laws

Operations can be performed on Multi-Dimensional Ranges by performing operations in one dimension, followed by operations in another dimension, and so on.

Identity Laws:
$[x_L, x_H) X ([y_L, y_H) + \Phi_y^2) = [x_L, x_H) X [y_L, y_H)$
$([x_L, x_H) + \Phi_x^2) X [y_L, y_H) = [x_L, x_H) X [y_L, y_H)$
$[x_L, x_H) X ([y_L, y_H) \bullet \Omega_y^2) = [x_L, x_H) X [y_L, y_H)$
$([x_L, x_H) \bullet \Omega_x^2) X [y_L, y_H) = [x_L, x_H) X [y_L, y_H)$ $\Phi_x^2$ and $\Phi_y^2$ are empty one-dimensional ranges in the x and y directions, respectively.
$\Omega_x^2$ and $\Omega_y^2$ are the entire one-dimensional range spaces in the x and y directions, respectively.

Figure 10:
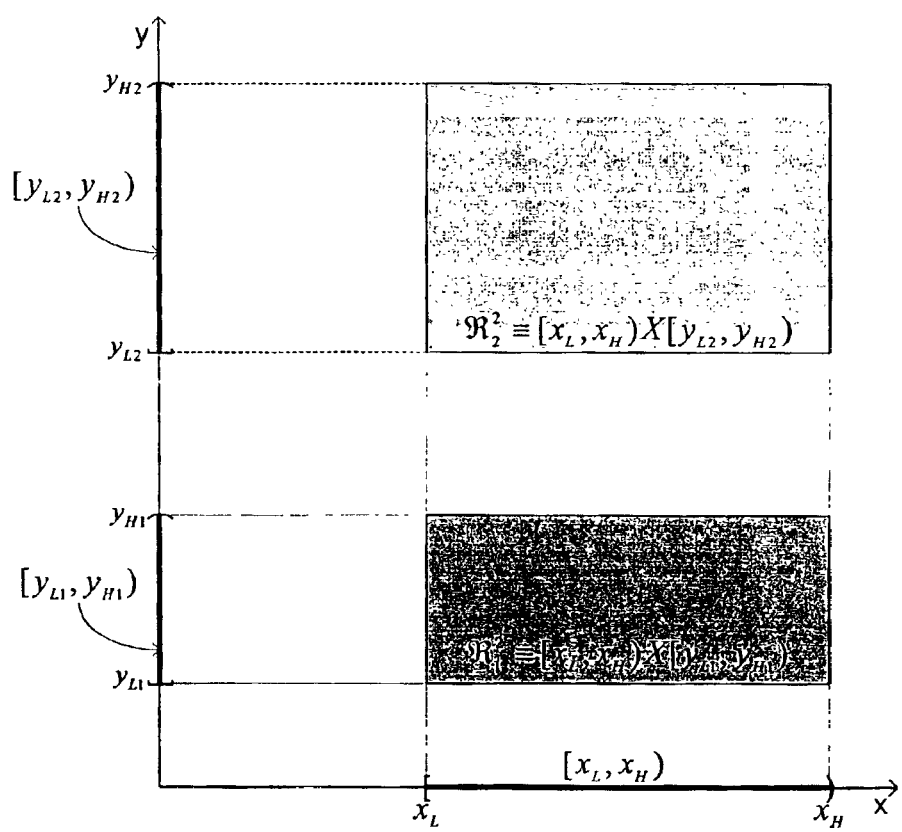
FIG. 10 provides a Graphical Demonstration of the First Distributive Law.
Figure 11:
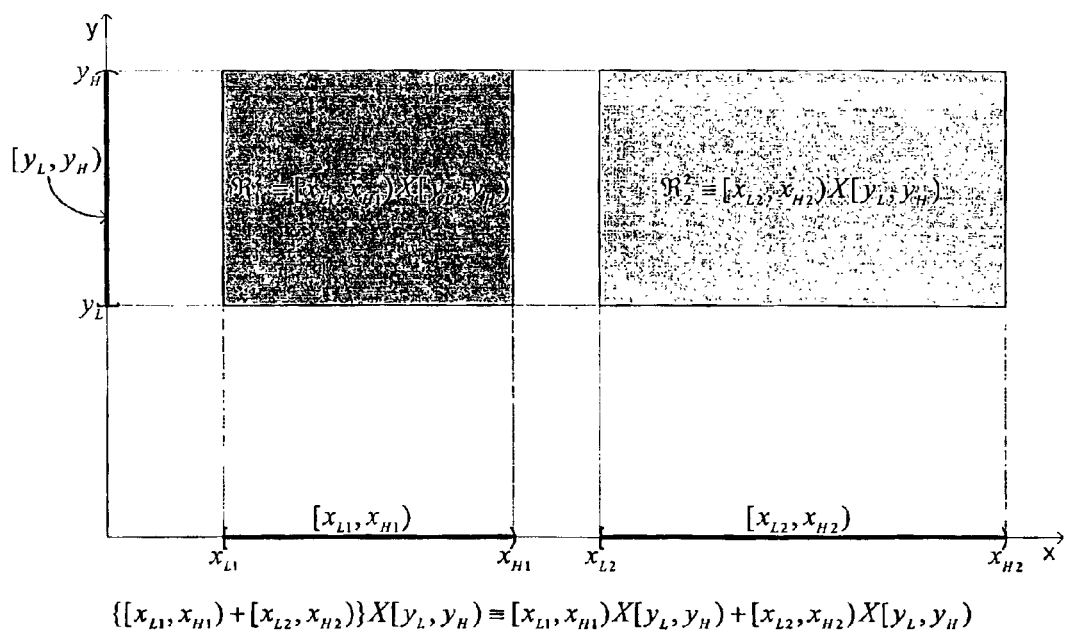
FIG. 11 provides a Graphical Demonstration of the Second Distributive Law.

Complementation Law:
$\overline{\overline{[x_L, x_H) X [y_L, y_H)}} = [x_L, x_H) X [y_L, y_H)$ Commutative Law:
$[x_L, x_H) X [y_L, y_H) = [y_L, y_H) X [x_L, x_H)$ Associative Law:
$[x_L, x_H) X \{[y_L, y_H) X [z_L, z_H)\} = \{[x_L, x_H) X [y_L, y_H)\} X [z_L, z_H)$ Distributive Laws:
$[x_L, x_H) X \{[y_{L1}, y_{H1}) + [y_{L2}, y_{H2})\} = [x_L, x_H) X [y_{L1}, y_{H1}) + [x_L, x_H) X [y_{L2}, y_{H2})$
$\{[x_{L1}, x_{H1}) + [x_{L2}, x_{H2})\} X [y_L, y_H) = [x_{L1}, x_{H1}) X [y_L, y_H) + [x_{L2}, x_{H2}) X [y_L, y_H)$ The meaning of the two distributive laws is graphically depicted in FIGS. 10 and 11.

Figure 12:
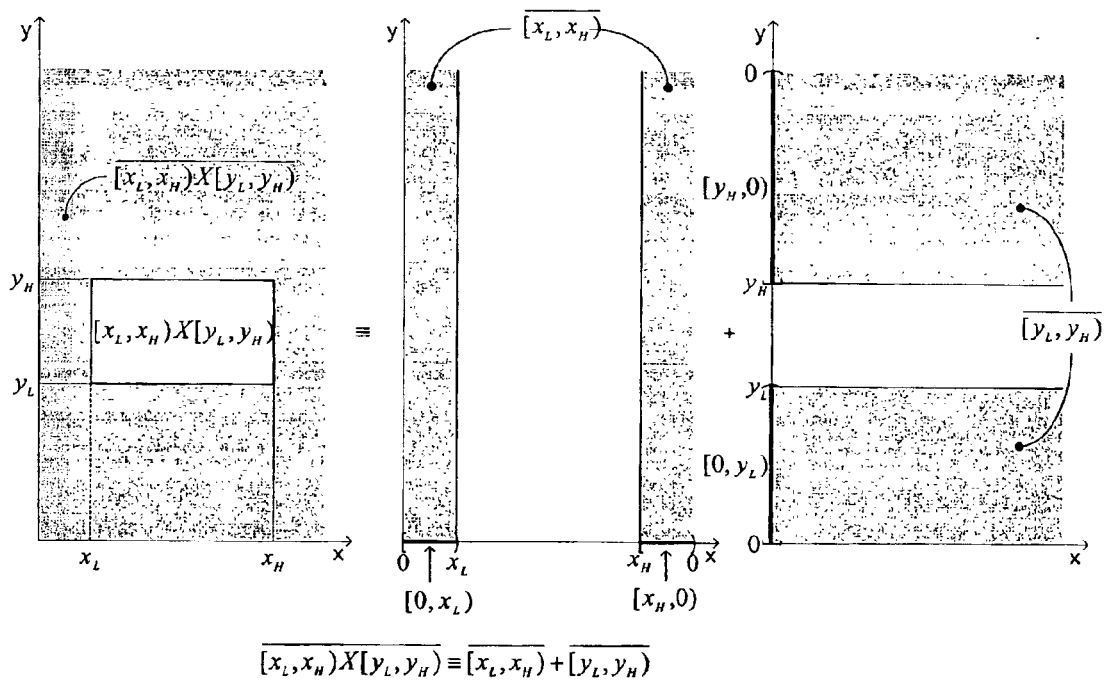
FIG. 12 is a Graphical Demonstration of the First "De Morgan" Law for a Two-Dimensional Range.
Figure 13:
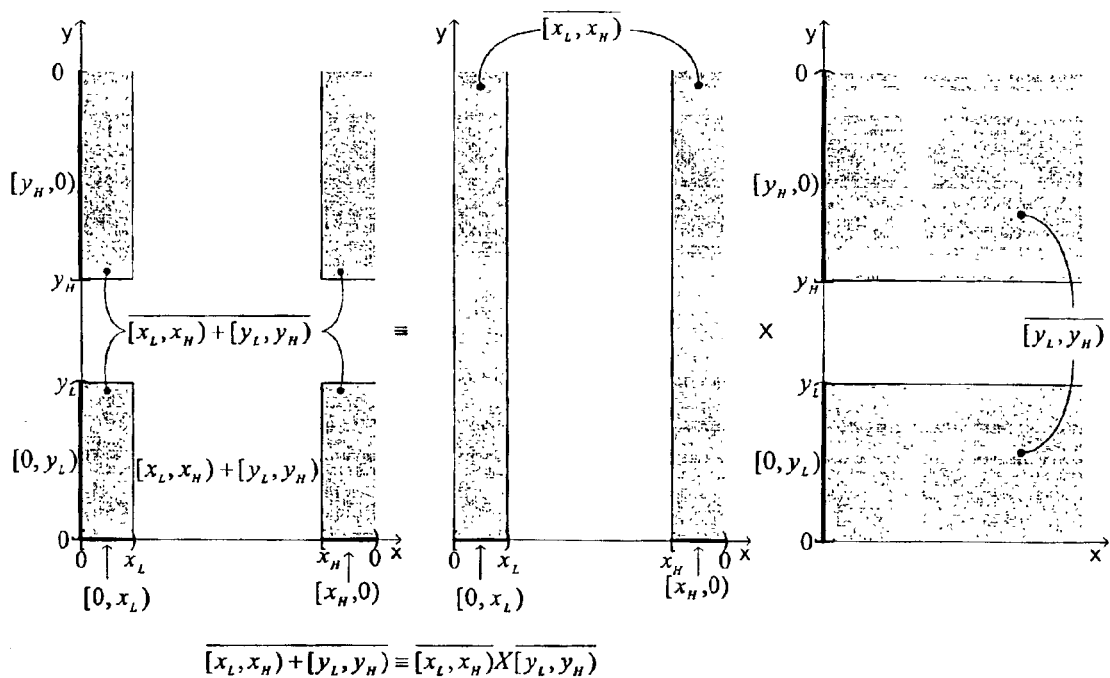
FIG. 13 is a Graphical Demonstration of the Second "De Morgan" Law for a Two-Dimensional Range.

"De Morgan" Laws:

The laws formulated hereinbelow are similar to the De Morgan laws, applied to two-dimensional ranges.
$\overline{[x_L, x_H) X [y_L, x_H)} = \overline{[x_L, x_H)} + \overline{[y_L, y_H)}$
$\overline{[x_L, x_H) + [y_L, y_H)} = \overline{[x_L, x_H)} X \overline{[y_L, y_H)}$ FIG. 12 and FIG. 13 demonstrate the two De Morgan-type laws for two-dimensional ranges.

2.4 Multi-Dimensional Ranges, Associated Actions and Priorities

Definition:
Let $K^d$ be a d-dimensional value $K^d \equiv (k_0, k_1, \ldots k_{d-1})$ defined as a Key.

Let $\{\mathfrak{R}_0^d, \mathfrak{R}_1^d, \ldots \mathfrak{R}_{n-2}^d, \mathfrak{R}_{n-1}^d\}$ be a set of n disjoint ranges.

Let $\{A_0 A_1, \ldots A_{n-2}, A_{n-1}\}$ be a set of actions associated with the set of the disjoint ranges, that is, $A_i$ is associated with $\mathfrak{R}_i^d$ for $0 \leq i < n$.

Let $\{m_0, m_1, \ldots m_{n-2}, m_{n-1}\}$ be a set of the respective matching logic values of the disjoint ranges, such that, if $K^d \in \mathfrak{R}_j^d \rightarrow m_j = '1'$, otherwise $m_i = '0'$ for $0 \leq i < n$ and $i \neq J$.

Then, $(A, m) = \aleph(\{\mathfrak{R}_0^d, \mathfrak{R}_1^d, \ldots \mathfrak{R}_{n-1}^d\}, K^d)$ is an associated action function, such that $A = A_j$ and $m = '1'$ if $m_j = '1'$. If $m_i = '0'$ for any i, $0 \leq i < n$, then A is underlined and $m = '0'$.

From here and on, we shall apply the notation $\mathfrak{R}_i^d / A_i$ to denote an action $A_i$ associated with the d-dimensional range $\mathfrak{R}_i^d$.

The definition provided hereinabove is valid for disjoint ranges. However, in the general case, the multi-dimensional ranges may be overlapping; that is, there exists $P = (x_0^*, x_1^*, \ldots x_{d-1})$, such that $P \in \mathfrak{R}_i^d / A_i$ and $P \in \mathfrak{R}_j^d / A_j$, $A_i \neq A_j$, $i \neq j$, $0 \leq i < n$, $0 \leq j < n$. Thus, there may be Keys, which when applied to the set of ranges $\{\mathfrak{R}_0^d / A_0, \mathfrak{R}_1^d / A_1, \ldots, \mathfrak{R}_{n-1}^d / A_{n-1}\}$ may yield two conflicting actions $A_i \neq A_j$.

The notion of priority resolves any conflicts.

Definition: Let $\mathfrak{R}_i^d / A_i / p_i$ be a range $\mathfrak{R}_i^d$, an action $A_i$ and an integer $p_i$, where $p_i \geq 0$ is defined as the priority of the range $\mathfrak{R}_i^d$; $p_i \neq p_j$ for any two overlapping ranges $\mathfrak{R}_i^d$ and $\mathfrak{R}_j^d$. $\mathfrak{R}_i^d$ is defined as having higher priority than $\mathfrak{R}_j^d$ for $p_i < p_j$.

Note: The definition that $\mathfrak{R}_i^d$ is of higher priority than $\mathfrak{R}_j^d$ if $p_i < p_j$ is arbitrary. $\mathfrak{R}_i^d$ can be defined as having lower priority than $\mathfrak{R}_j^d$ if $p_i < p_j$.

Definition:
Let $\mathfrak{R}_1^d / A_1 / p_1$ be a range $\mathfrak{R}_1^d$, an action $A_1$ and an integer $p_1, p_1 \geq 0$, and $\mathfrak{R}_2^d / A_2 / p_2$ be a range $\mathfrak{R}_2^d$, an action $A_2$ and an integer $p_2, p_2 \geq 0$, such that $p_1 < p_2$ for any two overlapping ranges $\mathfrak{R}_1^d$ and $\mathfrak{R}_2^d$; $p_1$ and $p_2$ are defined as the respective priorities of the d-dimensional ranges $\mathfrak{R}_1^d$ and $\mathfrak{R}_2^d$. If $K^d \in \mathfrak{R}_1^d / A_1 / p_1$, $K^d \in \mathfrak{R}_2^d / A_2 / p_2$, where $p_1 < p_2$, and $(A, '1') = \aleph(\{\mathfrak{R}_1^d / A_1 / p_1, \mathfrak{R}_2^d / A_2 / p_2\})$, then $A = A_1$ and $m = '1'$.

Figure 14:
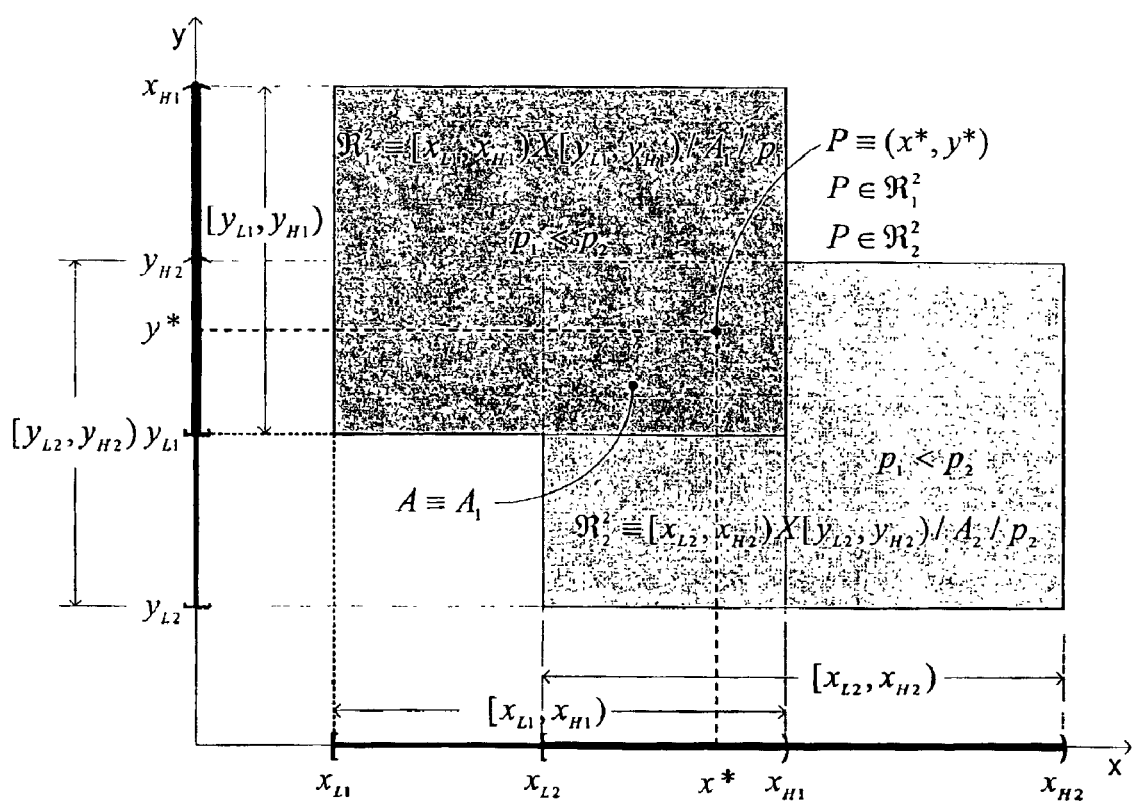
FIG. 14 is a Graphical Demonstration of Priority Definition to Resolve Any Conflict Between Overlapping d-Dimensional Ranges.

This definition resolves any conflict between overlapping d-dimensional ranges in the overlapping regions. This is demonstrated for the case of overlapping two-dimensional ranges in FIG. 14. As shown in FIG. 14, since $\mathfrak{R}_1^d$ has higher priority than $\mathfrak{R}_2^d$ ($p_1 < p_2$), then the action taken on $K^d \in \mathfrak{R}_1^d$ and $K^d \in \mathfrak{R}_2^d$ is $A_1$.

A set of laws can be defined, accounting for overlapping ranges, actions and priorities:

Identity Laws:
$[x_L, x_H) X ([y_L, y_H) + \Phi hd\ y^2) / A / p = [x_L, x_H) X [y_L, y_H) / A / p$ $([x_L,x_H]+\Phi_x^2)X[y_L,y_H]/A/p \equiv [x_L,x_H]X[y_L,y_H]/A/p$
$[x_L,x_H]X([y_L,y_H]\cdot\Omega_y^2)/A/p \equiv [x_L,x_H]X[y_L,y_H]/A/p$
$([x_L,x_H]\cdot\Omega_x^2)X[y_L,y_H]/A/p \equiv [x_L,x_H]X[y_L,y_H]/A/p$ Complementation Law:

$\overline{\overline{[x_L,x_H]}}X[y_1,y_H]/A/p \equiv [x_L,x_H]X[y_1,y_H]/A/p$

Commutative Law:

$[x_L,x_H]X[y_L,y_H]/A/p \equiv [y_L,y_H]X[x_L,x_H]/A/p$

Associative Law:

$[x_L,x_H]X\{[y_L,y_H]/A/p\} \equiv \{[x_L,x_H]/A/p\}X[y_L,y_H]$

Figure 15:
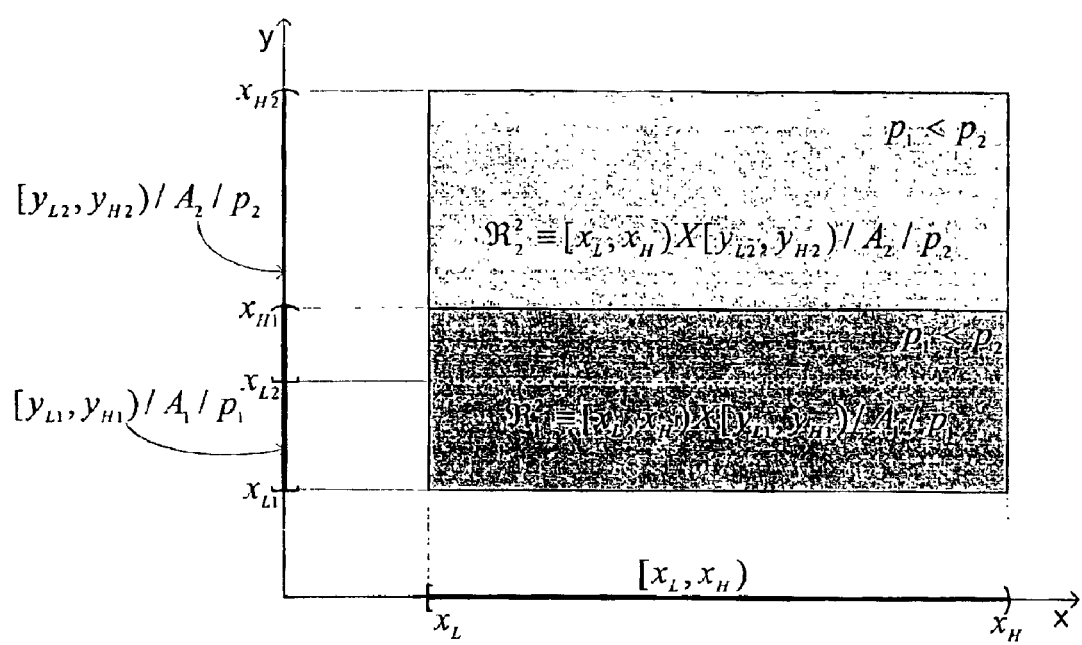
FIG. 15 provides a Graphical Demonstration of the First Distributive Law for Two-Dimensional Overlapping Ranges.
Figure 16:
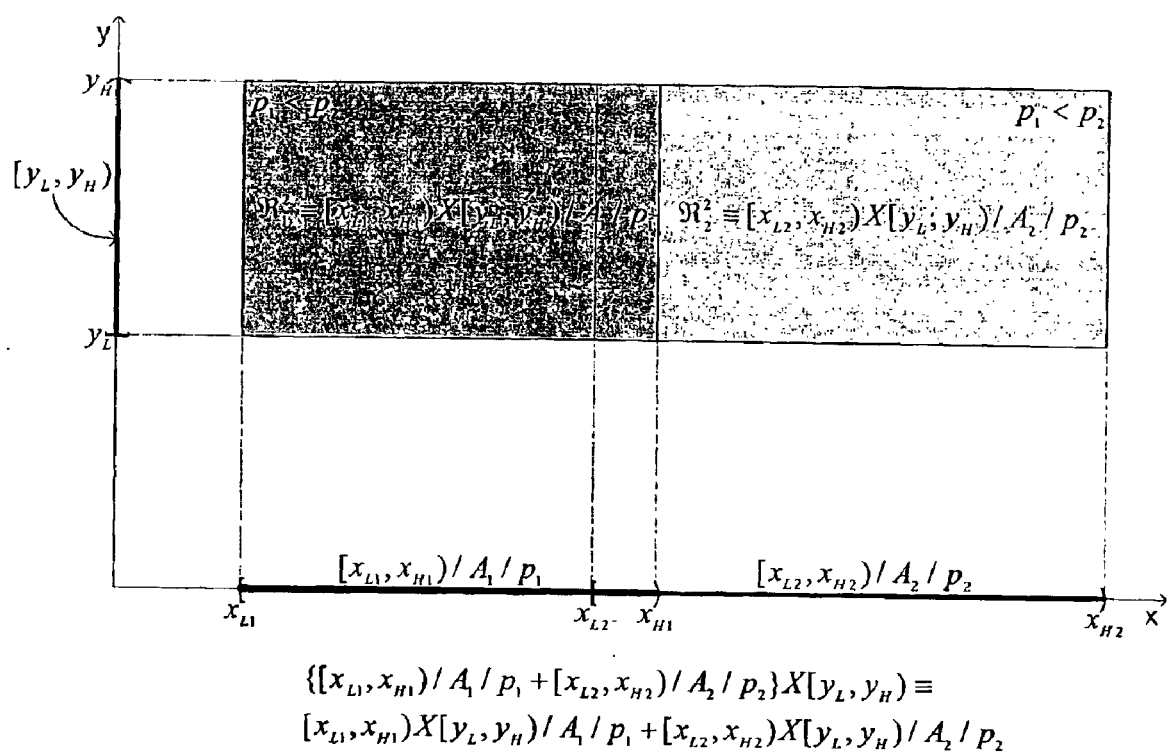
FIG. 16 provides a Graphical Demonstration of the Second Distributive Law for Two-Dimensional Overlapping Ranges.

Distributive Laws:

$[x_L,x_H]X\{[y_{L1},y_{H1}]/A_1/p_1+[y_{L2},y_{H2}]/A_2/p_2\} \equiv [x_L,x_H]X[y_{L1},y_{H1}]/A_1/p_1+[x_L,x_H]X[y_{L2},y_{H2}]/A_2/p_2$ $\{[x_{L1},x_{H1}]/A_1/p_1+[x_{L2},x_{H2}]/A_2/p_2\}X[y_L,y_H] \equiv [x_{L1},x_{H1}]X[y_L,y_H]/A_1/p_1+[x_{L2},x_{H2}]X[y_L,y_H]/A_2/p_2$ The distributive laws are depicted in FIGS. 15 and 16 for the two-dimensional overlapping range case.

"De Morgan" Laws:

The laws provided hereinbelow are similar to the De Morgan laws, applied to two-dimensional ranges.

Figure 17:
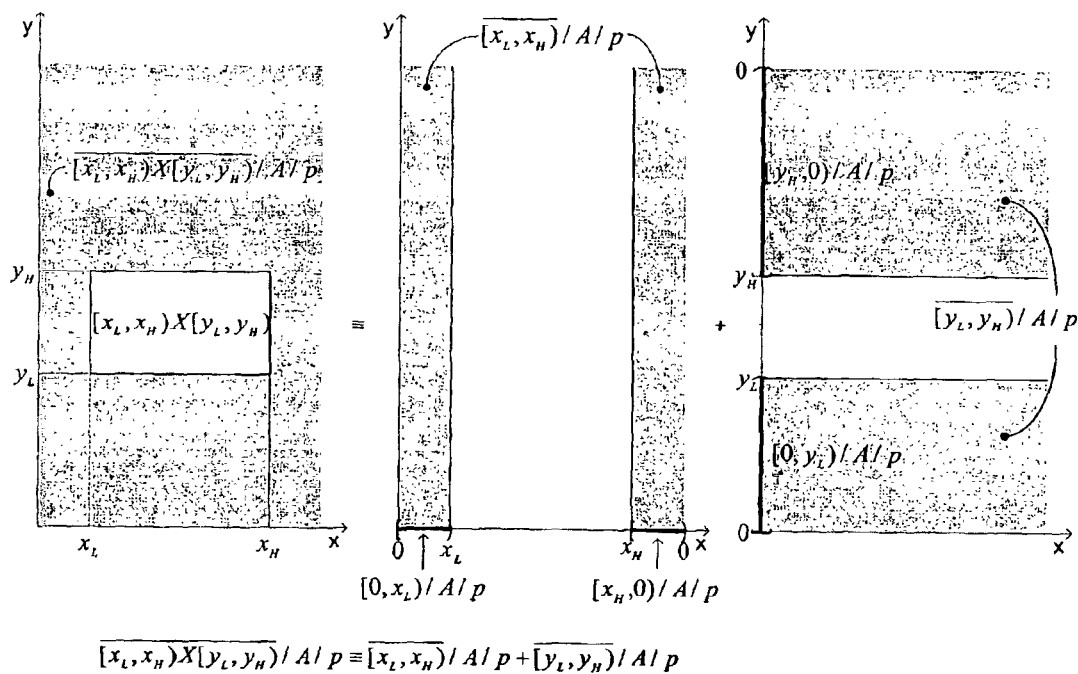
FIG. 17 is a Graphical Demonstration of the First "De Morgan" Law for a Two-Dimensional Range.
Figure 18:
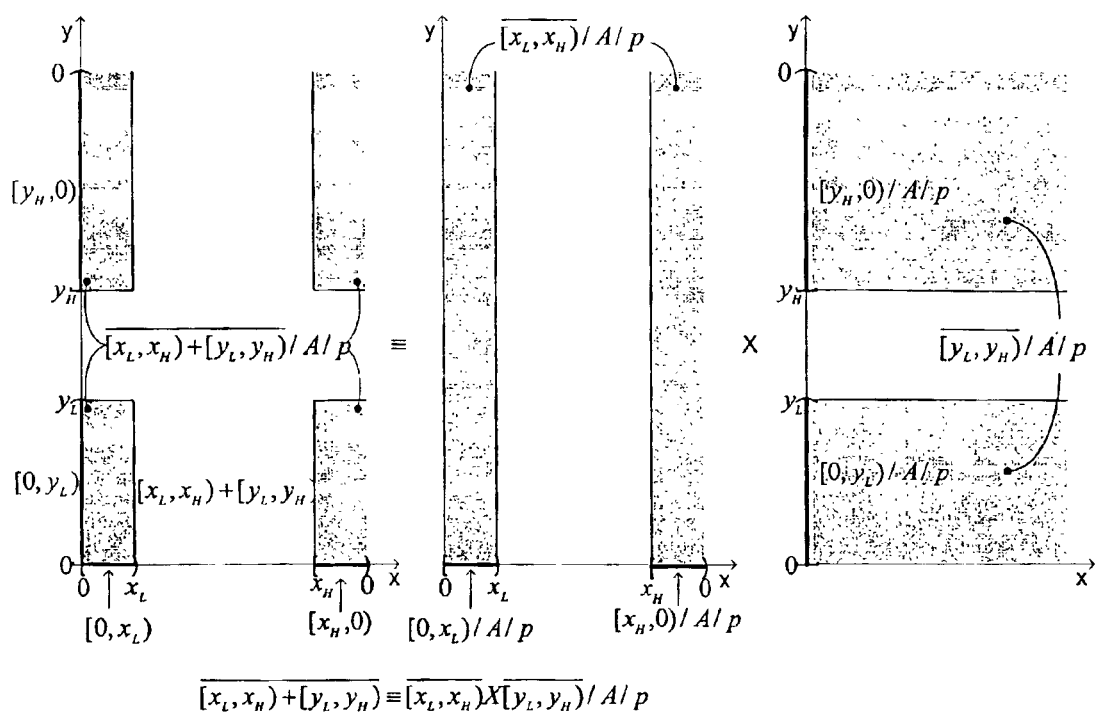
FIG. 18 is a Graphical Demonstration of the Second "De Morgan" Law for a Two-Dimensional Range.

$\overline{[x_L,x_H]X[y_L,y_H]}/A/p \equiv \overline{[x_L,x_H]}/A/p + \overline{[y_L,y_H]}/A/p$
$\overline{[x_L,x_H]+[y_L,y_H]}/A/p \equiv \overline{[x_L,x_H]}X\overline{[y_L,y_H]}/A/p$ FIG. 17 and FIG. 18 demonstrate the two "De Morgan" laws for two-dimensional ranges, which can be also interpreted as overlapping one-dimensional ranges.

3. Searching Multi-Dimensional Keys over Multi-Dimensional Ranges

Searching whether a Multi-Dimensional Key falls into a Multi-Dimensional Range, which results in an action associated with this range, is a well-know problem of database search. This problem is also known as packet classification in the communications field.

Search Problem Definition: A d-Dimensional Key, $K^d$, is submitted to a d-dimensional information base consisting of n overlapping d-dimensional ranges $\{\mathfrak{R}_0^d/A_0/p_0, \mathfrak{R}_1^d/A_1/p_1, \ldots, \mathfrak{R}_{n-1}^d/A_{n-1}/p_{n-1}\}$. Find the highest-priority range $\mathfrak{R}_i^d/A_i/p_i$ that contains the Key and perform the associated action $A_i$.

It is assumed that the data in the different dimensions are mutually independent, such that all the dimensions are orthogonal.

The Key search over a set of n overlapping d-dimensional ranges $\{\mathfrak{R}_0^d,\mathfrak{R}_1^d, \ldots \mathfrak{R}_{n-1}^d\}$ can be performed using Post-Processing or Pre-Processing. The Post-Processing method involves overlapping ranges; the submitted Key may be found in two or more overlapping ranges in each dimension; thus, priority rules are required for selecting a unique range.

The alternative, more efficient, Pre-Processing method presented below applies to a Key search over disjoint (non-overlapping) d-dimensional ranges only. In this method, the overlapping ranges are converted to equivalent disjoint ranges prior to the search; then, the submitted Key are only found in one range. Pre-processing is based on the above-described arithmetical laws for ranges.

After pre-processing, the n d-dimensional ranges of the information base are designated by $\{\mathfrak{R}_0^d/A_0,\mathfrak{R}_1^d/A_1, \ldots, \mathfrak{R}_{n-1}^d/A_{n-1}\}$ and do not require priority specification. The search problem then becomes finding the range $\mathfrak{R}_i^d/A_i$ that contains the d-Dimensional Key $K^d$ and performing the associated action $A_i$.

Figure 19A:
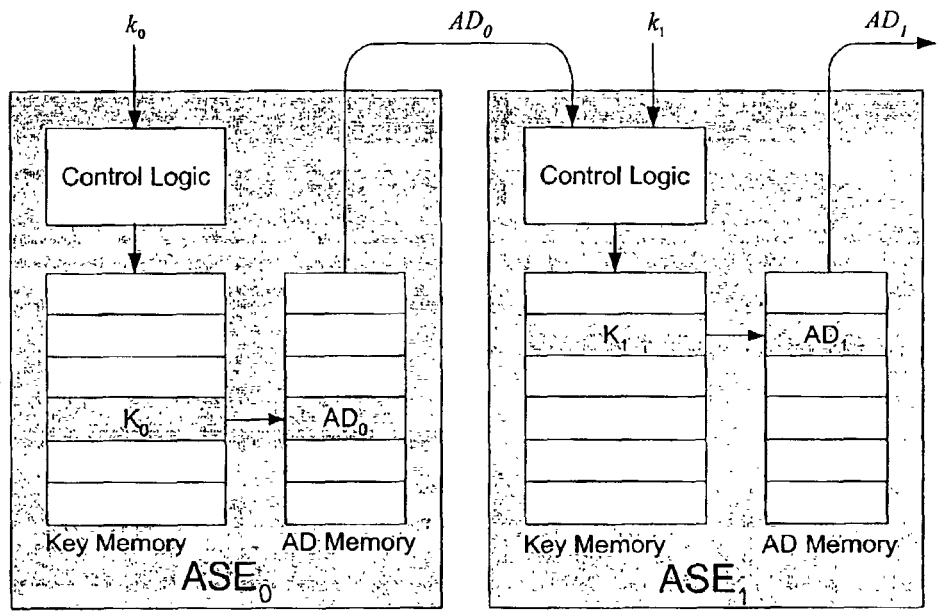
FIG. 19a provides a Basic Implementation of a Classification Procedure Using ASE with Key Memory, Associated Data Memory and Control Logic.
Figure 19B:
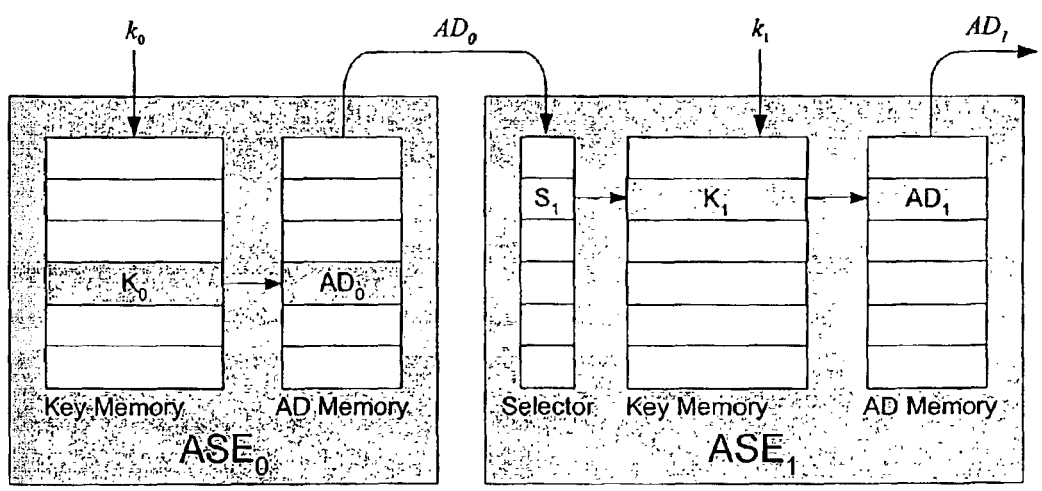
FIG. 19b provides an Alternative Implementation of a Classification Procedure Using ASE with Key Memory, Associated Data Memory and Range Selector.

Any of the above methods can be implemented with any type of d Associative Search Engines (ASEs) with Key entries and Associated Data entries. Each ASE accepts the corresponding field of the submitted Key and retrieves in response an Associated Data (AD). The AD issued by each ASE can be processed by Control Logic and applied with the succeeding field of the submitted Key to the next ASE. The AD issued by the last ASE defines the Classification Rules or actions to be performed on the selected packet. FIG. 19a shows the first two ASEs. If a standard ASE is used for all stages, then a default AD is applied to the first ASE input, which does not affect the Key search in all its Key entries.

FIG. 19a depicts a possible implementation of this ASE includes Key Memory, Associated Data Memory and a range selector; this selector receives the AD from the preceding ASE and provides corresponding output signals for selecting subsets or segments in the Key Memory entries to be searched. If overlapping ranges are allowed, then, a priority selector is also required for selecting a unique range.

Figure 19C:
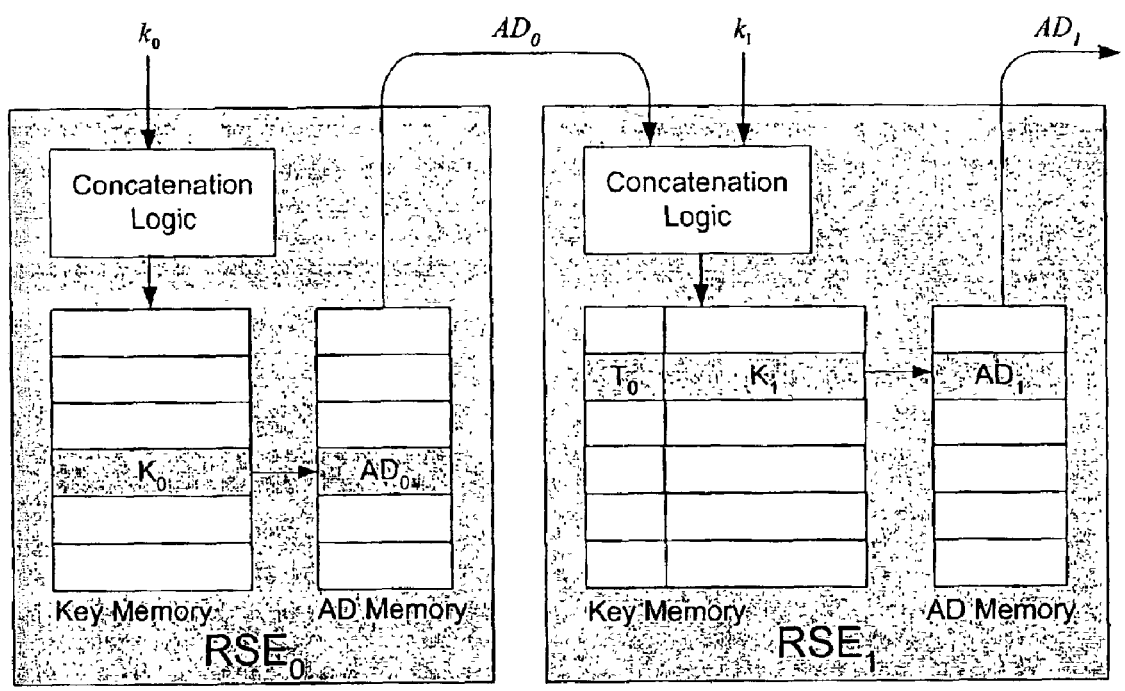
FIG. 19c illustrates a Basic Implementation of a Classification Procedure Using RSE with Key Memory, Associated Data Memory and Concatenation Logic, according to the present invention.

The inventive classification procedure is implemented with Range Search Engines (RSEs), each including a Key Memory, Associated Data Memory and Concatenation Logic (see FIG. 19c). The AD issued by each RSE for each field (in each dimension) is concatenated with the component of the submitted Key for the next field. The Concatenation Logic also synchronizes the concatenation process for maximal throughput between stages.

3.1 Two-Dimensional Search

This section deals with the question of checking whether a two-dimensional Key $K^2 \equiv (k_x,k_y)$ belongs to the two-dimensional Range $\mathfrak{R}^2/A \equiv [x_L,x_H]X[y_L,y_H]/A$, and if so, taking an action A. At the moment, we ignore the fact that the Key may belong to multiple ranges.

It will be shown hereinbelow that the method presented is general and allows dealing with a Key search in a d-dimensional range. The power of the concept presented above lies in the ability to decompose a difficult d-dimensional range search into one-dimensional range searches, which can be readily solved.

Figure 20:
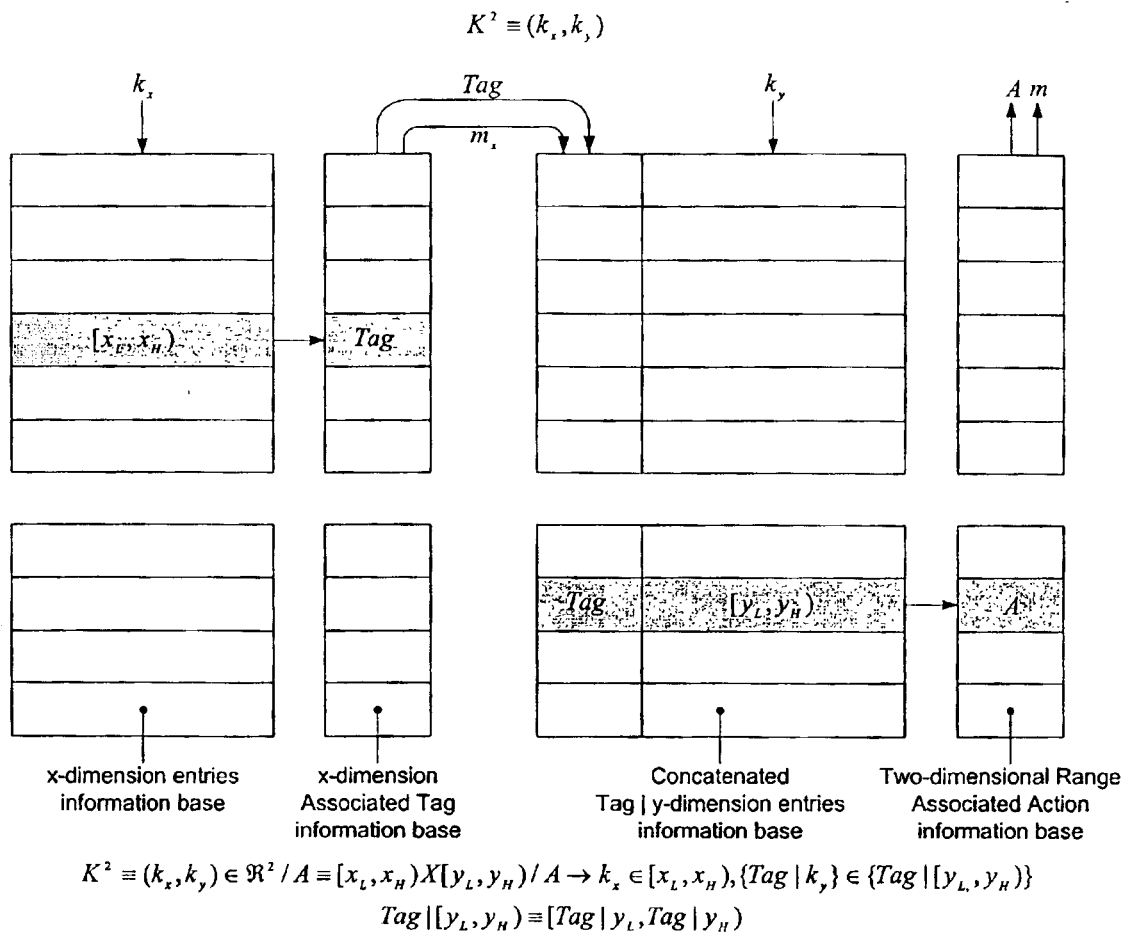
FIG. 20 illustrates a Method of a Two-Dimensional Key Search in a Two-Dimensional Range, according to the present invention.

FIG. 20 depicts the method of a two-dimensional Key search in a two-dimensional range. The two-dimensional range information base is decomposed into two one-dimensional Range Search Engines (RSEs). The leftmost information base incorporates the x-dimension ranges, whereas the rightmost one consists of tagged y-ranges; each of the latter is a concatenation of a tag and a y-dimension range.

The search algorithm proceeds as follows:

1. Search whether the Key component in the x dimension, $k_x$, belongs to a range.
2. If a two-dimensional range that contains the two-dimensional Key is not found, then issue a no-match signal $m_x = $ '0'.
3. If such an x-range $[x_L,x_H]$ is found, then issue an associated Tag accompanied by a match signal $m_x = $ '1' and proceed as follows:
   a. Concatenate the Tag with the Key $k_y$ component and use the Tag|$k_y$ as a Key to search the range entries of the form [Tag|$y_L$,Tag|$y_H$) in the y-dimension RSE placed second from the left.
   b. If a range [Tag|$y_L$,Tag|$y_H$) is found, the second one-dimensional RSE issues an Associated Data A (action), which is associated with the range $\mathfrak{R}^2/A \equiv [x_L,x_H]X[y_L,y_H]/A$. The second RSE issues a signal $m_y = $ '1', which indicates a match in the first as well as in the second RSE.
   c. If, however, no range $\mathfrak{R}^2/A \equiv [x_L,x_H]X[y_L,y_H]/A$ that contains the Key Tag|$k_y$ is found, then issue a no-match signal $m = m_x \cdot m_y = $ '0'.

Comments:
1. It is clear that $Tag|k_y \in [Tag|y_L, Tag|y_H] \rightarrow k_y \in [y_L, y_H]$.
2. The performance of a search on the y dimension followed by a search in the x dimension, by swapping the order of execution, then properly concatenating the x-dimension and y-dimension RSEs, and associating the Tag with the first RSE and the action with the second RSE, should yield identical results.
3. Since this algorithm, implemented in hardware, allows decomposing the two-dimensional problem into two sequential one-dimensional problems, which we know how to solve, we are now capable of solving a d-dimensional Key search problem by iterative application of the here above described algorithm.

EXAMPLE 2

Two-Dimensional Classification

This example can be seen as a Classification of two-field packets in order to perform actions on the selected packet. These actions are defined by the Classification Rules. The Classification procedure is expressed as a two-dimensional Key search over a set of two-dimensional ranges, where the Associated Data of the two-dimensional range that contains the submitted Key specifies the associated action to be performed on the selected packet.

Assume a search of a two-dimensional Key in a two-dimensional information base consisting of 8 x-dimension ranges ($a_0$ to $a_7$) and 6 y-dimension ranges ($b_0$ to $b_5$).

The less efficient Post-Processing method involves overlapping ranges in both dimensions. When the submitted Key is found in two or more overlapping ranges, a unique range is selected in each dimension by priority rules. First, the x-component of the submitted Key, designated $K_x$, is searched in all the x-dimension ranges. If $K_x$ is found, for instance, in the three x-dimension ranges $a_0$, $a_2$ and $a_5$, then a priority rule is applied to determine a unique range, say $a_2$. This range is assigned a Tag $T_2$, which is concatenated with the y-component of the submitted Key, designated $K_y$, and with all the y-dimension ranges. Then, the tagged $K_y$, $(T_2|K_y)$, is searched in the tagged y-dimension ranges $(T_2|b_0)$ to $(T_2|b_5)$. Similarly to the x-dimension, if $(T_2|K_y)$ is found in more than one tagged y-dimension range, a unique range is determined by priority rule.

The efficient Pre-Processing method utilized by the instant invention is based on the combination of the overlapping ranges and their conversion to equivalent disjoint ranges prior to the search. Consequently, each submitted Key is found in only one range (at most). Assume that pre-processing yields 8 disjoint x-dimension ranges ($a_0$ to $a_7$) and 6 disjoint y-dimension ranges ($b_0$ to $b_5$), as above. First, the x-component $K_x$ of the submitted Key is searched in all the x-dimension ranges. Assume that $K_x$ is found in $a_2$. This range is assigned a Tag $T_2$, which is concatenated with the y-component $K_y$ of the submitted Key and with all the y-dimension ranges for searching the tagged $K_y$, $(T_2|K_y)$, in the tagged y-dimension ranges $(T_2|b_0)$ to $(T_2|b_5)$. As in the x-dimension, only one tagged y-dimension range can contain the tagged y-dimension key $(T_2|K_y)$. If, for instance, this range is $(T_2|b_3)$, then the Classification Rule is expressed by the selected two-dimensional range $a_2 \times (T_2|b_3)$.

The above two-dimensional search using both processing methods for 8 x-dimension ranges and 6 y-dimension ranges requires the storage of 8 x-dimension ranges and 6 tagged y-dimension ranges for a single rule. Table 2a shows the required 6 tagged y-dimension ranges. A conventional classification method requires the storage of 8×6 ranges for one rule. Table 2b shows the required 48 ranges.

TABLE 2a

Representation of the 6 Tagged y-Dimension Ranges Required for a Single Rule in a set of Two-Dimensional 8x6 Ranges Using the Novel Classification Method

| y Dimension | x Dimension | | | | | | | | |
|---|---|---|---|---|---|---|---|---|---|
|  | 0 | 1 | 2 | 3 | 4 | 5 | 6 | 7 | 8 |
| 0 |  |  | $a_2x(T_2|b_0)$ |  |  |  |  |  |  |
| 1 |  |  | $a_2x(T_2|b_1)$ |  |  |  |  |  |  |
| 2 |  |  | $a_2x(T_2|b_2)$ |  |  |  |  |  |  |
| 3 |  |  | $a_2x(T_2|b_3)$ |  |  |  |  |  |  |
| 4 |  |  | $a_2x(T_2|b_4)$ |  |  |  |  |  |  |
| 5 |  |  | $a_2x(T_2|b_5)$ |  |  |  |  |  |  |
| 6 |  |  | $a_2x(T_2|b_6)$ |  |  |  |  |  |  |

TABLE 2b

Representation of the 8x6 Ranges Required for a Single Rule in a set of Two-Dimensional 8x6 Ranges Using the Conventional Classification Method

| y Dimension | x Dimension | | | | | | | |
|---|---|---|---|---|---|---|---|---|
|  | 0 | 1 | 2 | 3 | 4 | 5 | 6 | 7 |
| 0 | $a_0xb_0$ | $a_1xb_0$ | $a_2xb_0$ | $a_3xb_0$ | $a_4xb_0$ | $a_5xb_0$ | $a_5xb_0$ | $a_7xb_0$ |
| 1 | $a_0xb_1$ | $a_1xb_1$ | $a_2xb_1$ | $a_3xb_1$ | $a_4xb_1$ | $a_5xb_1$ | $a_5xb_1$ | $a_7xb_1$ |
| 2 | $a_0xb_2$ | $a_1xb_2$ | $a_2xb_2$ | $a_3xb_2$ | $a_4xb_2$ | $a_5xb_2$ | $a_5xb_2$ | $a_7xb_2$ |
| 3 | $a_0xb_3$ | $a_1xb_3$ | $a_2xb_3$ | $a_3xb_3$ | $a_4xb_3$ | $a_5xb_3$ | $a_5xb_3$ | $a_7xb_3$ |
| 4 | $a_0xb_4$ | $a_1xb_4$ | $a_2xb_4$ | $a_3xb_4$ | $a_4xb_4$ | $a_5xb_4$ | $a_5xb_4$ | $a_7xb_4$ |
| 5 | $a_0xb_5$ | $a_1xb_5$ | $a_2xb_5$ | $a_3xb_5$ | $a_4xb_5$ | $a_5xb_5$ | $a_5xb_5$ | $a_7xb_5$ |
| 6 | $a_0xb_6$ | $a_1xb_6$ | $a_0xb_6$ | $a_3xb_6$ | $a_4xb_6$ | $a_5xb_6$ | $a_5xb_6$ | $a_7xb_6$ |

Similarly, a two-dimensional search in a two-dimensional information base consisting of m x-dimension ranges and n y-dimension ranges requires the storage of these m ranges and n tagged ranges for a single rule. Table 3a shows the required n tagged y-dimension ranges when the submitted Key is found in the specific x-dimension range $a_I$ and y-dimension range $b_J$. A conventional classification method requires, on the other hand, the storage of m×n ranges for one rule, as shown in Table 3b. This comparison shows the clear superiority of the inventive classification method over the conventional method regarding the narrowing of the search in the y dimension to a subset of ranges (instead of all the entries in the y dimension) and storage efficiency. This, combined with the advantages provided by the novel Range Representation over the prefix notation in more compact storage and aggregation of CIDR address ranges, results in much smaller storage space in the RSE in comparison with any TCAM.

TABLE 3a

Representation of the n Tagged y-Dimension Ranges Required for a Single Rule in a set of Two-Dimensional mxn Ranges Using The Novel Classification Method

| y Dimension | x Dimension | | | | | |
|---|---|---|---|---|---|---|
|  | 0 | 1 | ... | I | ... | m-2 | m-1 |
| 0 |  |  | ... | $a_Ix(T_1|b_0)$ | ... |  |  |
| 1 |  |  | ... | $a_Ix(T_1|b_1)$ | ... |  |  |
| ... |  |  | ... | ... | ... |  |  |
| J |  |  | ... | $a_Ix(T_1|b_J)$ | ... |  |  |
| ... |  |  | ... | ... | ... |  |  |
| n-2 |  |  | ... | $a_Ix(T_1|b_{n-2})$ | ... |  |  |
| n-1 |  |  | ... | $a_Ix(T_1|b_{n-1})$ | ... |  |  |

TABLE 3b

Representation of the mxn Ranges Required for a Single Rule in a set of Two-Dimensional mxn Ranges Using the Conventional Classification Method

| y | x Dimension | | | | |
|---|---|---|---|---|---|
| Dimension | 0 | 1 | ... I | ... m-2 | m-1 |
| 0 | $a_0xb_0$ | $a_1xb_0$ | ... $a_Ixb_0$ | ... $a_{m-2}xb_0$ | $a_{m-1}xb_0$ |
| 1 | $a_0xb_1$ | $a_1xb_1$ | ... $a_Ixb_1$ | ... $a_{m-2}xb_1$ | $a_{m-1}xb_1$ |
| ... | ... | ... | ... ... | ... ... | ... |
| J | $a_0xb_J$ | $a_1xb_J$ | ... $a_Ixb_J$ | ... $a_{m-2}xb_J$ | $a_{m-1}xb_J$ |
| ... | ... | ... | ... ... | ... ... | ... |
| n-2 | $a_0xb_{n-2}$ | $a_1xb_{n-2}$ | ... $a_Ixb_{n-2}$ | ... $a_{m-2}xb_{n-2}$ | $a_{m-1}xb_{n-2}$ |
| n-1 | $a_0xb_{n-1}$ | $a_1xb_{n-1}$ | ... $a_Ixb_{n-1}$ | ... $a_{m-2}xb_{n-1}$ | $a_{m-1}xb_{n-1}$ |

3.2 d-Dimensional Search

Figure 21:
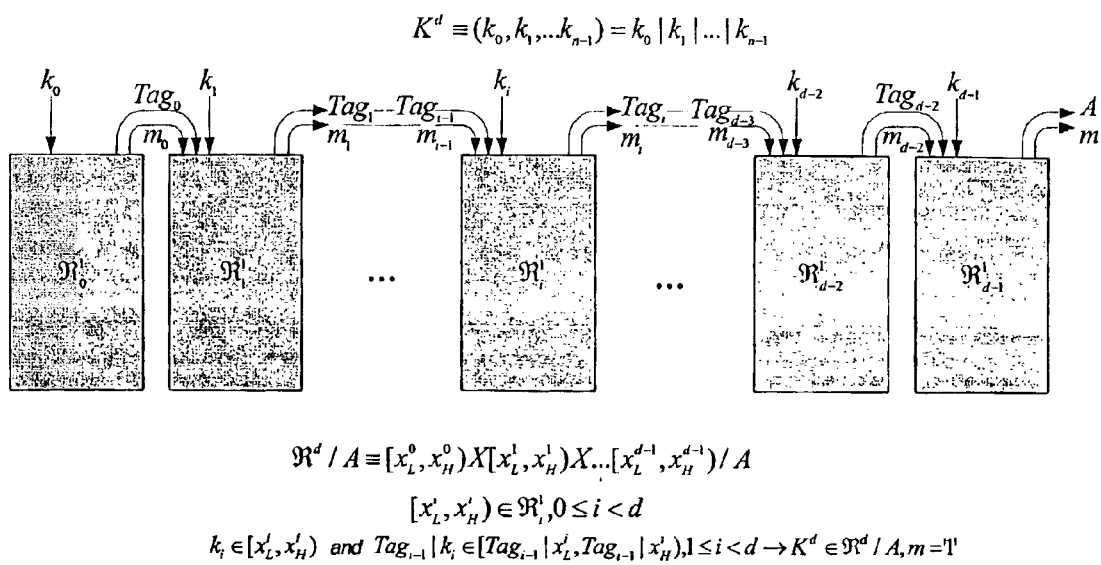
FIG. 21 illustrates a Generalized Method of a d-Dimensional Key Search in a d-Dimensional Range.

FIG. 21 demonstrates the generalized solution for the d-dimensional search problem. This solution is scalable, because it allows any number of dimensions. It can be implemented by generalizing the two-dimensional search algorithm described above to d dimensions.

Similarly to the two-dimensional case, the search on fields can be performed in any order of the multiple dimensions in the d-dimensional case, as implied by applying the Associative Law described in greater detail hereinbelow.

The solution for the d-dimensional search problem can be efficiently used in the communications field to classify packets based upon any number of packet header fields in a switch/router. In this application, the term "Classification" is used to express a multi-field (or multi-dimensional) Key search over a multi-field range set, and the term "Classification System" for the multi-field system that stores the multi-field ranges over which classification is performed. The term "Classification Rule" expresses the multi-field ranges that contain the searched multi-field Key and specifies the associated actions to be performed.

EXAMPLE 3
Dimensional Classification

This example deals with the Classification of d-field packets. For simplicity, assume n d-field ranges having a single field in all the first d-1 dimensions (numbered from 0 to d-2), each field containing the corresponding component of the submitted d-field Key, and that these d-1 fields are identical in all the dimensions; the last dimension (numbered d-1) includes n different fields. The identical d-1 fields are represented by a, b, c, . . . , p, q. The different fields of the n ranges in the last dimension (d-1) are represented by $r_0, r_1, r_2, \ldots, r_{n-2}, r_{n-1}$. These n ranges define n Classification Rules $R_0$ to $R_{n-1}$ that specify n actions $A_0$ to $A_{n-1}$.

The Classification procedure is expressed as a d-dimensional Key search over the set of d-dimensional ranges. First, the $0^{th}$-dimension component of the submitted Key, designated $K_0$, is searched in the $0^{th}$-dimension field of the stored ranges, yielding a. This field is assigned a Tag $T_0$, which is concatenated with the $1^{st}$-dimension component $K_1$ of the submitted Key, and with the $1^{st}$-dimension field b. Then, the tagged $K_1$ ($T_0|K_1$) is searched and found in the tagged b ($T_0|b$). This field is assigned a Tag $T_1$, which is concatenated with the $2^{nd}$-dimension component $K_2$ of the submitted Key, and with the identical $2^{nd}$-dimension field c, for searching and so on, until the $(d-2)^{th}$ dimension, where ($T_{d-3}|K_{d-2}$) is searched and found in ($T_{d-3}|q$) and is assigned a Tag $T_{d-2}$. The $(d-1)^{th}$ dimension has n fields $r_0$ to $r_{n-1}$. The tagged $K_{d-1}$ ($T_{d-2}|K_{d-1}$) is searched and found in the n tagged fields ($T_{d-2}|r_0$) to ($T_{d-2}|r_{n-1}$) yielding n Classification Rules $R_0$ to $R_{n-1}$ that specify n actions $A_0$ to $A_{n-1}$.

Table 4a shows that Classification of n d-field packets with fields varying in a single dimension requires (d+n−1) tagged fields. A conventional classification method requires, on the other hand, d×n fields, as shown in Table 4b. This comparison shows again the clear superiority of the novel classification method over the conventional method with regard to storage efficiency.

TABLE 4a

Representation of the Tagged d-Field Ranges Required for Fields Varying in a Single Dimension Using The Novel Classification Method

| Rule | Field | | | | | | | Action |
|---|---|---|---|---|---|---|---|---|
| | 0 | 1 | 2 | ... | d-3 | d-2 | d-1 | |
| $R_0$ | a | $T_0|b$ | $T_1|c$ | ... | $T_{d-4}|p$ | $T_{d-3}|q$ | $T_{d-2}|r_0$ | $A_0$ |
| $R_1$ | | | | | | | $T_{d-2}|r_1$ | $A_1$ |
| $R_2$ | | | | | | | $T_{d-2}|r_2$ | $A_2$ |
| ... | | | | | | | ... | ... |
| $R_{n-3}$ | | | | | | | $T_{d-2}|r_{n-3}$ | $A_{n-3}$ |
| $R_{n-2}$ | | | | | | | $T_{d-2}|r_{n-2}$ | $A_{n-2}$ |
| $R_{n-1}$ | | | | | | | $T_{d-2}|r_{n-1}$ | $A_{n-1}$ |

TABLE 4b

Representation of the dxn d-Field Ranges Required for Fields Varying in a Single Dimension Using the Conventional Classification Method

| Rule | Field | | | | | | | Action |
|---|---|---|---|---|---|---|---|---|
| | 0 | 1 | 2 | ... | d-3 | d-2 | d-1 | |
| $R_0$ | a | b | c | ... | p | q | $r_0$ | $A_0$ |
| $R_1$ | a | b | c | ... | p | q | $r_1$ | $A_1$ |
| $R_2$ | a | b | c | ... | p | q | $r_2$ | $A_2$ |
| ... | ... | ... | ... | ... | ... | ... | ... | ... |
| $R_{n-3}$ | a | b | c | ... | p | q | $r_{n-3}$ | $A_{n-3}$ |
| $R_{n-2}$ | a | b | c | ... | p | q | $r_{n-2}$ | $A_{n-2}$ |
| $R_{n-1}$ | a | b | c | ... | p | q | $r_{n-1}$ | $A_{n-1}$ |

The above examples show that, whereas using conventional classification methods, the stored data in the information base is an exponential function of the number of fields, the inventive classification method grows moderately; besides, redundant information does not require extra storage. This is due to the use of the tags, that concatenated as most significant bits with the fields of the next dimension, determine ordered segments, limiting the number of elements to be searched.

Tagging can be viewed as the application of the algebraic Distributive Law listed hereinabove, where the redundant terms are separated as a common factor. For instance, a specific rule depicted in Table 4a for the Classification Method of the present invention can be expressed in Boolean algebra as:

$$R_i = a \bullet T_0 | b \bullet T_1 | c \bullet \ldots \bullet T_{d-4} | p \bullet T_{d-3} | q \bullet T_{d-2} | r_i$$

and the set of n rules can be expressed as:

$$a \bullet T_0 | b \bullet T_1 | c \bullet \ldots \bullet T_{d-4} | p \bullet T_{d-3} | q \bullet \{T_{d-2} | r_0 + T_{d-2} | r_1 + \ldots + T_{d-2} | r_{n-1}\}$$
(d+n−1 fields)

The equivalent specific rule depicted in Table 4b for Conventional Classification Method can be expressed as:

$$R_i = a \bullet b \bullet c \bullet \ldots \bullet p \bullet q \bullet r_i$$

and the set of n rules as:

$$a \bullet b \bullet c \bullet \ldots \bullet p \bullet q \bullet r_0 + a \bullet b \bullet c \bullet \ldots \bullet p \bullet q \bullet r_1 + a \bullet b \bullet c \bullet \ldots \bullet p \bullet q \bullet r_2 + \ldots$$
$$+ a \bullet b \bullet c \bullet \ldots \bullet p \bullet q \bullet r_{n-3} + a \bullet b \bullet c \bullet \ldots \bullet p \bullet q \bullet r_{n-2} + a \bullet b \bullet c \bullet \ldots \bullet p \bullet q \bullet r_{n-1}$$
(d×n fields)

The expressions above show in algebraic terms that the Classification of n d-field packets with fields varying in a single dimension requires (d+n−1) tagged fields using the inventive method, whereas the conventional method requires d×n fields. This is due to the fact that in the inventive method, the Distributive Law is used to separate the redundant terms as common factor, as mentioned above.

In general, as more dimensions are used in an information base, fewer elements are included in each dimension and a faster search per dimension can be performed. However, more dimensions require more search steps and increased latency; but this problem can be solved by pipelining to achieve up to one search result per clock, as described in Chapter 5.

EXAMPLE 4 d-Dimensional Forwarding

A d-Dimensional Forwarding can be viewed as a special case of the d-Dimensional Classification shown in Example3 above. In this case, all the first d−1 dimensions (numbered from 0 to d−2) contain a single identical field in each dimension that includes all the integer values in this dimension; the last dimension (numbered d−1) contains n IP Destination Addresses (IPDAs).

Table 5a shows that forwarding of n d-dimensional packets represented in by their IPDAs in the last dimension (numbered d−1) requires (d+n−1) fields in the inventive forwarding method. A conventional forwarding method requires, on the other hand, d×n fields, as shown in Table 5b. This comparison shows the clear advantage of this novel forwarding method over the conventional method with regards to storage efficiency. A field that covers all the integer values in a dimension is represented by [0,0) in the inventive Range Representation in Table 5a and by a string of xxx . . . x (don't cares) in the conventional TCAM notation; this field is denoted by "any" in Table 5b.

TABLE 5a

Representation of the d-Field Ranges Required for Fields Varying in a Single Dimension Using The Inventive Forwarding Method

| Rule | Field | | | | | | | Action |
|---|---|---|---|---|---|---|---|---|
| | 0 | 1 | 2 | ... | d-3 | d-2 | d-1 | |
| $R_0$ | [0,0) | [0,0) | [0,0) | ... | [0,0) | [0,0) | $IPDA_0$ | $A_0$ |
| $R_1$ | | | | | | | $IPDA_1$ | $A_1$ |
| $R_2$ | | | | ... | | | $IPDA_2$ | $A_2$ |
| ... | | | | ... | | | ... | ... |
| $R_{n-3}$ | | | | ... | | | $IPDA_{n-3}$ | $A_{n-3}$ |
| $R_{n-2}$ | | | | ... | | | $IPDA_{n-2}$ | $A_{n-2}$ |
| $R_{n-1}$ | | | | ... | | | $IPDA_{n-1}$ | $A_{n-1}$ |

TABLE 5b

Representation of the d×n d-Field Ranges Required for Fields Varying in a Single Dimension Using the Conventional Forwarding Method

| Rule | Field | | | | | | | Action |
|---|---|---|---|---|---|---|---|---|
| | 0 | 1 | 2 | ... | d-3 | d-2 | d-1 | |
| $R_0$ | any | any | any | ... | any | any | $IPDA_0$ | $A_0$ |
| $R_1$ | any | any | any | ... | any | any | $IPDA_1$ | $A_1$ |
| $R_2$ | any | any | any | ... | any | any | $IPDA_2$ | $A_2$ |
| ... | ... | ... | ... | ... | ... | ... | ... | ... |
| $R_{n-3}$ | any | any | any | ... | any | any | $IPDA_{n-3}$ | $A_{n-3}$ |
| $R_{n-2}$ | any | any | any | ... | any | any | $IPDA_{n-2}$ | $A_{n-2}$ |
| $R_{n-1}$ | any | any | any | ... | any | any | $IPDA_{n-1}$ | $A_{n-1}$ |

Forwarding of n d-dimensional packets represented in by their IPDAs in the last dimension (numbered d−1), as depicted in Table 5a for the instant Forwarding Method, can be expressed in Boolean algebra as:

$$[0,0) \cdot [0,0) \cdot [0,0) \cdot \ldots \cdot [0,0) \cdot \{IPDA_0 + IPDA_1 + \ldots + IPDA_{n-2} + IPDA_{n-1}\}$$

where d−1 fields denoted by [0,0) are required, totaling d+n−1 fields; [0,0) represents a field covering all the integer values in a dimension in the instant Range Representation.

Forwarding of n d-dimensional packets, depicted in Table 5b for Conventional Classification Method, can be expressed as:

$$any \cdot any \cdot any \cdot \ldots \cdot any \cdot IPDA_0 + any \cdot any \cdot any \cdot \ldots \cdot any \cdot IPDA_1 + \ldots + any \cdot any \cdot any \cdot \ldots \cdot any \cdot IPDA_{n-2} + any \cdot any \cdot any \cdot \ldots \cdot any \cdot IPDA_{n-1}$$ (d×n fields)

where n×(d−1) fields denoted by "any" are required, totaling n×d fields; "any" represents a field covering all the integer values in a dimension, equivalent to a string of xxx . . . x (don't cares) in the conventional TCAM notation.

This is another example of the application of the algebraic Distributive Law to reduce the amount of stored data, by preventing the repetition of redundant data; this time in packet forwarding.

4. Implementing Multi-Dimensional Search with RSE Devices

Classification of d-field packets expressed as a d-dimensional Key search over a set of d-dimensional ranges can be implemented with any type of d associative search engines that can retrieve associated data in response to the d-fields of a submitted Key, and can be concatenated so that the Associated Data (AD) or Tag issued by each engine is processed and applied with the appropriate field of the submitted Key to the next engine. The associated data issued by the last engine define the Classification Rules or actions to be performed on the selected packet. The Classification procedure requires the concatenation of the associated data issued for each field (in each dimension) with the component of the submitted Key for the next field. This operation is performed by a Concatenation Logic, which also synchronizes the concatenation process for maximal throughput between stages. For design purposes, a standard engine may be used for all stages, including the first. In this case, a default Tag is applied to the first engine input, which determines a Key search in all the first engine ranges (instead of a subset of ranges in the succeeding engines).

The use of RSE devices, integrated with internal or external Concatenation Logic, provides the Multi-Dimensional Range Search Engines with the unique RSE capabilities, such as storage of any number of rules, any number of fields and any field widths, scalability options to build information base of any size with none or little glue logic, and the performance and lowest power consumption currently available.

Figure 22:
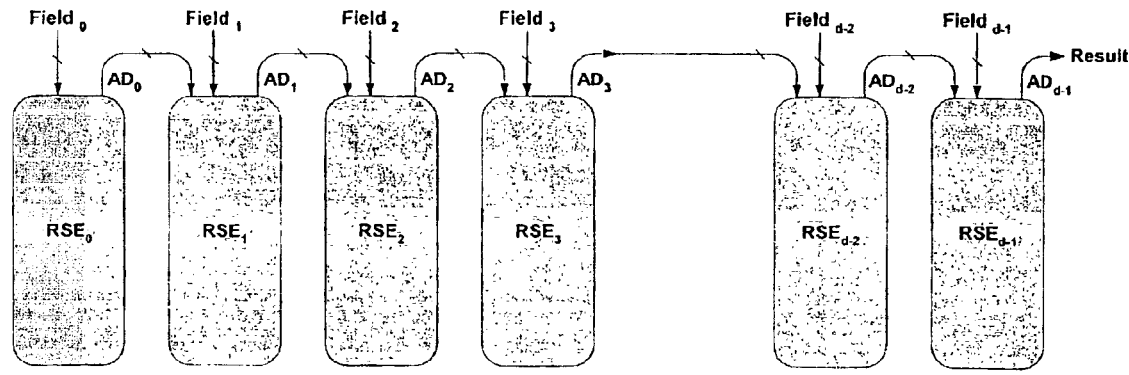
FIG. 22 is a schematic illustration of d Concatenated RSE devices (with internal Concatenation Logic) forming a d-Dimensional CIB.

FIG. 22 shows d concatenated RSE devices (with internal Concatenation Logic) conforming a d-dimensional Classification Information Base (CIB). This set of RSE devices, with either internal or external Concatenation Logic, can be used to implement a CIB with any number of fields.

Figure 23:
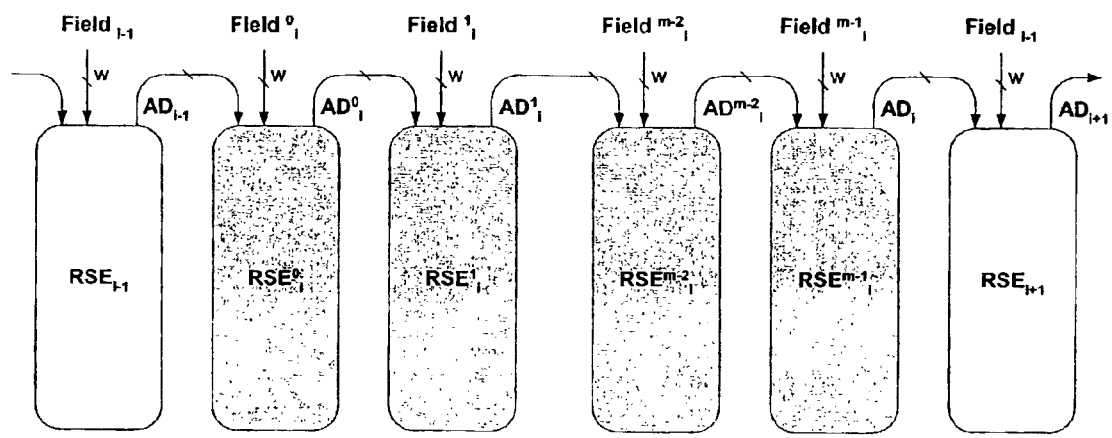
FIG. 23 is a schematic illustration of Concatenated RSE Devices forming a Single RSE within a d-Dimensional CIB.

FIG. 23 shows m concatenated RSE devices ($RSE^0_i$ to $RSE^{m-1}_i$) conforming one equivalent larger $RSE_i$ within a d-dimensional CIB. If the field width of each partial RSE is w, then the compound $RSE_i$ supports field widths up to m×w. This arrangement can be used to implement a CIB with any field widths.

Since an RSE can be formed from multiple modules, and each module can contain multiple RAMs, then an RSE-based CIB can support any number of classification rules.

EXAMPLE 5

IPv4 Classification

Figure 24:
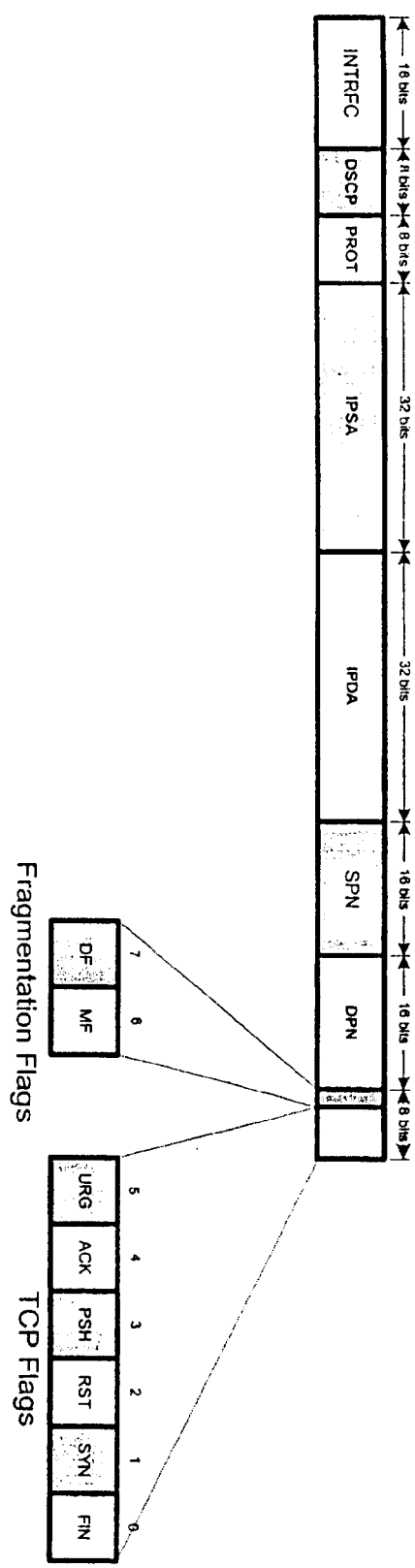
FIG. 24 shows an IPv4 Classification Key of the background art.

This example deals with the classification of packets according to their IPv4 Classification Key (see FIG. 24). The various fields of this Key can be arranged in a set of several dimensions for classification by means of a corresponding set of RSE devices.

It is assumed that the packet is parsed and the Classification Key fields are extracted, prior to being used in classification, and the Classifier is able to perform an action on the basis of the extracted information. Not all these fields are necessarily used all the time; some of the fields are not used at all in some Classifiers.

Once the field values (bits) are extracted from the packet and a Key is formed, the classification key is submitted as a query to the CIB. For instance, if the fields used by the Classifier are INTRFC, TOS, PROT, IPSA, IPDA, SPN and DPN, then the concatenated Key is:

Key=INTRFC|TOS|PROT|IPSA|IPDA|SPN|DPN

In general, a rule takes the following form:

$$\Re=[INTRFC_L, INTRFC_H] \cdot [TOS_L, TOS_H] \cdot [PROT_L, PROT_H] \cdot [IP\text{-}SA_L, IPSA_H] \cdot [IPDA_L, IPDA_H] \cdot [SPN_L, SPN_H] \cdot [DPN_L, DPN_H]/A$$

where $\Re$ is the classification rule, $[INTRFC_L, INTRFC_H]$ is the interface value range (see Ref. X4 for range definition), $[TOS_L, TOS_H]$ is the Type of Service field range,
$[PROT_L, PROT_H]$ is the Protocol value range,
$[IPSA_L, IPSA_H]$ is the IP Source Address value range,
$[IPDA_L, IPDA_H]$ is the IP Destination Address value range,
$[SPN_L, SPN_H]$ is the Source Port Number value range,
$[DPN_L, DPN_H]$ is the Destination Port Number value range, and A is the action performed on the rule.

The rule states that if the packet fields INTRFC, TOS, PROT, IPSA, IPDA, SPN and DPN fulfill the following conditions:

INTRFC∈[$INTRFC_L$, $INTRFC_H$), and
TOS∈[$TOS_L$, $TOS_H$), and
PROT∈[$PROT_L$, $PROT_H$), and
IPSA∈[$IPSA_L$, $IPSA_H$), and
IPDA∈[$IPDA_L$, $IPDA_H$), and
SPN∈[$SPN_L$, $SPN_H$), and
DPN∈[$DPN_L$, $DPN_H$), then they are subject to action A by this rule.

A typical CIB contains many rules. In case of overlapping rules, two or more rules may be subject to a different action. This is resolved by priority; where the i-th classification rule $\Re_i$ has an associated unique priority $p_i$. Thus, a classification rule can be expressed as follows:

$$\Re_i=[INTRFC_L^i, INTRFC_H^i] \cdot [TOS_L^i, TOS_H^i] \cdot [PROT_L^i, PROT_H^i] \cdot [IPSA_L^i, IPSA_H^i] \cdot [IPDA_L^i, IPDA_H^i] \cdot [SPN_L^i, SPN_H^i] \cdot [DPN_L^i, DPN_H^i]/p_i, A_i$$

and a set of ρ classification rules in the CIB may be expressed as a set of ρ logic equalities as above, where $0 \leq i \leq \rho-1$.

The rules may be arranged in a priority order, so that, for instance, the highest priority classification rule is $\Re_0$ and the lowest priority is $\Re_{\rho-1}$. This can be also interpreted as the sequential examination of the rules from $\Re_0$ to $\Re_{\rho-1}$; if $\Re_0$ is found true, apply $A_0$; if found false continue with $\Re_1$, and so on, until the first examined rule $\Re_e$ is found and the respective action $A_e$ is applied. If no rule matches the packet field, then a no-match condition is reported and a default action $A_d$ takes place.

Using this convention, the priority notion may be omitted, and the CIB classification rule may take the following form:

$$\Re_i=[INTRFC_L^i, INTRFC_H^i] \cdot [TOS_L^i, TOS_H^i] \cdot [PROT_L^i, PROT_H^i] \cdot [IPSA_L^i, IPSA_H^i] \cdot [IPDA_L^i, IPDA_H^i] \cdot [SPN_L^i, SPN_H^i] \cdot [DPN_L^i, DPN_H^i]/A_i$$

Similarly, a set of ρ classification rules in the CIB may be expressed as a set of corresponding ρ logic equalities where $0 \leq i \leq \rho-1$.

Figure 25:
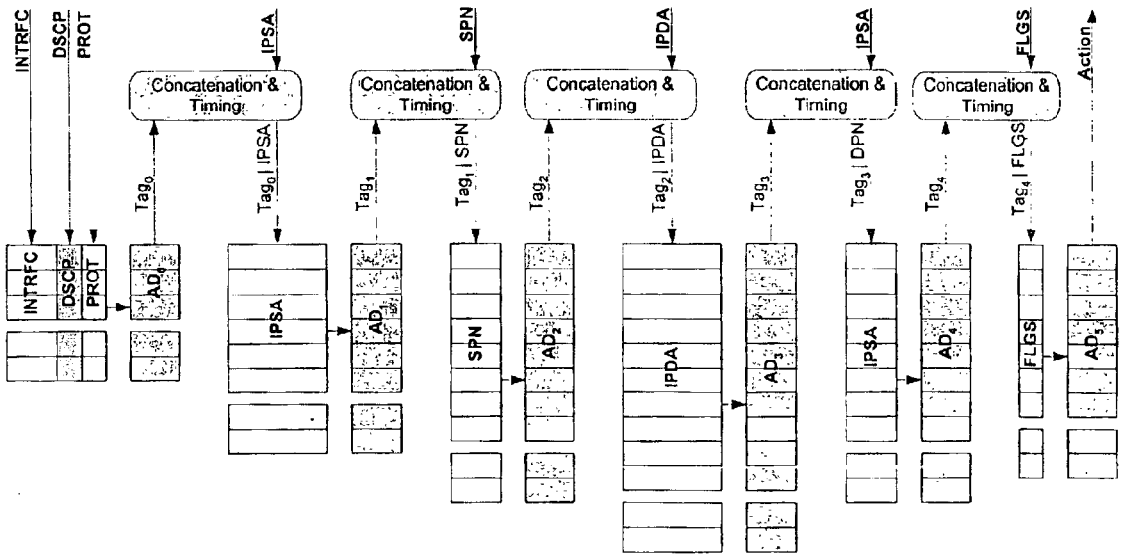
FIG. 25 shows a Generic Arrangement of RSE Sections for Classifying a Submitted IPv4 Classification Key.

FIG. 25 shows a generic arrangement of RSE sections for classifying a submitted IPv4 Classification Key. The first three fields in the IPv4 Classification Key (FIG. 24), INTRFC, DSCP and PROT, contain single values, whereas all the other fields contain ranges of integer values; therefore, a suitable option is to integrate the first three fields into one compound single-valued field that is classified by the first RSE section. The other fields, consisting of ranges, are classified in this example by means of five other RSE sections with external Concatenation Logic. Each of these five RSE sections is represented in FIG. 25 by a Key Memory that receives a tagged input Key, and an Associated Data (AD) Memory that issues a tag for concatenation with the next RSE section.

Figure 26:
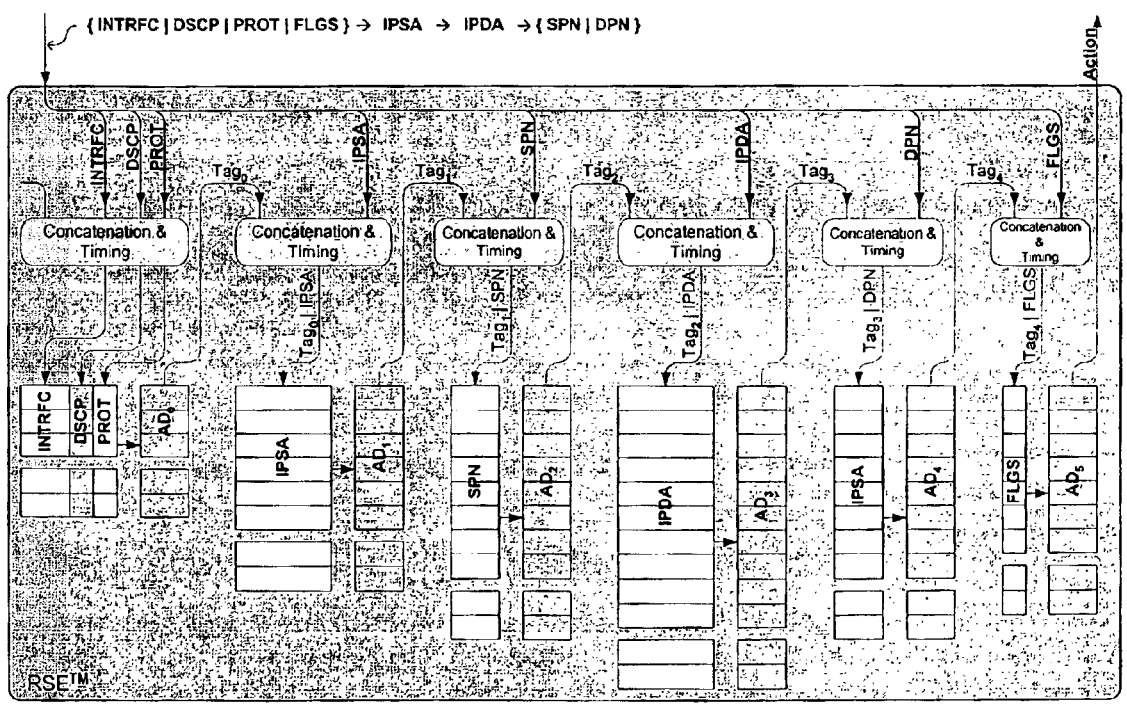
FIG. 26 provides an Implementation of Sequential Classification using a Single RSE.
Figure 27:
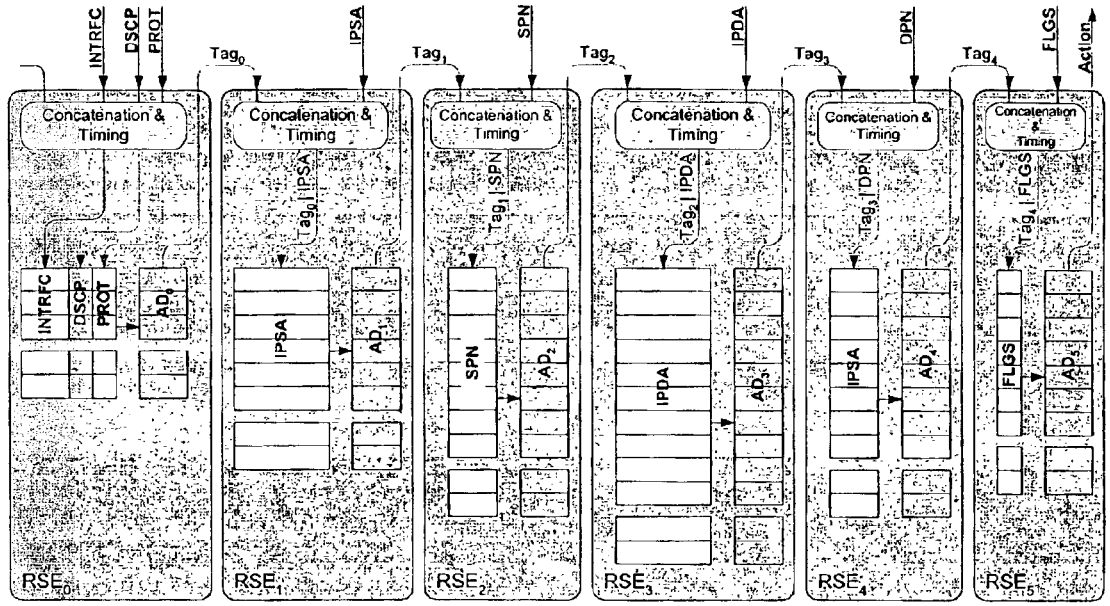
FIG. 27 provides an Implementation of Pipelined Classification using Six RSE Devices.
Figure 28:
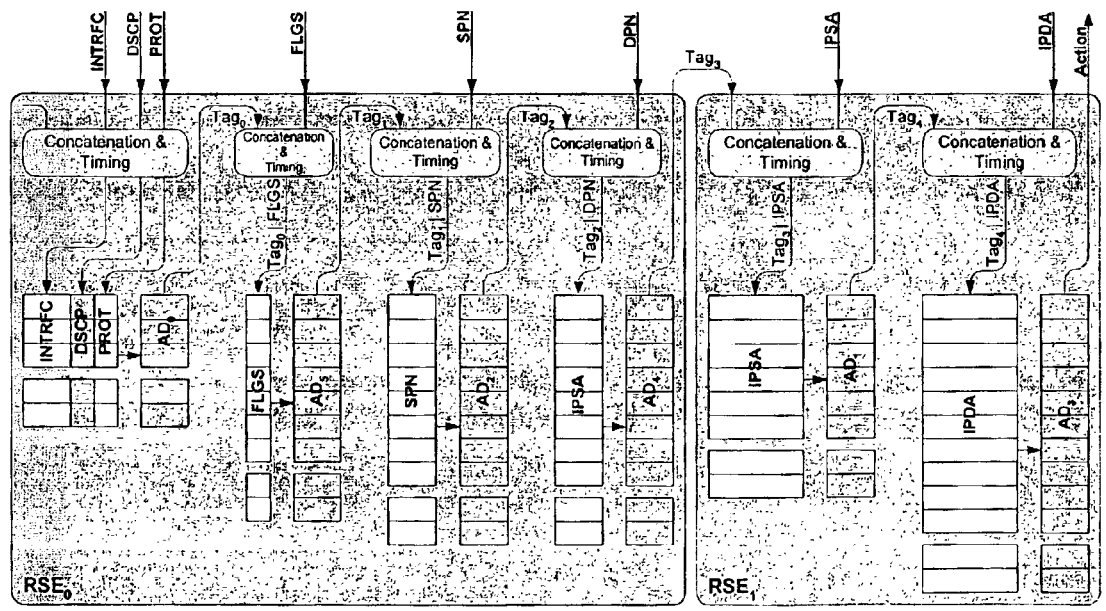
FIG. 28 provides an Implementation of a Partially Pipelined Classification having two RSE Devices Combining Internally Sequential within Externally Parallel Operation.

FIG. 26 shows an implementation of the classification device above using a single RSE with internal Concatenation Logic. Assuming that the RSE can perform a single search at a time, successive searches in different fields within one classification can only be performed sequentially, resulting in a relatively long classification cycle and relatively low throughput. Using several RSE devices, six for instance, as shown in FIG. 27, successive searches in different fields can be performed in parallel by pipelining, thus achieving a much higher throughput. If the number of RSE devices used equals the number of fields, then one classification result per clock can be achieved by pipelining. FIG. 28 shows the classification performed in two RSE devices. In this case, the successive searches in different fields are performed sequentially within the two RSE devices, but the two devices can operate in parallel, so that partial pipelining is achieved.

EXAMPLE 5

Comparing the Storage of IPv4 Classification Fields in a Typical TCAM and in the Inventive RSE This example provides a comparison of the method of storage of the four IPv4 Classification fields listed below in a typical TCAM (Table 6a) with the more efficient, inventive method used in the RSE (Table 6b).

Source: IP: 103.22.53.192/26 UDP/TCP Range: 103 to 416
Destination: IP: 117.90.0.0/13 UDP/TCP Range: 71 to 75

TABLE 6a

Storage of the four IPv4 Classification Fields in a Typical TCAM

| Source IP Address | Source UDP/TCP Port | Destination IP Address | Dest UDP/TCP Port |
|---|---|---|---|
| 0110 0111 0001 0110 0011 0101 11xx xxxx | 0000 0000 0110 0111 | 0111 0101 0101 1xxx xxxx xxxx xxxx xxxx | 0000 0000 0100 0111 |
| 0110 0111 0001 0110 0011 0101 11xx xxxx | 0000 0000 0110 0111 | 0111 0101 0101 1xxx xxxx xxxx xxxx xxxx | 0000 0000 0100 10xx |
| 0110 0111 0001 0110 0011 0101 11xx xxxx | 0000 0000 0110 1xxx | 0111 0101 0101 1xxx xxxx xxxx xxxx xxxx | 0000 0000 0100 0111 |
| 0110 0111 0001 0110 0011 0101 11xx xxxx | 0000 0000 0110 1xxx | 0111 0101 0101 1xxx xxxx xxxx xxxx xxxx | 0000 0000 0100 10xx |
| 0110 0111 0001 0110 0011 0101 11xx xxxx | 0000 0000 0111 xxxx | 0111 0101 0101 1xxx xxxx xxxx xxxx xxxx | 0000 0000 0100 0111 |
| 0110 0111 0001 0110 0011 0101 11xx xxxx | 0000 0000 0111 xxxx | 0111 0101 0101 1xxx xxxx xxxx xxxx xxxx | 0000 0000 0100 10xx |
| 0110 0111 0001 0110 0011 0101 11xx xxxx | 0000 0000 1xxx xxxx | 0111 0101 0101 1xxx xxxx xxxx xxxx xxxx | 0000 0000 0100 0111 |
| 0110 0111 0001 0110 0011 0101 11xx xxxx | 0000 0000 1xxx xxxx | 0111 0101 0101 1xxx xxxx xxxx xxxx xxxx | 0000 0000 0100 10xx |
| 0110 0111 0001 0110 0011 0101 11xx xxxx | 0000 0001 1010 0000 | 0111 0101 0101 1xxx xxxx xxxx xxxx xxxx | 0000 0000 0100 0111 |
| 0110 0111 0001 0110 0011 0101 11xx xxxx | 0000 0001 1010 0000 | 0111 0101 0101 1xxx xxxx xxxx xxxx xxxx | 0000 0000 0100 10xx |
| 0110 0111 0001 0110 0011 0101 11xx xxxx | 0000 0001 100x xxxx | 0111 0101 0101 1xxx xxxx xxxx xxxx xxxx | 0000 0000 0100 0111 |
| 0110 0111 0001 0110 0011 0101 11xx xxxx | 0000 0001 100x xxxx | 0111 0101 0101 1xxx xxxx xxxx xxxx xxxx | 0000 0000 0100 10xx |
| 0110 0111 0001 0110 0011 0101 11xx xxxx | 0000 0001 0xxx xxxx | 0111 0101 0101 1xxx xxxx xxxx xxxx xxxx | 0000 0000 0100 0111 |
| 0110 0111 0001 0110 0011 0101 11xx xxxx | 0000 0001 0xxx xxxx | 0111 0101 0101 1xxx xxxx xxxx xxxx xxxx | 0000 0000 0100 10xx |

Note:
x = don't care in TCAM Representation.

TABLE 6b

Storage of the four IPv4 Classification Fields in the Inventive RSE

| Source IP Address | Source UDP/TCP Port | Destination IP Address | Dest UDP/TCP Port |
|---|---|---|---|
| [103.22.53.192,103.22.54.0) | [103,417) | [117.88.0.0,117.96.0.0) | [71,76) |

In this example, the required storage space in the TCAM is: 14×144 ternary bits≅4032 binary bits. The required storage space in the RSE is instead only 192 binary bits.

EXAMPLE 6
Comparing the Storage of ACL Fields in a Typical TCAM and in the Novel RSE This example provides a comparison of the method of storage of a specific ACL in a typical TCAM (Table 7a) with the more efficient method used in the Novel RSE (Table 7b). This ACL permits the transfer of a TCP packet arriving from any Source Address to a Destination Address ranging from 160.11.0.0 to 160.11.255.255, at a Destination Port Number greater than 1023.

TABLE 7a

Storage of ACL Fields in a Typical TCAM

| al | prot | ipsa | spn | ipda | dpn | tcpflgs |
|---|---|---|---|---|---|---|
| 0.101 | 6 | 0.0.0.0/0 | 0.0/0 | 160.11.0.0/16 | 4.0/6 | X0X1XX |
| 0.101 | 6 | 0.0.0.0/0 | 0.0/0 | 160.11.0.0/16 | 8.0/5 | X0X1XX |
| 0.101 | 6 | 0.0.0.0/0 | 0.0/0 | 160.11.0.0/16 | 16.0/4 | X0X1XX |
| 0.101 | 6 | 0.0.0.0/0 | 0.0/0 | 160.11.0.0/16 | 32.0/3 | X0X1XX |
| 0.101 | 6 | 0.0.0.0/0 | 0.0/0 | 160.11.0.0/16 | 64.0/2 | X0X1XX |
| 0.101 | 6 | 0.0.0.0/0 | 0.0/0 | 160.11.0.0/16 | 128.0/1 | X0X1XX |
| 0.101 | 6 | 0.0.0.0/0 | 0.0/0 | 160.11.0.0/16 | 4.0/6 | X1X0XX |
| 0.101 | 6 | 0.0.0.0/0 | 0.0/0 | 160.11.0.0/16 | 8.0/5 | X1X0XX |
| 0.101 | 6 | 0.0.0.0/0 | 0.0/0 | 160.11.0.0/16 | 16.0/4 | X1X0XX |
| 0.101 | 6 | 0.0.0.0/0 | 0.0/0 | 160.11.0.0/16 | 32.0/3 | X1X0XX |
| 0.101 | 6 | 0.0.0.0/0 | 0.0/0 | 160.11.0.0/16 | 64.0/2 | X1X0XX |
| 0.101 | 6 | 0.0.0.0/0 | 0.0/0 | 160.11.0.0/16 | 128.0/1 | X1X0XX |
| 0.101 | 6 | 0.0.0.0/0 | 0.0/0 | 160.11.0.0/16 | 4.0/6 | X1X1XX |
| 0.101 | 6 | 0.0.0.0/0 | 0.0/0 | 160.11.0.0/16 | 8.0/5 | X1X1XX |
| 0.101 | 6 | 0.0.0.0/0 | 0.0/0 | 160.11.0.0/16 | 16.0/4 | X1X1XX |
| 0.101 | 6 | 0.0.0.0/0 | 0.0/0 | 160.11.0.0/16 | 32.0/3 | X1X1XX |
| 0.101 | 6 | 0.0.0.0/0 | 0.0/0 | 160.11.0.0/16 | 64.0/2 | X1X1XX |
| 0.101 | 6 | 0.0.0.0/0 | 0.0/0 | 160.11.0.0/16 | 128.0/1 | X1X1XX |

TABLE 7a

Storage of ACL Fields in the Inventive RSE

| Al | prot | ipsa | spn | ipda | dpn | tcpflgs |
|---|---|---|---|---|---|---|
| 101 | 6 | [0.0.0.0,0.0.0.0) | [0.0,0.0) | [160.11.0.0,160.11.0.1) | [4.0,0.0) | {[1,1)+[1,0)+[1,1)+[1,0)+[1,1)+[1,1)} |

(where the two bold left-hand fields are single valued, and all the other fields are ranges).

Table 7a shows that the storage of the ACL fields above in a typical TCAM requires 18 rules. Since each rule has 144 ternary bits, a total of 2592 ternary bits (equivalent to 518 binary bits) are used. The same ACL fields require a single rule and 342 binary bits in the inventive RSE (Table 7b).

EXAMPLE 7
IPv6 Forwarding Information Compression

Forwarding of IPv6 packets involves IP Destination Addresses (IPDAs) of 128 bits. Each of these IPDAs, which actually define ranges of addresses, can be divided in four fields of 32 bits. Then, the search of a single submitted 128-bit IPDA can be transformed in a search of four 32-bit fields, designated $IPDA_3$ to $IPDA_0$. This search is similar to a classification of a submitted four-dimensional Key.

Figure 29:
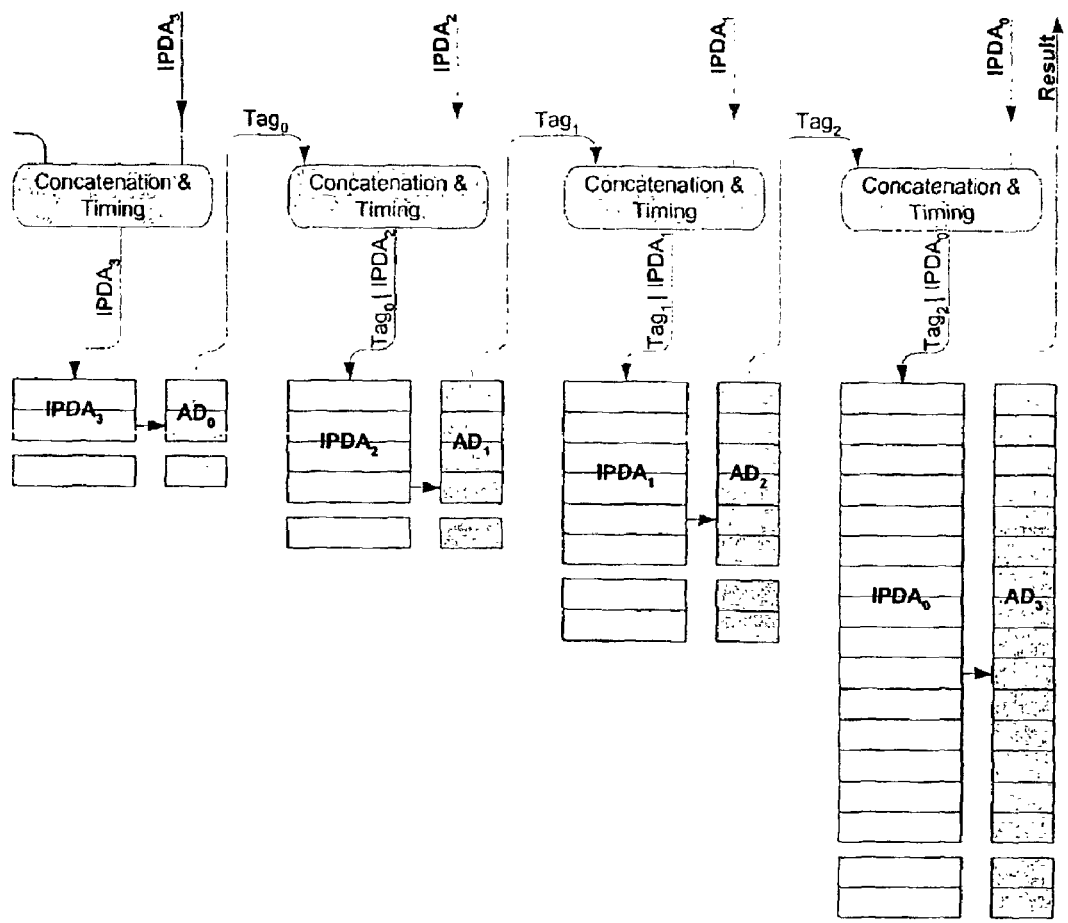
FIG. 29 is a schematic arrangement of Four RSE Sections for IPv6 Forwarding.

FIG. 29 shows an arrangement of four RSE sections for forwarding a submitted IPv6 packet. The first field of the submitted IPDA, designated $IPDA_3$, is searched in the first field ($IPDA_3$) of the stored IPDAs, yielding $AD_0$. This result is assigned a tag $Tag_0$, which is concatenated with the second submitted field $IPDA_2$ and with the second field of the stored IPDAs. Then, the tagged submitted $IPDA_2$ ($Tag_0|IPDA_2$) is searched in the tagged stored $IPDA_2$ fields ($Tag_0|IPDA_2$) yielding $AD_1$, which assigned $Tag_1$, for concatenation with the next field $IPDA_1$ of the submitted IPDA, and so on.

This search procedure in a database of IPv6 addresses for forwarding IPv6 packets resembles the classification of four-dimensional packets and requires the storage of a number of tagged fields that increases moderately, as compared to a number of fields that increases exponentially in the conventional forwarding method, yielding high compression of the stored information.

5. Maximizing the Multi-Dimensional Search Throughput by Pipelining

The most important parameter in every Classification System is its throughput expressed in number of classifications performed per second. The performance of a d-Dimensional Classification System, such as shown in FIG. 21, is determined by the following parameters:

T—Clock cycle of the signal used to clock the Classification System components.

L—Search latency for each RSE in the Classification System, expressed in the number of clocks taken from the submission of the $k_i$ Key element to the $\Re_i^1$ RSE to the appearance of a valid $Tag_i$ or the action A at the output of $\Re_i^1$. It is assumed that all the RSE stages have the same latency L.

d—Number of dimensions or RSE stages.

$T_c$—Time taken to perform a single Classification.

$F_c$—Classification throughput or the maximum number of Classifications per second that can be performed by the Classification System.

$$T_c = d \cdot L \cdot T$$

$T_c$ is also the Classification System Latency, which is the time taken from the start of a Key Classification until the Classification result is available.

A Classification can start only after the previous one has been completed. The Classification throughput is:

$$F_c = \frac{1}{d \cdot L \cdot T}$$

Thus, the Classification System Latency is proportional to the number of fields or dimensions applied. This may become a problem if the latency is too long. However, in practical cases, this time may be as long as 1000 nsec for 10 fields or dimensions. Even for a critical application, such as an ultra high-performance Switch/Router, this latency is tolerable.

However, the degradation in throughput is not tolerable. Let's assume that the single RSE throughput is 250 Million lookups per second (Mlps).

The implementation of a 10-field Classification in this fashion would result in a Classification System capable of 25 Million classifications per second (Mcps). For some applications, the number of classification fields can be greater, and therefore severely degraded.

Figure 30:
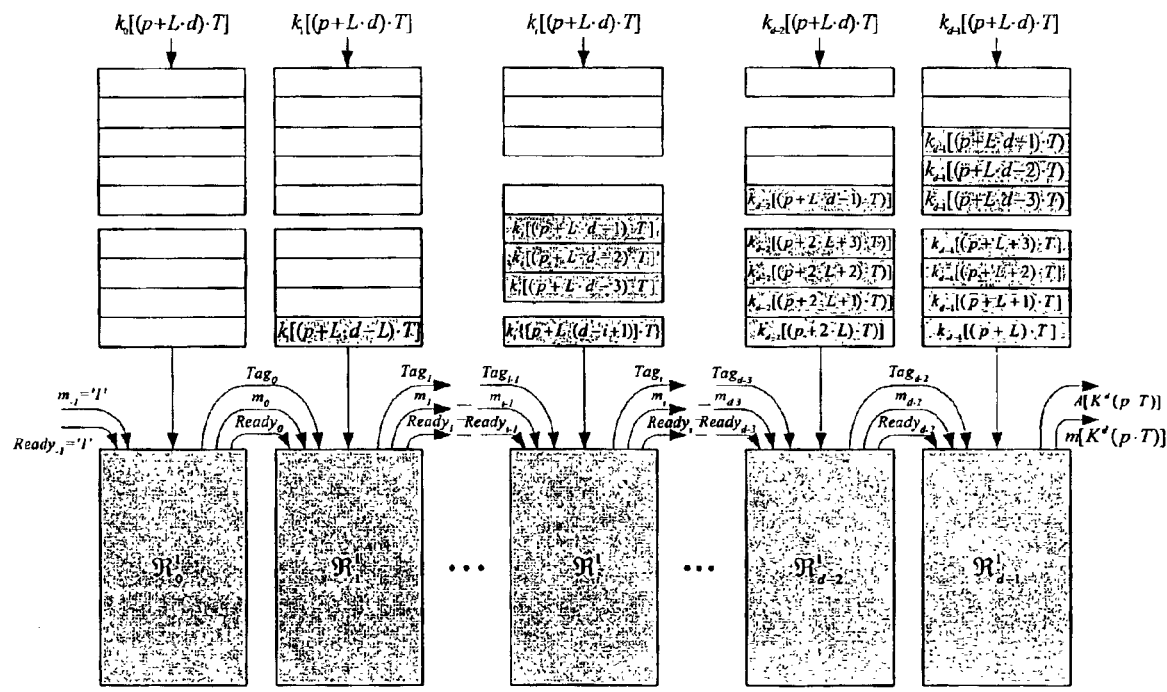
FIG. 30 is a schematic illustration of a Fully Pipelined d-Dimensional Key Search Using d RSE Devices.

Since the basic RSE is capable of a full Lookup Pipeline at a constant rate, this problem may be easily overcome, as shown in FIG. 30.

Each stage of the one-dimensional RSEs $\Re_0^1, \Re_1^1, \ldots, \Re_{d-1}^1$ is capable of simultaneously performing L Lookups in a pipelined fashion.

Thus, while the 0-dimension field Key $k_0[(p+L \cdot d) \cdot T]$ is input to the RSE $\Re_0^1$, this engine processes Lookups on Keys $k_0[(p+L-d \cdot 1) \cdot T]$ to $k_0[(p+L \cdot d-L+1) \cdot T]$ and outputs the $Tag_0$ result for the Key $k_0[(p+L \cdot d-L) \cdot T]$. The accompanying match signal $m_0$ indicates whether the Lookup for $k_0[(p+L \cdot d-L) \cdot T]$ results in a miss or a hit.

The operation of the next stage $\Re_1^1$ is synchronized by the $Ready_0$ signal, which originates in $\Re_0^1$ and accompanies the $Tag_0$ and the $m_0$ results. When $Ready_0$ is "true", $\Re_1^1$ simultaneously samples $m_0$, $Tag_0$ and the $1^{st}$-dimension Key $k_1[(p+L \cdot d-L) \cdot T]$. Key $k_1[(p+L \cdot d-L) \cdot T]$ is concatenated with $Tag_0$ from $\Re_0^1$ SO and used as a Lookup Key in $\Re_1^1$.

Starting with $\Re_1^1$ and ending with $\Re_{d-1}^1$, a wave of new Lookups starts execution on the concatenated Keys of the type $Tag_i|k_i[(p+L \cdot d-L \cdot i) \cdot T]$, $1 \leq i < d-1$.

At the same time, the last-dimension RSE $\Re_{d-1}^1$ starts the Lookup execution on the Key $Tag_{d-1}|k_{d-1}[(p+L) \cdot T]$, executes Lookups on Keys $Tag_{d-1}|k_{d-1}[(p+L-1) \cdot T]$ to $Tag_{d-1}|k_{d-1}[(p+1) \cdot T]$, and outputs the result for the Key $Tag_{d-1}|k_{d-1}[p \cdot T]$. This is actually the classification result for the Key $K^d(p \cdot T)$ that was submitted for Search at the p-th clock.

$$K^d(p \cdot T) = [k_0(p \cdot T), k_1(p \cdot T), \ldots k_{d-1}(p \cdot T)]$$

Thus, at the $(p+L \cdot d)^{th}$ clock cycle, the Classification System performs $L \cdot d$ simultaneous classifications on $L \cdot d$ submitted d-dimensional Keys, from $K^d[(p+1) \cdot T]$ to $K^d[(p+L \cdot d) \cdot T]$, and outputs $A[K^d(p \cdot T)]$, which is the classification result for $K^d(p \cdot T)$, provided that $m[K^d(p \cdot T)] = '1'$.

Thus, this Classification System is capable of outputting one classification result at every clock cycle. The machine throughput $F_c$ is:

$$F_c = \frac{1}{T}$$

It can be seen that the machine throughput does not depend on the number of classification dimensions, d, nor on the single RSE stage latency $L \cdot T$.

The total latency of this system is not better than the latency of the non-pipelined Classification System, that is, $$T_c = d \cdot L \cdot T$$

It is important to note that a proper pipeline operation requires a variable delay from the Key submission time to the start of the Key Associated Search in each dimension. No delay is required to start the search in $\Re_0^1$.

Since the result of this Key Search is output by $\Re_0^1$ after $L \cdot T$ clock cycles, and since this result is required to perform the search in the $1^{st}$ dimension RSE $\Re_1^1$, then the $1^{st}$-dimension Key must be stored and delayed for $L \cdot T$ clock cycles before being applied. For pipeline operation, $\Re_1^1$ must be capable of storing L $1^{st}$-dimension Keys.

Similarly, the $2^{nd}$-dimension RSE $\Re_2^1$ must delay the Key data by $2 \cdot L \cdot T$ clocks, and must be capable of storing the $2 \cdot L$ $2^{nd}$-dimension Keys, and so on for the succeeding dimensions. The last RSE $\Re_{d-1}^1$ must delay the Key data by (d-1)•L•T clocks and must be capable of storing [(d-1)•L] (d-1)$^{th}$-dimension Keys.

The Classification System shown in FIG. 30 uses the Ready signal, originating in one RSE stage and input to the following RSE stage, to properly time the start of the execution search in this latter stage. Also, each stage is equipped with a queue capable of storing all the queued Keys until their execution starts. The longest queue is of course attached to the $\Re_{d-1}^1$ stage and must store (d-1)•L Keys.

It is important to note that the outlined method is in no way limited to RSEs. The same method applies to other one-dimensional memory types, such as Binary and Ternary CAMs, provided that there is an Associated Data linked to the Key Entry memory. Furthermore, it is possible to use the most appropriate type of associative memory for any given field and intermix associative memory types, as needed, to implement a Classification System.

6. Link Diagrams

A link diagram is a technique that maps classification rules into the Classification System. It shows the ranges in each dimension as well as their linkage to the ranges in the follow-on dimension. The last dimension specifies the actions to be performed on a multi-dimensional Key that matches the rule.

Note: In the notation used in the examples shown below, it is implied that all the ranges (in all dimensions) that are not included in the link diagram do not match the rule; also, no default actions are specified for the submitted multi-dimensional Keys that do not match the rules. An alternative notation may specify a default action for all the Keys that do not match the rule.

EXAMPLE 8

Figures 31A, 31B:
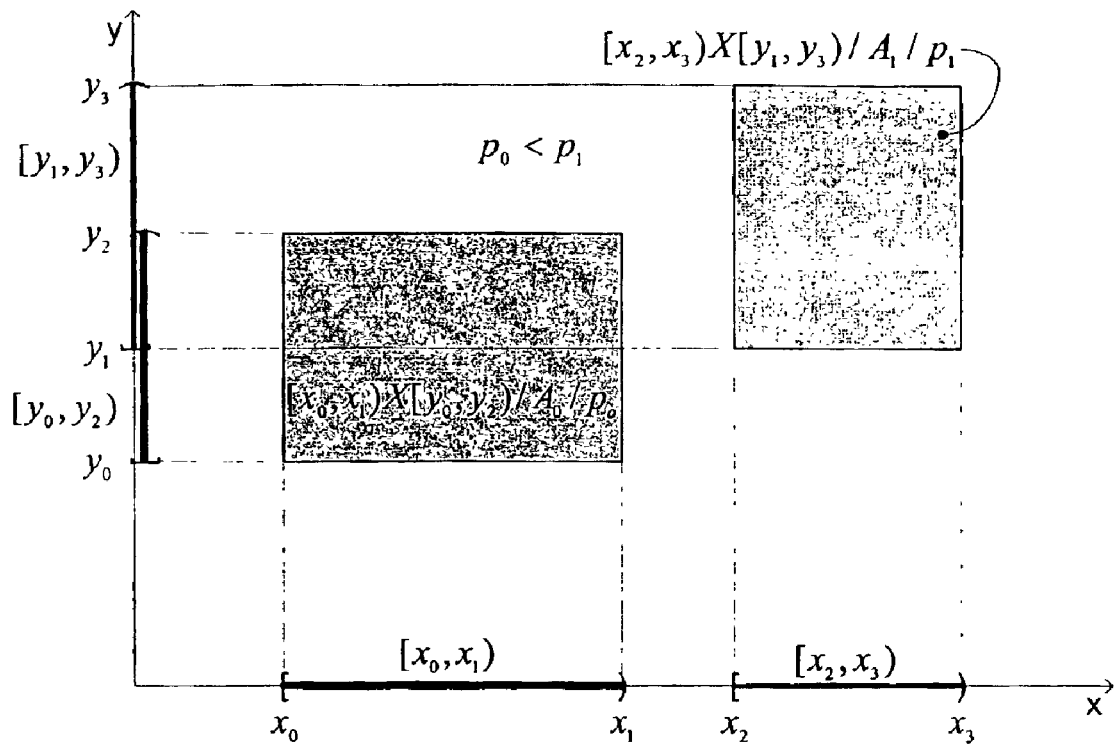
FIG. 31a shows Rule R1 for Two Disjoint Two-Dimensional Ranges with Overlapping Projections in y Direction.
FIG. 31b is a Link Diagram for Rule $R_1$.

This example describes the case of two disjoint two-dimensional ranges with overlapping projections in the y direction. FIG. 31a depicts the two-dimensional rule for this case.

By convention, all the projected boundaries are marked on the x-axis and on the y-axis in their ascending order; that is, the one closer to the origin has a lower index. The closest projected point is marked with index 0. Thus, the x-dimension and y-dimension boundaries are ordered as follows:

$$x_0 < x_1 < \ldots < x_{n-1} < x_n$$

and $$y_0 < y_1 < \ldots < y_{n-1} < y_n$$

Note: This convention is important because it enables the algebraic manipulation and determination of overlapping range domains. Algebraic manipulation can be implemented in either software or hardware-embedded algorithms.

We use the Range Algebra presented in Chapter 3 to express a rule in a convenient and compact fashion. The rule $R_1$ depicted by FIG. 31a can be expressed by the following algebraic formula:

$$R_1 = [x_0, x_1) X [y_0, y_2) / A_0 / p_0 + [x_2, x_3) X [y_1, y_3) / A_1 / p_1$$

The Link Diagram for $R_1$ equivalent to the algebraic expression above is shown in FIG. 31b. The entries at the left side of the diagram belong to the x dimension. Altogether, there are four entries; two define the range $[x_0, x_1)$ and two define the range $[x_2, x_3)$. The four entries at the right side of the diagram belong to the y dimension, and define the two ranges $[y_0, y_2)$ and $[y_1, y_3)$. The links between the two x-dimension ranges and the two y-dimension ranges describe the rule $R_1$.

A Key $K^2 = (k_x, k_y)$ is submitted for a search. If $k_x \in [x_0, x_1)$, then the Associated Data (which is the tag $T_0$) is output and used as a link to the $T_0 | [y_0, y_2)$ entry in the y-dimension RSE. If, also, $T_0 | k_y \in T_0 | [y_0, y_2)$, then $K^2 = (k_x, k_y) \in [x_0, x_1) X [y_0, y_2)$. Thus, the action $A_0$ is taken.

Similarly, if $k_x \in [x_2, x_3)$, then the tag $T_1$ is used as a link to the $T_1 | [y_1, y_3)$ entry. If, besides, $T_1 | k_y \in T_1 | [y_1, y_3)$, then $K^2 = (k_x, k_y) \in [x_2, x_3) X [y_1, y_3)$, and the action $A_1$ is taken.

The associated data in the x dimension are the tags that link the x-dimension results with a search over a subset of tagged ranges in the y dimension. The two tags must be different in order to yield Lookups in the appropriate range subset.

If the Key $K^2 = (k_x, k_y)$ submitted for a search lies outside of the two disjoint two-dimensional ranges, then it does not match rule $R_1$; a default action may be specified for this case.

Table 8a lists the links between the x-dimension and y-dimension ranges for $R_1$. Table 8b lists the corresponding links between the lower close boundaries of ranges in the two dimensions, in accordance with the instant storage method in RAM-based RSE devices.

TABLE 8a

List of Linked Ranges for Rule $R_1$

| x Dimension | Tag | y Dimension | Action |
|---|---|---|---|
| $[x_0, x_1)$ | $T_0$ | $T_0 | [y_0, y_2)$ | $A_0$ |
| $[x_1, x_2)$ | $T_1$ | $T_1 | [y_1, y_3)$ | $A_1$ |

TABLE 8b

List of Linked Range Boundaries for Rule $R_1$

| x Dimension | Tag | y Dimension | Action |
|---|---|---|---|
| $x_0$ | $T_0$ | $T_0 | y_0$ | $A_0$ |
| $x_1$ | $T_0$ | $T_0 | y_2$ | $A_0$ |
| $x_2$ | $T_1$ | $T_1 | y_1$ | $A_1$ |
| $x_3$ | $T_1$ | $T_1 | y_3$ | $A_1$ |

EXAMPLE 9

Figures 32A, 32B:
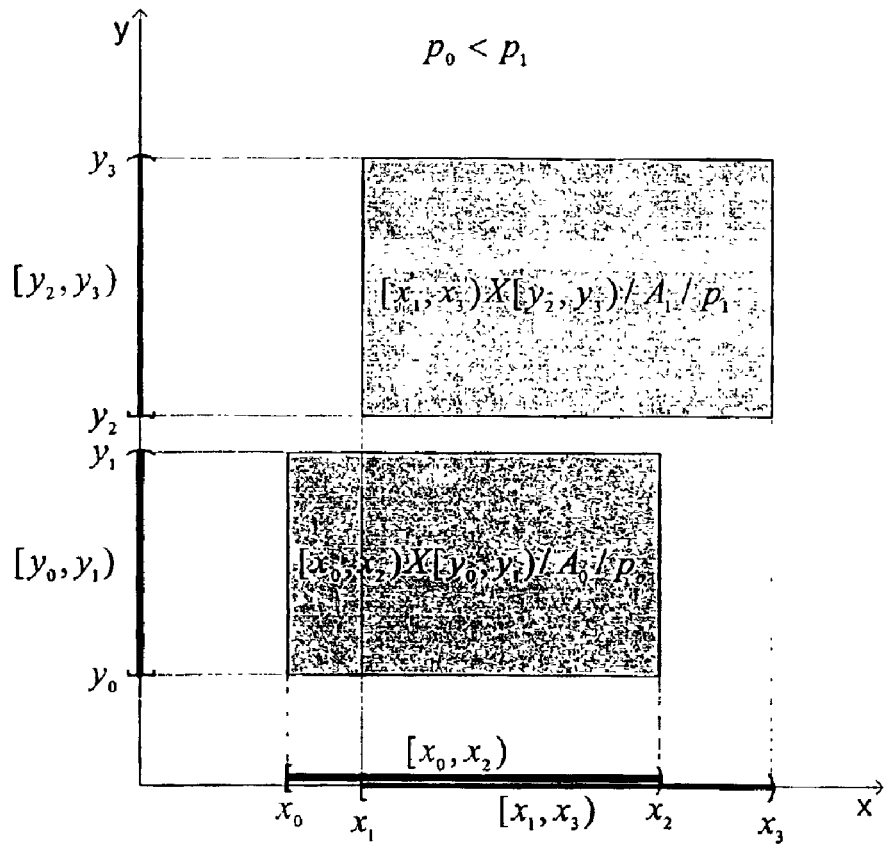
FIG. 32a shows Rule $R_2$ for two Disjoint Two-Dimensional Ranges with Overlapping Projections in x Direction.
FIG. 32b is a Link Diagram for Rule $R_2$.

This example deals with two disjoint two-dimensional ranges overlapping in the x direction, as shown in FIG. 32a. The rule $R_2$ depicted by FIG. 32a is equivalently expressed by the following algebraic formula:

$$R_2 = [x_0, x_2) X [y_0, y_1) / A_0 / p_0 + [x_1, x_3) X [y_2, y_3) / A_1 / p_1$$

$$= \{[x_0, x_1) + [x_1, x_2)\} X [y_0, y_1) / A_0 / p_0 +$$

$$\{[x_1, x_2) + [x_2, x_3)\} X [y_2, y_3) / A_1 / p_2$$

$$= [x_0, x_1) X [y_0, y_1) / A_0 / p_0 + [x_1, x_2) X \{[y_0, y_1) / A_0 / p_0 +$$

$$[y_2, y_3) / A_1 / p_1\} + [x_2, x_3) x [y_2, y_3) / A_1 / p_1$$

The associated Link Diagram for this rule is shown in FIG. 32b. In this particular case, three separate tags are required. The y-dimension range $[y_0, y_1)$ is tagged once with $T_0$ and once with $T_1$. Similarly, $[y_2, y_3)$ is tagged once with $T_1$ and once with $T_2$.

Table 9a lists the links between the x-dimension and y-dimension ranges for $R_2$. Table 9b lists the corresponding links between the lower close boundaries of ranges in the two dimensions, suitable for the present storage method in RAM-based RSE devices.

TABLE 9a

List of Linked Ranges for Rule $R_2$

| x Dimension | Tag | y Dimension | Action |
|---|---|---|---|
| $[x_0,x_1)$ | $T_0$ | $T_0[[y_0,y_1)$ | $A_0$ |
| $[x_1,x_2)$ | $T_1$ | $T_1[[y_0,y_1)$ | $A_0$ |
|  |  | $T_1[[y_2,y_3)$ | $A_1$ |
| $[x_2,x_3)$ | $T_2$ | $T_1[[y_2,y_3)$ | $A_1$ |

TABLE 9b

List of Linked Range Boundaries for Rule $R_2$

| x Dimension | Tag | y Dimension | Action |
|---|---|---|---|
| $x_0$ | $T_0$ | $T_0|y_0$ | $A_0$ |
| $x_1$ | $T_0$ | $T_0|y_1$ | $A_0$ |
|  | $T_1$ | $T_1|y_0$ | $A_0$ |
|  |  | $T_1|y_2$ | $A_1$ |
| $x_2$ | $T_1$ | $T_1|y_1$ | $A_0$ |
|  |  | $T_1|y_3$ | $A_1$ |
|  | $T_2$ | $T_2|y_2$ | $A_1$ |
| $x_3$ | $T_2$ | $T_2|y_3$ | $A_1$ |

EXAMPLE 10

Figure 33A:
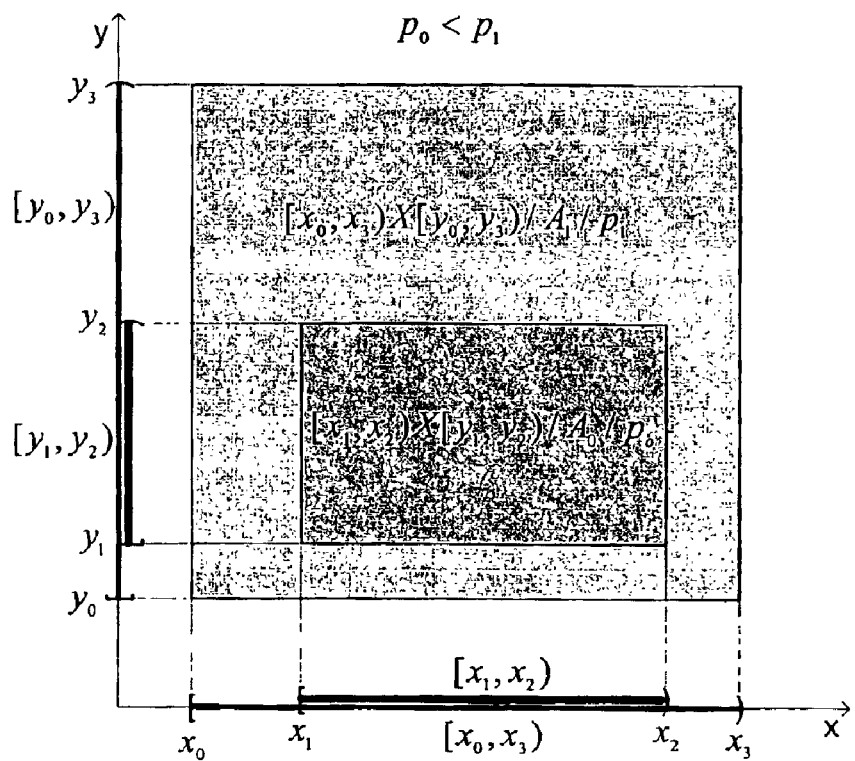
FIG. 33a shows Rule $R_3$ for two Fully Overlapping Two-Dimensional Ranges (one being a Proper Sub-Range of the other)

In this example, one two-dimensional range is a proper sub-range of the other two-dimensional range, as shown in FIG. 33a. The following algebraic formula expresses the rule $R_3$ depicted by FIG. 33a:

$$R_3 = \{[x_0, x_1) + [x_2, x_3)\}X[y_0, y_3)/A_1/p_1 +$$
$$[x_1, x_2)X\{[y_0, y_3)/A_1/p_1 + [y_1, y_2)/A_0/p_0\}$$
$$= \{[x_0, x_1) + [x_2, x_3)\}X[y_0, y_3)/A_1/p_1 +$$
$$[x_1, x_2) + X\{[y_0, y_1)/A_1/p_1 + [y_1, y_2)/A_0/p_0 +$$
$$[y_2, y_3)/A_1/p_1\}$$

Figure 33B:
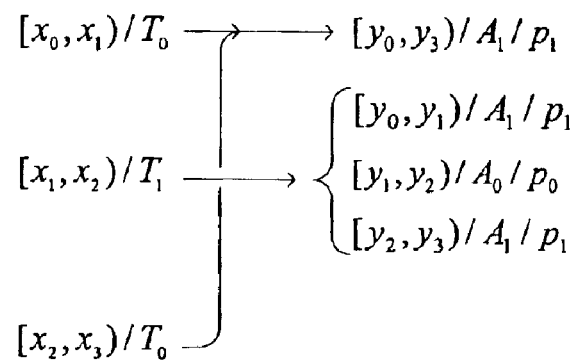
FIG. 33b is a Link Diagram for Rule $R_3$.

FIG. 33b depicts the associated Link Diagram. In this case, only two separate tags are required. Two x-dimension ranges, $[x_0,x_1)$ and $[x_2,x_3)$, are tagged with $T_0$, because both are linked to the same y-dimension range $[y_0,y3)$.

Table 10a lists the links between the x-dimension and y-dimension ranges for $R_3$. Table 10b lists the corresponding links between the lower close boundaries of ranges in the two dimensions, suitable for the inventive storage method for utilization in RSE devices. The link between $[x_2,x_3)$ and $[y_0,y_3)$ by $T_0$ (shadowed) is redundant because it also serves $[x_0,x_1)$; thus, $T_0[[y_0,y_3)$ appears only once in the stored database.

TABLE 10a

List of Linked Ranges for Rule $R_3$

| x Dimension | Tag | y Dimension | Action |
|---|---|---|---|
| $[x_0,x_1)$ | $T_0$ | $T_0[[y_0,y_3)$ | $A_1$ |
| $[x_1,x_2)$ | $T_1$ | $T_1[[y_0,y_1)$ | $A_1$ |
|  |  | $T_1[[y_1,y_2)$ | $A_0$ |
|  |  | $T_1[[y_2,y_3)$ | $A_1$ |
| $[x_2,x_3)$ | $T_0$ | $T_0[[y_0,y_3)$ | $A_1$ |

TABLE 10b

List of Linked Range Boundaries for Rule $R_3$

| x Dimension | Tag | y Dimension | Action |
|---|---|---|---|
| $x_0$ | $T_0$ | $T_0|y_0$ | $A_1$ |
| $x_1$ | $T_0$ | $T_0|y_3$ | $A_1$ |
|  | $T_1$ | $T_1|y_0$ | $A_1$ |
|  |  | $T_1|y_1$ | $A_0$ |
|  |  | $T_1|y_2$ | $A_1$ |
| $x_2$ | $T_1$ | $T_1|y_1$ | $A_1$ |
|  |  | $T_1|y_2$ | $A_0$ |
|  |  | $T_1|y_3$ | $A_1$ |
|  | $T_0$ | $T_0|y_0$ | $A_1$ |
| $x_3$ | $T_0$ | $T_0|y_3$ | $A_1$ |

EXAMPLE 11

Figures 34A, 34B:
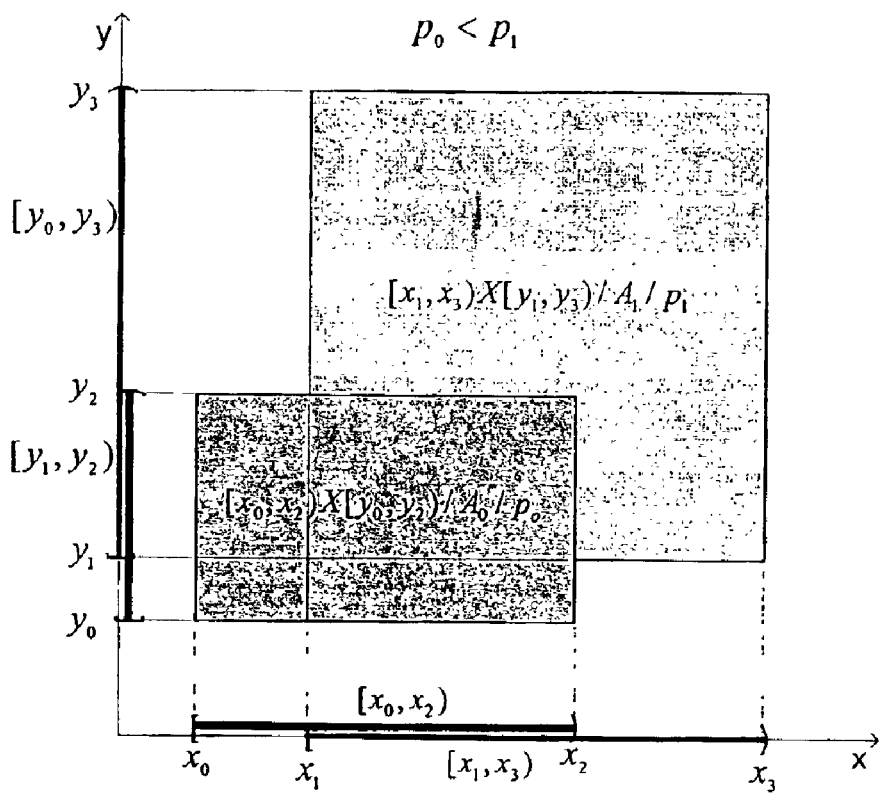
FIG. 34a shows Rule $R_4$ for two Partially Overlapping Two-Dimensional Ranges
FIG. 34b is a Link Diagram for Rule $R_4$.

This example deals with two partially overlapping two-dimensional ranges in the x and y directions, as shown in FIG. 34a. The following algebraic formula expresses the rule $R_3$ depicted by FIG. 34a:

$$R_4 = [x_0, x_2)X[y_0, y_2)/A_0/p_0 + [x_1, x_3)X[y_1, y_3)/A_1/p_1$$
$$= \{[x_0, x_1) + [x_1, x_2)\}X[y_0, y_2)/A_0/p_0 +$$
$$[x_1, x_2)X[y_2, y_3)/A_1/p_1 + [x_2, x_3)X[y_1, y_3)/A_1/p_1$$
$$= [x_0, x_1)X[y_0, y_2)/A_0/p_0 + [x_1, x_2)X\{[y_0, y_2)/A_0/p_0 +$$
$$[y_2, y_3)/A_1/p_1\} + [x_2, x_3)X[y_1, y_3)/A_1/p_1$$

FIG. 34b depicts the associated Link Diagram. In this particular case, three separate tags are required. The y-dimension range $[y_0,y_2)$ is tagged once with $T_0$ and once with $T_1$.

Table 11a lists the links between the x-dimension and y-dimension ranges for $R_4$. Table 11b lists the corresponding links between the lower close boundaries of ranges in the two dimensions, in accordance with the inventive storage method implemented in RSE devices.

TABLE 11a

List of Linked Ranges for Rule $R_4$

| x Dimension | Tag | y Dimension | Action |
|---|---|---|---|
| $[x_0,x_1)$ | $T_0$ | $T_0[[y_0,y_2)$ | $A_0$ |
| $[x_1,x_2)$ | $T_1$ | $T_1[[y_0,y_2)$ | $A_0$ |
|  |  | $T_1[[y_2,y_3)$ | $A_1$ |
| $[x_2,x_3)$ | $T_2$ | $T_1[[y_2,y_3)$ | $A_1$ |

TABLE 11b

List of Linked Range Boundaries for Rule $R_4$

| x Dimension | Tag | y Dimension | Action |
|---|---|---|---|
| $x_0$ | $T_0$ | $T_0|y_0$ | $A_0$ |
| $x_1$ | $T_0$ | $T_0|y_2$ | $A_0$ |
|  | $T_1$ | $T_1|y_0$ | $A_0$ |
|  |  | $T_1|y_2$ | $A_1$ |
| $x_2$ | $T_1$ | $T_1|y_2$ | $A_0$ |
|  |  | $T_1|y_3$ | $A_1$ |
|  | $T_2$ | $T_2|y_1$ | $A_1$ |
| $x_3$ | $T_2$ | $T_2|y_3$ | $A_1$ |

EXAMPLE 12

Two partially overlapping two-dimensional ranges in the x and y directions, containing redundant information, are provided in FIG. 35.

Figure 35A:
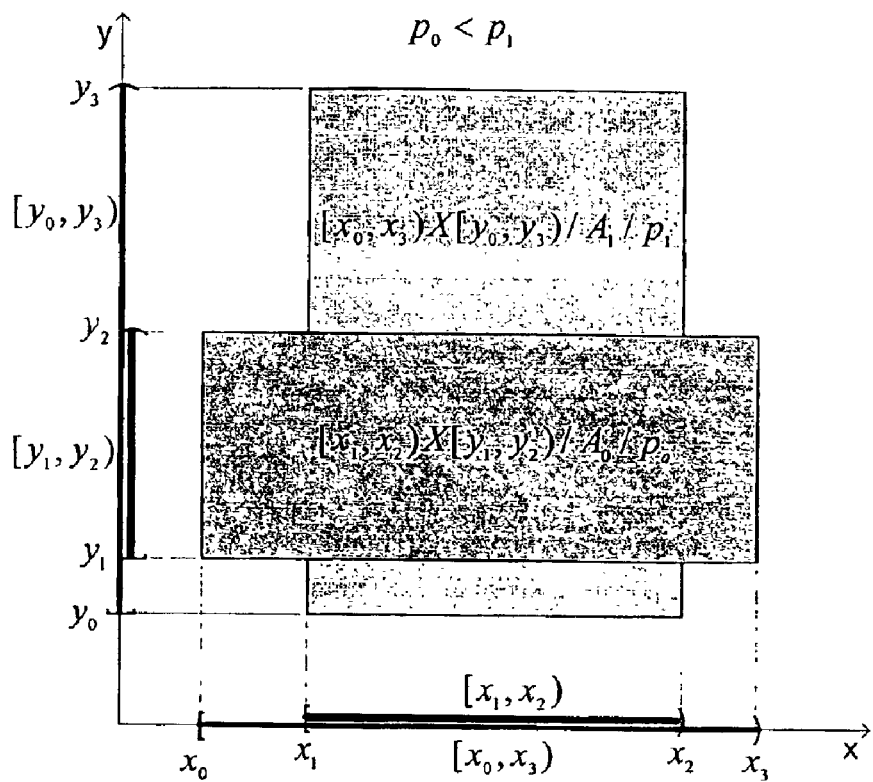
FIG. 35a shows Rule $R_5$ for two Partially Overlapping Two-Dimensional Ranges.

The following algebraic formula expresses the rule $R_3$ depicted by FIG. 35a:

$$R_5 = [x_0, x_1)X[y_1, y_2)/A_0/p_0 + [x_1, x_2)X\{[y_0, y_1)/A_1/p_1 +$$

$$[y_1, y_2)/A_0/p_0 + [y_2, y_3)/A_1/p_1\} +$$

$$[x_2, x_3)X[y_1, y_2)/A_0/p_0$$

$$= \{[x_0, x_1) + [x_2, x_3)\}X[y_1, y_2)/A_0/p_0 + \{[y_0, y_1)/A_1/p_1 +$$

$$[y_1, y_2)/A_0/p_0 + [y_2, y_3)/A_1/p_1\}$$

Figure 35B:
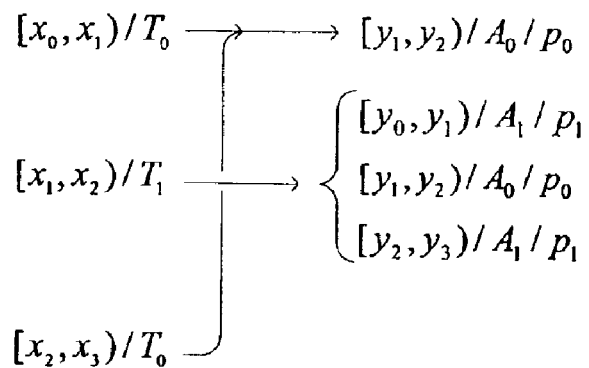
FIG. 35b is a Link Diagram for Rule $R_5$.

FIG. 35b depicts the associated Link Diagram. In this case, only two separate tags are required. Two x-dimension ranges, $[x_0,x_1)$ and $[x_2,x_3)$, are tagged with $T_0$, because both are linked to the same y-dimension range $[y_1,y_2)$.

Table 12a lists the links between the x-dimension and y-dimension ranges for $R_5$. Table 12b lists the corresponding links between the lower close boundaries of ranges in the two dimensions, suitable for the inventive storage method used in RSE devices. Similarly to the redundant link in $R_3$, the link between $[x_2,x_3)$ and $[y_1,y_2)$ by $T_0$ (shadowed) is redundant because it also serves $[x_0,x_1)$; thus, $T_0[[y_1,y_2)$ appears only once in the stored database.

TABLE 12a

List of Linked Ranges for Rule $R_5$

| x Dimension | Tag | y Dimension | Action |
|---|---|---|---|
| $[x_0,x_1)$ | $T_0$ | $T_0[[y_1,y_2)$ | $A_1$ |
| $[x_1,x_2)$ | $T_1$ | $T_1[[y_0,y_1)$ | $A_1$ |
|  |  | $T_1[[y_1,y_2)$ | $A_0$ |
|  |  | $T_1[[y_2,y_3)$ | $A_1$ |
| $[x_2,x_3)$ | $T_0$ | $T_0[[y_1,y_2)$ | $A_1$ |

TABLE 12b

List of Linked Range Boundaries for Rule $R_5$

| x Dimension | Tag | y Dimension | Action |
|---|---|---|---|
| $x_0$ | $T_0$ | $T_0|y_1$ | $A_1$ |
| $x_1$ | $T_0$ | $T_0|y_2$ | $A_1$ |
|  | $T_1$ | $T_1|y_0$ | $A_1$ |
|  |  | $T_1|y_1$ | $A_0$ |
|  |  | $T_1|y_2$ | $A_1$ |
| $x_2$ | $T_1$ | $T_1|y_1$ | $A_1$ |
|  |  | $T_1|y_2$ | $A_0$ |
|  |  | $T_1|y_3$ | $A_1$ |
|  | $T_0$ | $T_0|y_1$ | $A_1$ |
| $x_3$ | $T_0$ | $T_0|y_2$ | $A_1$ |

Comparing Example 8 (for two disjoint two-dimensional ranges with disjoint projections in the x direction and overlapping projections in the y direction) and Example 9 (for two disjoint two-dimensional ranges with disjoint projections in the y direction and overlapping projections in the x direction), it can be seen that Rule $R_1$ in Example 8 is much simpler and can be expressed with a smaller number of ranges. Generalizing, it is simpler, faster and more storage efficient to perform the multi-dimensional classification procedure starting in the directions where the projections of the multi-dimensional ranges are disjoint and then proceeding in the directions where the projections overlap.

If the multi-dimensional ranges contain fields with single values, such as the first three fields in the IPv4 Classification Key (FIG. 24), it is most efficient to integrate the single-valued fields into one separate field (or dimension) and apply the classification procedure (by exact match) in this field first, and then proceed with the ranges in the directions with disjoint projections, as mentioned before. Although exact match can be viewed as a special case of a range, it is preferable to represent it as a binary match because it leads to a storage-efficient representation (requires one integer value, instead of two, required in range representation).

Example 10 (where one two-dimensional range is a proper sub-range of another two-dimensional range) and Example 12 (a special case of two partially overlapping two-dimensional ranges) are similar in having two different x-dimension ranges concatenated to the same y-dimension range. In both cases the same Tag $T_0$ serves to concatenate the ranges in the two dimensions. This representation prevents redundancy in the storage of the y-dimension range and in the rule expressions.

Single tagging to the same range can be viewed as pointers directed to the same addresses in Directed Acyclic Graphs (DAGs). DAGs, generally used in software, are implemented in RSE hardware to reduce the amount of stored data and rule expressions, by preventing the repetition of redundant data. DAGs used in this way provide a great advantage over Trie structures, where the same addresses appear repeatedly in different branches, leading to more complicated rules and storage explosion.

The algebraic formulas associated with the link diagrams, show that single tagging to the same range is reflected in grouping the two different x-dimension ranges concatenated with the same y-dimension range inside the brackets. This can be seen as the application algebraic Distributive Law, listed hereinabove, to separate the redundant terms in the as common factors in the formulas. The order of operations is first on the terms grouped inside the brackets (or parentheses) and then on the resulting term with the common factor separated outside the brackets. In the conventional classification methods, represented by Trie structures, the expanded algebraic expression is used and the distributed terms undergo separate operations; thus, the same terms appear repeatedly, requiring to larger expressions and more terms to be stored. This can be clearly seen in the following simple example.

EXAMPLE 13

This example shows the difference between the number of range terms and operations in the grouped and expanded algebraic expressions.

$$\{[a,b)+[c,d)\}\cdot\{[e,f)+[g,h)+[j,k)\}=[a,b)\cdot[e,f)+[a,b)\cdot[g,h)+[a,b)\cdot[j,k)+[c,d)\cdot[e,f)+[c,d)\cdot[g,h)+[c,d)\cdot[j,k)$$

The left-hand grouped expression contains 5 range terms. The order of operations is first the execution of 5 OR operations within the two brackets, and then one AND operation on the two results, totaling 6 operations.

The equivalent right-hand expanded expression contains 12 terms. The order of operations is first the execution of 6 AND operations, and then 5 OR operations on the six results, totaling 11 operations.

If each range boundary consists of 32 bits, then the 10 range boundaries of the 5 range terms in the grouped expression contain 10×32=320 bits, whereas the expanded expression, with 24 range boundaries for 12 range terms, requires 24×32=768 bits.

This advantage in the number of stored terms, combined with the advantages provided by the inventive Range Representation over the prefix notation in more compact storage and aggregation of CIDR address ranges, results in much smaller storage space in the RSE in comparison with any TCAM.

Multi-field classification can be applied to numerous practical problems solving. A few applications are listed below:

Medicine: A set of rules may include a CIB aimed at identifying a disease. Another set of rules may define symptoms of cancerous cells, and be applied to scan the human body to identify all the locations of the cancerous cells.

Industry: Planning the three-dimensional motion of a robot's arm moving amidst solid obstacles and aimed at reaching predefined coordinates. In this case, the set of rules pertain to the positioning of the solid obstacles.

Criminology: Sorting out individuals who are potentially involved in a crime to be resolved. This can be done considering fingerprints, hair, eye and skin color, height, DNA, age, gender, language spoken, accent, address, car ownership, etc. These and other attributes can be listed as rules in a CIB. A query that describes the suspect is submitted to the CIB, and a list of all potential suspects that meet the description is issued.

Data Communications: Routers classify data packets to determine which policies, actions and measures must be taken. These actions are based upon predefined data packet fields and a set of rules stored in the Classifier/CIB. The fields themselves, their location in the packet header and their meaning, vary on the basis of the networking protocols used for communications. Since the Internet is a vastly accepted world standard, the examples provided hereinbelow are oriented towards this standard, in particular to TCP/IP, which mainly deals with layers 3 and 4 of the Open Systems Interconnection (OSI)-like Reference model. It should be emphasized, however, that other layers, such as layer 1 (interface), layer 2 (media access) and layer 7 (data or content), are often used to improve the classification-based decision making. Packet classification results in instructing the router to perform specific actions on the packet. Examples of these action decisions are:

Allow or deny the packet through the router: This decision is defined as Packet Filtering. By excluding packets that may pose a security risk to a network or to its nodes, network usage is made safer and its resources are dedicated to its main function—productive communication among the users.

Guaranteeing a committed level of service: Provided that a Service Level Agreement (SLA) is signed in between the service provider that owns the router and a customer, customer packets are authenticated and provided a required level of service. For instance, voice packets can be routed via an ATM network, which guarantees a low delay path required to facilitate voice communications. Similarly, video packets may be routed through a different port, which guarantees a high throughput. Another example is the preferential treatment of certain packets under congestion conditions, such that they are serviced while other packets are dropped. Using several fields from the packet header, the router can identify the Quality of Service (QoS) required and authenticate the eligible service level. Of course, the SLA involves non-standard treatment as well as higher service cost charged to the customer.

Packet accounting: Packet accounting serves a two-fold purpose. First, accounting information is collected on the packets that receive a special service and which imply higher service cost. The collected information typically includes the accumulated number of packets, the total number of transferred bytes and the time of service. Packet accounting can be motivated also by network security. For instance, intrusion into a protected system can be identified, by identifying an abnormal number of attempts to establish a connection with a certain destination in a predefined amount of time, or by observing a scan activity—characterized by packets attempting to establish a connection with a range of sequential destination addresses and/or ports. Similarly, a router can classify packets on the basis of specified rules applied to the packet fields. A classification filter-matching packet is counted and the total count is applied to detect a Denial of Service (DoS) attack.

As used herein in the specification and in the claims section that follows, the term "single integer data" and the like refer to entries that correspond to a single string containing 0's, 1's or a combination thereof. An example of single integer data is 01101011, which would be exactly matched by the following input key 01101011. The term "single integer data" is specifically meant to exclude range data of various forms, including 01X010XX and [1, 27).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A device for storing data in a memory, and for extracting the data therefrom based on a multi-dimensional input (MDI) key, the device comprising:

(a) a first associative search engine (ASE), and
(b) at least a second ASE, each ASE including:
  (i) a memory having:
    (A) a first array of cells containing a field of entries, each of said cells having a unique address and being accessible via an input key including a string corresponding to at least a portion of the MDI key, and
    (B) a second array of cells having a plurality of associated data entries, each of said associated data entries being associated with a particular one of said entries in said first array, and
  (ii) control logic for said memory, said control logic operatively connecting said first ASE and said second ASE, said control logic designed and configured for processing at least a portion of said entries in said first array from each said ASE, in response to said input key, so as to make a determination if there exists a match between said input key and an entry of said entries in said field;

said control logic designed and configured to produce a result based on said determination, wherein said result pertains to at least one of said associated data entries, and wherein said control logic utilizes said result from said first ASE in said processing of said second ASE, so as to narrow searching within said second ASE.

2. The device of claim 1, wherein each said field is configured so as to correspond to at least a portion of the MDI key.

3. The device of claim 2, wherein each said field is configured so as to correspond to a different portion of the MDI key.

4. The device of claim 1, wherein said result from said first ASE is incorporated within said input key of said second ASE.

5. The device of claim 1, further comprising:
(c) at least one concatenating element for concatenating said result from said first ASE in said input key of said second ASE to form a concatenated input key.

6. The device of claim 5, wherein each said concatenating element is operatively paired with each said at least second ASE.

7. The device of claim 5, wherein said concatenating element is designed and configured such that said result forms at least one most significant bit of said concatenated input key.

8. The device of claim 5, wherein said at least one concatenation element is disposed within said at least second ASE.

9. The device of claim 1, further comprising:
(c) at least one selecting element for selecting, based on said result from said first ASE, a portion of said field within said first array of said second ASE so as to narrow said searching within said second ASE.

10. The device of claim 1, wherein said result includes a match indicator.

11. The device of claim 1, wherein said field of entries in said first array of at least one of said first and second ASE includes range boundary information.

12. The device of claim 11, wherein said range boundary information is a single range-boundary value.

13. The device of claim 12, wherein each said range boundary value is disposed in a separate memory cell of said first array, so as to produce a monotonic order.

14. The device of claim 11, wherein said memory is designed and configured to include:
(C) range validity information for each of said range boundary information.

15. The device of claim 11, wherein each said ASE further includes:
(iii) sorting means for arranging said range boundary information in a monotonic order within said first array.

16. The device of claim 1, wherein said first array has at least two dimensions, said first array consisting of rows and columns, said second array has at least two dimensions, said second array consisting of rows and columns, and wherein each of said associated data entries has a unique pair of row and column indices for association with a unique pair of row and column indices of a particular one of said entries within said field of entries.

17. The device of claim 16, wherein said entries in said field of at least one ASE includes single integer data, and wherein said field of entries of an ASE of said at least a second ASE includes range boundary information.

18. The device of claim 17, wherein said field including single integer data is disposed within said first ASE.

19. The device of claim 17, wherein said processing of said entries within said field of said first ASE and said field of said at least second ASE is sequentially ordered such that a single integer data field is processed first.

20. The device of claim 17, wherein said processing of said entries within said field of said first ASE and said field of said at least second ASE is sequentially ordered such that:
(i) any single integer data fields are processed prior to range fields, and
(ii) among said range fields, more disjoint fields are processed prior to less disjoint fields.

21. The device of claim 1, wherein said field of entries within said first array is maintained in a monotonic order.

22. The device of claim 1, wherein at least two of said first ASE and said at least second ASE are configured to handle a long string in a single dimension of the MDI key, the device being designed and configured to split said long string into at least two input keys, each of said input keys for inputting into a different one of said first ASE and said second ASE.

23. The device of claim 1, wherein the MDI key is one of a series of MDI keys, the device being designed and configured to process portions of said MDI keys by pipelining, so as to improve a performance of the device.

24. The device of claim 1, wherein the MDI key is one of a series of MDI keys, said series represented by $k_0 \ldots k_m$, $k_{m+1} \ldots k_n$,
wherein:
k is one of said MDI keys,
$k_0$ is a first of said MDI keys,
n is a number of a last of said MDI keys, $n \geq 1$, and
m is a number of one of said MDI keys, $n \geq m+1$,
and wherein at least two ASEs of said first ASE and said at least second ASE are designed and configured to process portions of said MDI keys by pipelining, such that said second of said ASEs processes a portion of key $k_m$ while a first of said ASEs processes a different portion of key $k_{m+1}$, so as to improve a performance of the device.

25. The device of claim 1, wherein each said associative search engine further includes:
(iii) output means for outputting said result.

26. The device of claim 1, wherein said first ASE and said at least second ASE are disposed within a single chip.

27. The device of claim 1, wherein the MDI key includes an IPv4 classification key.

28. The device of claim 1, wherein the MDI key includes an Ipv6 classification key.

29. A method of storing data in a memory, and for extracting the data therefrom based on a multi-dimensional input (MDI) key, the method comprising the steps of:
(a) providing a device including:
(i) a first and at least a second associative search engine (ASE), each ASE including:
(A) a memory including:
(I) a first array of cells containing a field having a plurality of entries, and
(II) a second array of cells having a plurality of associated data entries,
wherein each of said associated data entries is associated with a particular one of said entries in said first array, and
(B) control logic for said memory;
(b) inputting an input key to each said ASE, said input key including a string corresponding to at least a portion of the MDI key;
(c) processing at least a portion of said entries in said first array from each said ASE, in response to said input key, so as to make a determination if there exists a match between said input key and an entry of said entries in said field;

(d) producing a result based on said determination, said result pertaining to at least one of said associated data entries, and (e) utilizing said result from said first ASE in said processing of step (c) of said second ASE.

30. The method of claim 29, wherein each said string corresponds to a particular first array in a one-to-one correspondence.

31. The method of claim 29, wherein said processing includes searching, and wherein step (e) is performed so as to narrow said searching within said second ASE.

32. The method of claim 29, wherein said utilizing includes incorporating said result from said first ASE in said input key of said second ASE.

33. The method of claim 29, wherein said utilizing includes concatenating said result from said first ASE in said input key of said second ASE to form a concatenated input key.

34. The method of claim 33, wherein said concatenating is performed such that said result forms at least one most significant bit of said concatenated input key.

35. The method of claim 29, wherein each said input key for said first and said second ASE includes a different portion of the MDI key.

36. The method of claim 29, wherein said utilizing includes selecting a sub-set of said entries in said first array of said second ASE, based on said result from said first ASE, said sub-set being smaller than said plurality of entries in said first array of said second ASE.

37. The method of claim 29, wherein said result includes a match indicator.

38. The method of claim 29, wherein said entries in said first array of at least one of said first and second ASE include range boundary information.

39. The method of claim 38, wherein said first array has at least two dimensions, said first array consisting of rows and columns, and wherein said second array has at least two dimensions, said second array consisting of rows and columns, and wherein each of said associated data entries has a unique pair of row and column indices for association with a unique pair of row and column indices of a particular one of said range boundary information.

40. The method of claim 38, wherein said result is a singular result obtained by pre-processing over disjoint ranges.

41. The method of claim 38, wherein said result is a singular result selected from at least two results deriving from overlapping ranges by post-processing using priority rules.

42. The method of claim 29, wherein said entries in said field of at least one ASE include single integer data, and wherein said entries in said field of at least a second ASE includes range boundary information.

43. The method of claim 42, wherein said field of said at least one ASE is within said first ASE.

44. The method of claim 42, wherein said processing of said entries within said field of said first ASE and said field of said at least second ASE is sequentially ordered such that a single integer data field is processed first.

45. The method of claim 42, wherein said processing of said entries within said field of said first ASE and said field of said at least second ASE is sequentially ordered such that:

(i) any single integer data fields are processed prior to range fields, and (ii) among said range fields, more disjoint fields are processed prior to less disjoint fields.

46. The method of claim 29, wherein said first array in maintained in a monotonic order.

47. The method of claim 29, wherein at least one dimension of the MDI key has a long string, said long string being longer than a width of a particular said ASE, and wherein said long string is handled by splitting said long string into at least two input keys, each said input key for inputting in step (b) into a different one of said first ASE and said second ASE.

48. The method of claim 29, wherein steps (b) and (c) are pipelined to improve a performance of the method.

49. The method of claim 38, wherein said range boundary information is a single range-boundary value.

50. The method of claim 38, further comprising the step of:

(f) arranging each said range boundary value of said first array to produce a monotonic order.

51. A method of storing data in a memory, and for extracting the data therefrom based on a multi-dimensional input (MDI) key, the method comprising the steps of:

(a) providing a device including:
  (i) a plurality of associative search engines (ASEs) including a first ASE and at least a second ASE, each ASE including:
    (A) a memory including:
      (I) a field containing a first array of cells, and
      (II) a second array of cells, and
    (B) control logic for said memory;

(b) storing a plurality of entries within said first array of cells, such that said field is accessible via an input key including a string, said string corresponding to at least a portion of the MDI key, wherein said entries in said first array of at least one of said first ASE and said second ASE include range boundary information;

(c) storing a plurality of associated data entries within said second array of cells, such that each of said associated data entries is associated with a particular one of said entries in said first array, and (d) processing said plurality of associated data entries so as to convert overlapping ranges within said range boundary information into disjoint ranges.

52. The method of claim 51, wherein said processing to produce said disjoint ranges is based on at least one pre-determined priority rule.

53. The method of claim 51, wherein said processing to produce said disjoint ranges is pre-processing.

54. The method of claim 51, wherein said processing further includes identifying at least one redundant data entry, said redundant data entry being redundant with a particular data entry among said associated data entries.

55. The method of claim 54, wherein said processing further includes eliminating said at least one redundant data entry so as to save space in said memory.

56. The method of claim 54, wherein corresponding to said at least one redundant data entry is at least one entry of said entries in said field, and wherein said processing further includes re-associating said entry in said field with said particular data entry among said associated data entries.

57. The method of claim 54, wherein corresponding to said at least one redundant data entry and said particular data entry are a particular plurality of entries in said field, and wherein said processing further includes separating out said particular plurality of data entries in said field as a common factor, so as to save space in said memory.

* * * * *